United States Patent [19]

Mori et al.

[11] Patent Number: 4,760,136
[45] Date of Patent: Jul. 26, 1988

[54] CHARTREUSIN DERIVATIVES AND SALTS THEREOF

[75] Inventors: Hiroyuki Mori; Nobutoshi Yamada; Hideo Sugi; Kenji Kon, all of Moriyama, Japan

[73] Assignee: Ishihara Sangyo Kaisha, Ltd., Osaka, Japan

[21] Appl. No.: 726,384

[22] Filed: Apr. 23, 1985

[30] Foreign Application Priority Data

Apr. 27, 1984 [JP] Japan ................................ 59-85719
Dec. 19, 1984 [JP] Japan ................................ 59-268012
Feb. 15, 1985 [JP] Japan ................................ 60-27708
Feb. 20, 1985 [JP] Japan ................................ 60-32391
Mar. 1, 1985 [JP] Japan ................................ 60-40570

[51] Int. Cl.$^4$ ............................................. C07H 17/04
[52] U.S. Cl. .................................. 536/17.5; 536/17.2; 536/18.1
[58] Field of Search ............... 514/27; 536/17.2, 18.1, 536/17.5

[56] References Cited

U.S. PATENT DOCUMENTS 4,518,589  5/1985  Konishi et al. .................... 536/18.1
4,521,240  6/1985  Loh ..................................... 536/18.1

OTHER PUBLICATIONS

*The Merck Index*, 1976, No. 1997, p. 256.
Cancer Research 37, pp. 1666–1672, Jun. 1977–J. Patrick McGovren et al.
Eisenhuth et al.; English translation.
Johnson et al., *Cancer Treatment Reviews* (1975) vol. 2, pp. 1–31.

*Primary Examiner*—J. R. Brown
*Assistant Examiner*—Elli Peselev
*Attorney, Agent, or Firm*—Cushman, Darby & Cushman

[57] ABSTRACT

This invention relates to a novel chartreusin derivative of the general formula (I):

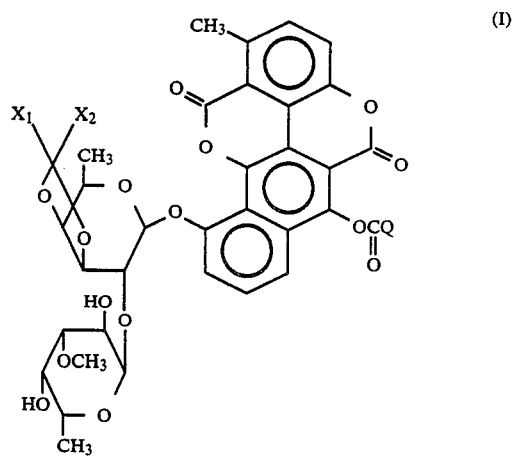

and a salt thereof. This chartreusin derivative and a salt thereof have an excellent antitumor activity, which is exhibited even when the site of cancer inoculation and the site of drug administration are different. This invention further relates to a antitumorous composition containing the above-mentioned compound as active ingredient. This invention furthermore relates to a process for producing the above-mentioned chartreusin derivative or salt thereof.

51 Claims, No Drawings

CHARTREUSIN DERIVATIVES AND SALTS THEREOF

This invention relates to a novel chartreusin derivative, a salt thereof, an antitumorous composition containing the same as active ingredient, a method for therapy of cancer using said compositions, and a process for producing the chartreusin derivative or the salt thereof.

Chartreusin has already been known to have an antitumorous activity. For example, in "Cancer Research, Vol. 37, pp. 1666-1672 (1977)", it is reported that chartreusin was effective against P-388 leukemia, L-1210 leukemia and B-16 melanoma. However, it is also reported in the same litereture that this effect was obtained in a system in which cancer was inoculated intraperitoneally followed by intraperitoneal administration of the chartreusin, and that chartreusin was not effective at all when the site of cancer inoculation and the site of chartreusin administration were different. Under these circumstances, chartreusin has not yet been developed.

The present inventors perceived the excellent antitumorous activity of chartreusin, and have conducted extensive research to allow the chartreusin derivative to always exhibit its excellent activity even when the site of cancer inoculation and the site of administration of the chartreusin derivative are different. As a result, the present inventors have found novel chartreusin derivatives which exhibit an excellent antitumorous activity even when the site of cancer inoculation and the site of drug administration are different, for example, when cancer is intraperitoneally inoculated and the drug is intravenously administered, or when cancer is subcutaneously inoculated and the drug is intravenously administered.

According to this invention, there is provided a chartreusin derivative of the general formula (I), or a salt thereof:

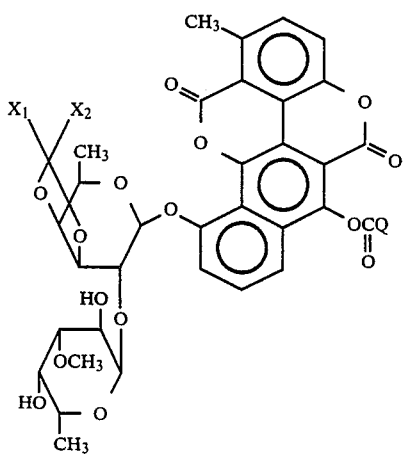
(I)

wherein $X_1$ is a hydrogen atom or a substituted or unsubstituted $C_{1-3}$alkyl group; $X_2$ is a substituted or unsubstituted $C_{1-3}$alkyl group, a substituted or unsubstituted $C_{1-2}$alkylcarbonyl-$C_{1-2}$alkyl group, a substituted or unsubstituted phenyl group, a substituted or unsubstituted phenyl-$C_{1-2}$alkyl group, a substituted or unsubstituted furyl group or a substituted or unsubstituted thienyl group; in the case where $X_1$ and $X_2$ are both substituted or unsubstituted alkyl groups at the same time, the total number of carbon atoms of these alkyl groups is 4 or less; in the case where $X_2$ is a substituted or unsubstituted phenyl group, a substituted or unsubstituted phenyl-$C_{1-2}$alkyl group, a substituted or unsubstituted furyl group or a substituted or unsubstituted thienyl group $X_1$ is a hydrogen atom; $X_1$ and $X_2$, when taken together with the adjacent carbon atom, may form a substituted or unsubstituted $C_{3-7}$cycloalkylidene; and Q is

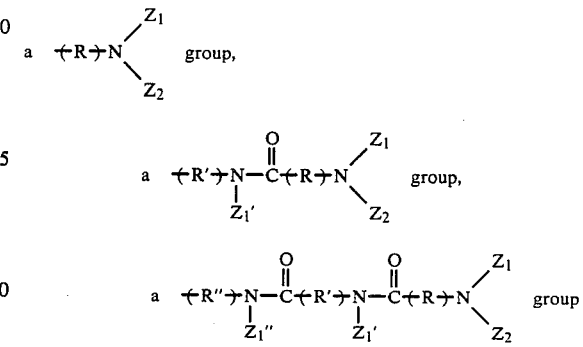

(in these three formulas, each of R, R' and R" is a substituted or unsubstituted $C_{1-11}$alkanediyl group, a substituted or unsubstituted $C_{2-11}$alkenediyl group, a substituted or unsubstituted $C_{2-11}$alkynediyl group, a substituted or unsubstituted $C_{3-10}$cycloalkanediyl group, a substituted or unsubstituted $C_{5-10}$cycloalkenediyl group, or a substituted or unsubstituted phenylene group; each of $Z_1$, $Z_1'$ and $Z_1''$ is a hydrogen atom or a substituted or unsubstituted $C_{1-6}$alkyl group; and $Z_2$ is a hydrogen atom, a substituted or unsubstituted $C_{1-6}$alkyl group, a formyl group, a substituted or unsubstituted $C_{1-6}$alkylcarbonyl group, a substituted or unsubstituted benzoyl group, or a substituted or unsubstituted benzyloxycarbonyl group; $Z_1$ and $Z_2$, when taken together with the nitrogen atom, may form a substituted or unsubstituted nitrogen-containing $C_{2-10}$heterocyclic group), a substituted or unsubstituted $C_{1-11}$alkyl group, a substituted or unsubstituted $C_{2-11}$alkenyl group, a substituted or unsubstituted $C_{3-11}$alkynyl group, a substituted or unsubstituted $C_{3-10}$ cycloalkyl group, a substituted or unsubstituted $C_{5-10}$cycloalkenyl group, a substituted or unsubstituted $C_{1-10}$alkylcarbonyl group, a substituted or unsubstituted $C_{1-10}$alkoxycarbonyl group or a substituted or unsubstituted phenyl group, the total number of atoms of Q other than the hydrogen atoms being 30 or less.

This invention further provides an antitumorous composition comprising, as the active ingredient, at least one member selected from the group consisting of the above-mentioned chartreusin derivatives and salts thereof, a method for therapy of cancer using the above antitumorous composition, and a process for producing the above-mentioned chartreusin derivative or a salt thereof.

The chartreusin derivative having an excellent antitumor activity of this invention is required to have a substitutent on the OH group in the aglycone moiety of chartreusin and a substituent on each of the OH groups in the 3'-position and 4'-position of the saccharide moiety of chartreusin, and can display no excellent antitumor activity when they lack any one of these substituents. The reason why the term "substituted or unsubstituted . . . group" is used herein is that the antitumor activity is substantially determined by said . . . group regardless of the substituents. The substituent which said . . . group may have may be any group so long as it is pharmacologically acceptable and can keep the aforesaid chartreusin derivatives chemically stable.

Based on the above findings, as to the term "substituted or unsubstituted" used in the above definitions of $X_1$, $X_2$, Q, R, R', R'', $Z_1$, $Z_1'$, $Z_1''$ and $Z_2$ in the general formula (I), the substitutents which these groups may have are described in detail below.

The substituent on the $C_{1-3}$alkyl group represented by each of $X_1$ and $X_2$ is a halogen atom, a $C_{1-2}$alkoxy group, a $C_{1-2}$alkylthio group, or the line; the substituent on the $C_{1-2}$alkylcarbonyl-$C_{1-2}$alkyl group represented by $X_2$ is a halogen atom, or the like; the substituent on the phenyl group, the phenyl-$C_{1-2}$alkyl group, the furyl group or the thienyl group represented by $X_2$ is a halogen atom, a cyano group, a nitro group, a $C_{1-3}$alkyl group which may be substituted by a halogen atom or the like, a $C_{1-3}$alkoxy group which may be substituted by a halogen atom or the like, a $C_{1-3}$alkylthio group which may be substituted by halogen atom or the like, a $C_{1-3}$ alkylcarbonyl group which may be substituted by a halogen atom or the like, a $C_{1-3}$alkoxycarbonyl group which may be substituted by a halogen atom or the like, or a di-$C_{1-3}$alkylamino group which may be substituted by a halogen atom or the like; and the substitutent on the $C_{3-7}$cycloalkylydene which $X_1$ and $X_2$ form when taken together with the adjacent carbon atom is a halogen atom, a $C_{1-2}$alkoxy group, a $C_{1-2}$alkylthio group, or the like.

The combination of $X_1$ and $X_2$ is preferably a combination of $X_1$ being a hydrogen atom with $X_2$ being a substituted or unsubstituted phenyl group, a substituted or unsubstituted furyl group, or a substituted or unsubstituted thienyl group; with $X_2$ being a substituted or unsubstituted phenyl group; or with $X_2$ being a phenyl group which may be substituted in the o-position and/or m-position of the benzene nucleus. It is particularly preferred that $X_2$ is a phenyl group which is optionally substituted by a fluorine atom in the m-position of the benzene nucleus.

Next, R, R' and R'' in the definition of Q are explained below. The substitued on the $C_{1-11}$alkanediyl group, the $C_{2-11}$alkenediyl group, the $C_{2-11}$alkynediyl group, the $C_{3-10}$cycloalkanediyl group or the $C_{5-10}$cycloalkenediyl group represented by each of R, R' and R'' is a halogen atom; a hydroxyl group; a mercapto group; a $C_{1-6}$alkoxy group; a $C_{1-6}$alkylthio group; a $C_{1-6}$alkylsulfinyl group; a $C_{1-6}$alkylsulfonyl group; an aminocarbonyl group; a hydroxycarbonyl group; a $C_{1-5}$alkoxycarbonyl group; a phenyl group which is optionally substituted by a halogen atom, a hydroxyl group, a mercapto group, a $C_{1-3}$alkoxy group, a $C_{1-3}$alkylthic group or the like; or a 3-indolyl group which is optionally substituted by a halogen atom or the like. The substituent on the phenylene group represented by each of R, R' and R'' is a halogen atom, a hydroxyl group, a mercapto group, a $C_{1-6}$alkoxy group, a $C_{1-6}$alkylthio group, a $C_{1-6}$alkylsulfinyl group, a $C_{1-6}$alkylsulfonyl group, an aminocarbonyl group, a hydroxycarbonyl group, a $C_{1-5}$alkoxycarbonyl group or the like.

R, R' and R'' are preferably substituted or unsubstituted $C_{1-11}$alkanediyl groups or $C_{3-10}$cycloalkanediyl groups, more preferably substituted or unsubstituted $C_{1-5}$alkanediyl groups or $C_{3-6}$cycloalkanediyl groups, and most preferably substituted or unsubstituted $C_{1-5}$alkanediyl groups.

Further, $Z_1$, $Z_1'$, $Z_1''$ and $Z_2$ in the definition of Q are explained below. The substituent on the $C_{1-6}$alkyl group represented by each of $Z_1$, $Z_1'$, $Z_1''$ and $Z_2$ is a halogen atom, a hydroxyl group, a mercapto group, a $C_{1-3}$alkoxy group, a $C_{1-3}$alkylthio group or the like. The substituent on the $C_{1-6}$alkylcarbonyl group or the benzoyl group represented by $Z_2$ is a halogen atom, a hydroxyl group, a mercapto group, a $C_{1-3}$alkoxy group, a $C_{1-3}$alkylthio group or the like. The substituent on the benzyloxycarbonyl group represented by $Z_2$ is a halogen atom or the like. The substituent on the nitrogen-containing $C_{2-10}$heterocyclic group which $Z_1$ and $Z_2$ form when taken together with the nitrogen atom is a halogen atom, a hydroxyl group, a mercapto group, a $C_{1-3}$alkoxy group, a $C_{1-3}$alkylthio group or the like. The term "nitrogen-containing $C_{2-10}$heterocyclic group which $Z_1$ and $Z_2$ form when taken together with the nitrogen atom" means a heterocyclic group, the ring of which is composed of one nitrogen atom and 2 to 10 carbon atoms, and if necessary, an oxygen atom and/or a sulfur atom, and specific examples thereof include aziridine ($C_2$), pyrrolidine ($C_4$), morpholine ($C_4$), thiomorpholine ($C_4$), piperidine ($C_5$), heptaethyleneimine ($C_7$), etc.

The total number of atoms of Q other than the hydrogen atoms is usually 30 or less, preferably 20 or less, more preferably 15 or less.

The case where Q has neither primary, secondary nor tertiary amino group is explained below. The substituent on the $C_{1-11}$alkyl group, the $C_{2-11}$alkenyl group, the $C_{3-11}$alkynyl group, the $C_{3-10}$cycloalkyl group, the $C_{5-10}$cycloalkenyl group, the $C_{1-10}$alkylcarbonyl group or the $C_{1-10}$alkoxycarbonyl group, represented by Q is a halogen atom, a hydroxy group, a mercapto group, a cyano group, a nitro group, a $C_{1-6}$alkoxy group, a $C_{1-6}$alkylthio group, a $C_{1-6}$alkylsulfinyl group, a $C_{1-6}$alkylsulfonyl group, a $C_{1-6}$alkylcarbonyl group, a $C_{1-6}$alkoxycarbonyl group, a phenoxycarbonyl group, a $C_{1-6}$alkylcarbonyloxy group, a $C_{3-7}$cycloalkyl group, a phenyl group, a phenoxy group, a phenylthio group, a phenylsulfinyl group, a phenylsulfonyl group, a benzoyl group, a benzoyloxy group, a benzyloxy group or the like. (The above-mentioned $C_{1-6}$alkoxy group, $C_{1-6}$alkylthio group, $C_{1-6}$alkylsulfinyl group, $C_{1-6}$alkylsulfonyl group, $C_{1-6}$alkylcarbonyl group, $C_{1-6}$alkoxycarbonyl group, phenoxycarbonyl group, $C_{1-6}$alkylcarbonyloxy group, $C_{3-7}$cycloalkyl group, phenyl group, phenoxy group, phenylthio group, phenylsulfinyl group, phenylsulfonyl group, benzoyl group, benzoyloxy group, benzyloxy group or the like may be further substituted. The substituent is a halogen atom, a hydroxyl group, a mercapto group, a $C_{1-3}$alkoxy group, a $C_{1-3}$alkylthio group or the like.)

The substituent on the phenyl group represented by Q is a halogen atom, a hydroxy group, a mercapto group, a cyano group, a nitro group, a $C_{1-6}$alkylsulfinyl group, a $C_{1-6}$alkylsulfonyl group, a $C_{1-6}$alkyl group, a $C_{1-6}$alkoxy group, a $C_{1-6}$alkylthio group, a $C_{1-6}$alkylcarbonyl group, a $C_{1-6}$alkoxycarbonyl group, a $C_{1-6}$alkylcarbonyloxy group or the like. (The above-mentioned $C_{1-6}$alkyl group, $C_{1-6}$-alkoxy group, $C_{1-6}$alkylthio group, $C_{1-6}$alkylcarbonyl group, $C_{1-6}$alkoxycarbonyl group, $C_{1-6}$alkylcarbonyloxy group or the like may be further substituted. The substituent is a halogen atom, a hydroxyl group, a mercapto group, a $C_{1-3}$alkoxy group, a $C_{1-3}$alkylthio group or the like.)

In this case, Q is preferably a substituted or unsubstituted $C_{1-11}$alkyl group, a substituted or unsubstituted $C_{2-11}$alkenyl group, a substituted or unsubstituted $C_{3-10}$cycloalkyl group or a substituted or unsubstituted phenyl group, more preferably a substituted or unsubstituted $C_{1-11}$alkyl group, a substituted or unsubstituted $C_{3-10}$cycloalkyl group or a substituted or unsubstituted phenyl group, and most preferably a substituted or unsubstituted $C_{1-11}$alkyl group or a substituted or unsubstituted $C_{3-10}$cycloalkyl group.

The total number of atoms of Q other than hydrogen atom is usually 30 or less, preferably 20 or less, and more preferably 15 or less.

In the above explanations, the alkyl, alkenyl or alkynyl portion of a radical comprising as a constituent an alkyl group, an alkenyl group, an alkynyl group, an alkanediyl group, an alkenediyl group, an alkynediyl group or a radical thereof may be of either a straight chain or a branched chain. Specific examples of, for instance, the alkyl group include methyl, ethyl, propyl, hexyl, undecyl, etc. Specific examples of the cycloalkyl and cycloalkenyl portions of the radical comprising as a constituent a cycloalkyl group, a cycloalkenyl group, a cycloalkanediyl group, a cycloalkenediyl group or a radical thereof include cyclopropyl, cyclopentyl, cyclohexanyl, etc. Specific examples of the halogen atom include fluorine, chlorine, bromine, etc.

The salts of the chartreusin derivatives in this invention are physiologically acceptable organic or inorganic salts, and include, for example, formates, acetates, propionates, butyrates, hydrochlorides, sulfates, phosphates, etc.

The chartreusin derivatives of this invention include their stereoisomers when $X_1$ and $X_2$ in the saccharide moiety are different. For example, there exist an exo isomer (hereinafter abbreviated as "exo form") in which of the O-substituents $X_1$ and $X_2$ in the 3'-position and 4'-position of the saccharide moiety of the chartreusin derivative, one which has a larger molecular weight is located outside with respect to the bicyclic ring system composed of a six-menbered ring of fucose and a five-membered ring of acetal; and an endo isomer (hereinafter abbreviated as "endo form") in which this O-substituent is located inside the bicyclic ring system. Although both isomers have an excellent antitumor activity, the exo form which displays an antitumor activity in a smaller dose is preferred.

Furthermore, the chartreusin derivatives of this invention have stereoisomers when Q is a $C_{2-11}$alkenyl group or when R, R' or R" is a $C_{2-11}$alkenediyl group. In the present specification, for example, when Q is

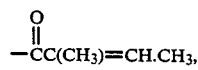
$-CC(CH_3)=CH.CH_3$, the case where the

$-C-$ group on the left side and the methyl group on the right side are upward (or downward) at the same time is defined as Zusammen (hereinafter abbreviated as (Z)), while the case where one of them is upward and the other is downward is defined as Entgegen (hereinafter abbreviated as (E)).

The compound of this invention can be produced usually by reacting a 6-O-substituted chartreusin derivative of the general formula (XII):

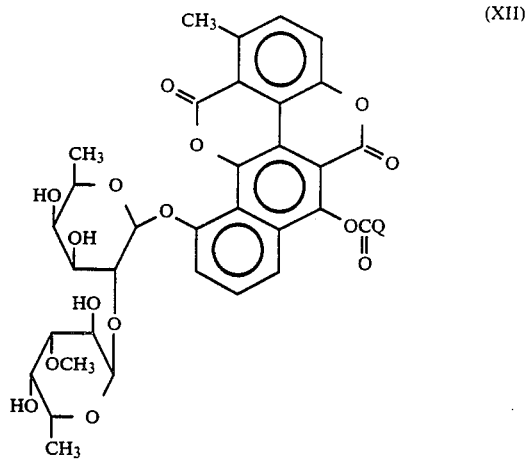

wherein Q has the same meaning as defined above, with a dimethoxy compound of the general formula

or a ketone compound of the general formula

wherein $X_1$ and $X_2$ have the same meanings as defined above, or reacting a 3', 4'-O-substituted chartreusin derivative of the general formula (IV)

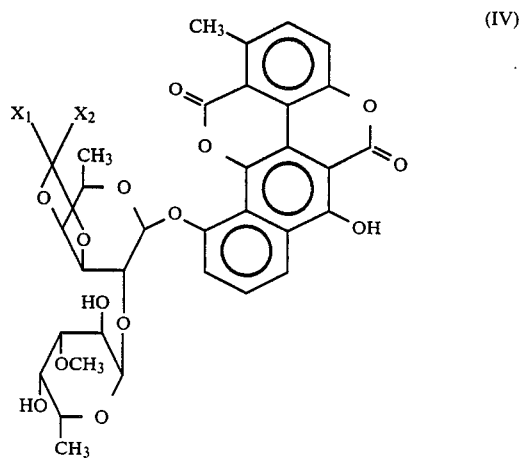

wherein $X_1$ and $X_2$ have the same meanings as defined above, with a carboxylic acid derivative of the general formula $$\overset{O}{\underset{HOCQ}{\|}} \quad (VII)$$

wherein Q has the same meaning as defined above.

Specifically, the compound of this invention can be produced, for example, by any of the following processes (A) to (C).

Process A (direct process)
[First step]

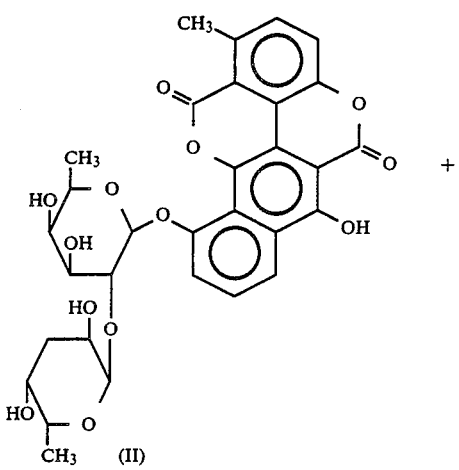
(II)

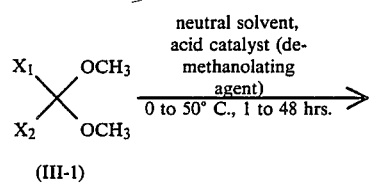
(III-1)

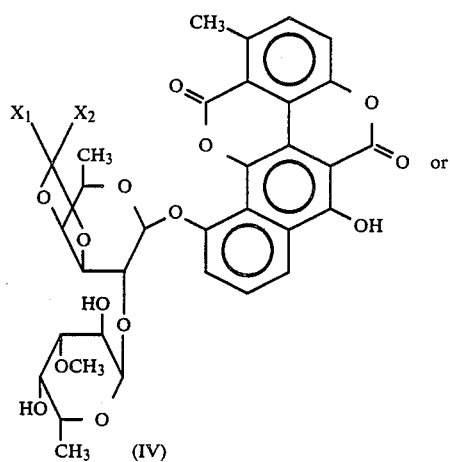
(IV)

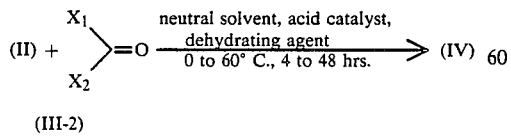
(III-2)

When $X_1$ and $X_2$ are different in the compound (IV) and separation of the stereoisomers (diastereomers) is necessary, the following separation step is additionally carried out:

Separation Step
Conventional Separation

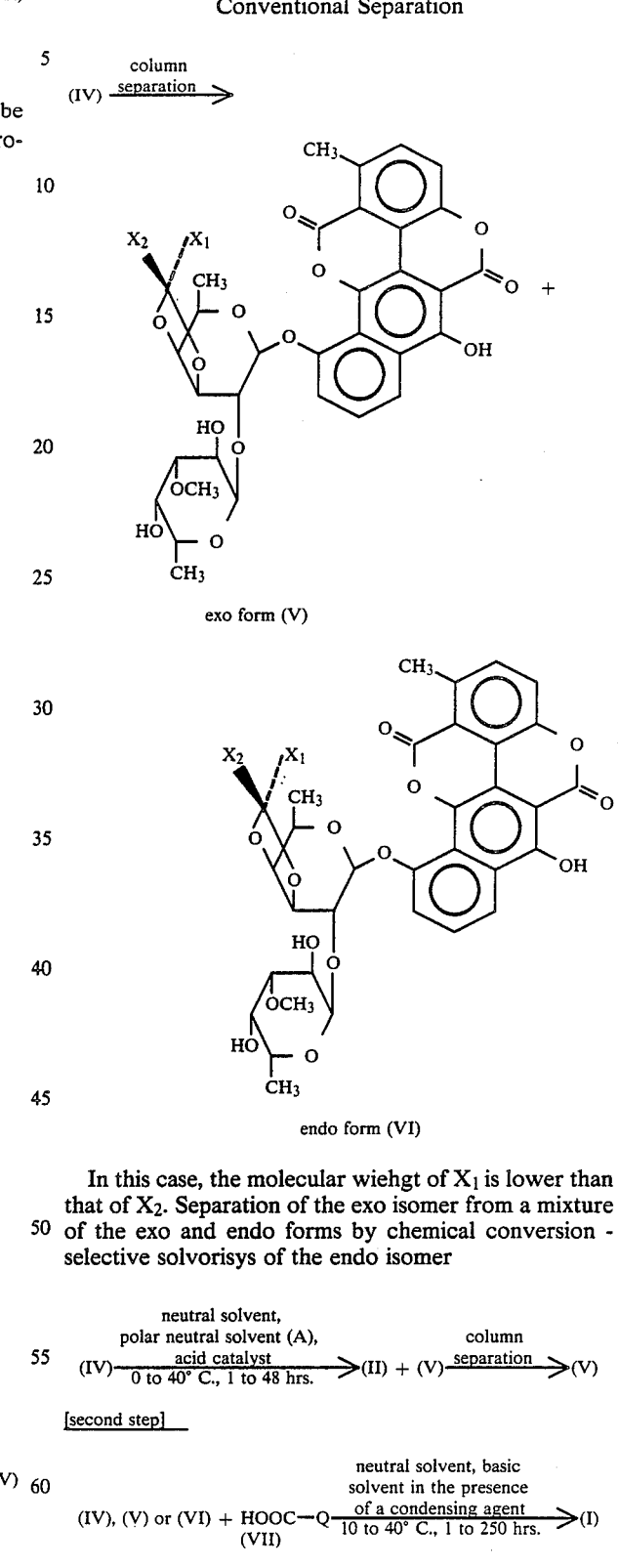

In this case, the molecular wiehgt of $X_1$ is lower than that of $X_2$. Separation of the exo isomer from a mixture of the exo and endo forms by chemical conversion - selective solvorisys of the endo isomer $$(IV) \xrightarrow[\text{0 to 40° C., 1 to 48 hrs.}]{\text{neutral solvent, polar neutral solvent (A), acid catalyst}} (II) + (V) \xrightarrow{\text{column separation}} (V)$$

[second step]

$$(IV), (V) \text{ or } (VI) + HOOC-Q \xrightarrow[\text{10 to 40° C., 1 to 250 hrs.}]{\text{neutral solvent, basic solvent in the presence of a condensing agent}} (I)$$
$$(VII)$$

In the above synthesis example (Process A), when the compound (IV) has stereoisomers (diastereomers), the ratio between the exo form (V) and the endo form (VI) in the compound (IV) can be changed to some extent by selecting the reaction conditions.

For example, in the synthesis of an unsubstituted benzylidene series compound ($X_1$: hydrogen, $X_2$: a phenyl group), the proportion of (V) is higher when (III-1) is used as a reagent than when (III-2) is used. When (III-2) is used, the proportion of (VI) is improved when the reaction temperature is lowered.

In the step of column separation of (V) and (VI), the column separation should be conducted several times because the polarities of (V) and (VI) are similar, but as described in the above example, it is also possible to obtain (V) alone with a high purity easily by a single column separation [separation between (V) and (II)] by subjecting only (VI) to selective solvolysis under weakly acidic conditions to convert (VI) into (II).

When, a group of compounds in which Q in the general formula (I) includes a primary amino group or a secondary amino group, and salts thereof [hereinafter referred to as (I-1)] are synthesized, the following reduction step is additionally carried out:

Reduction Step

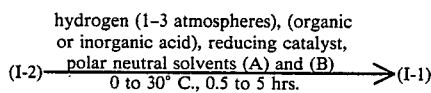

wherein (I-2) refers to a group of compounds in which Q in the general formula (I) includes an N-carbobenzyloxy group.

When a salt of compound in which Q in the general formula (I) includes a tertiary amino group is synthesized, an acid treatment step with an organic acid or an inorganic acid is additionally carried out When a group of compounds in which Q in the general formula (I) includes a hydroxyl group (hereinafter referred to as (I-3)) are synthesized, the following reduction step, for example, is additionally carried out:

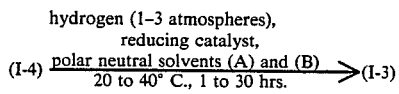

wherein (I-4) refers to a group of compounds in which Q in the general formula (I) includes a benzyloxy group.

Process B (Via Monosilyl Form)

[First Step]

The same as the first step [(II)→(IV)] of the above Process A.

[Second step]

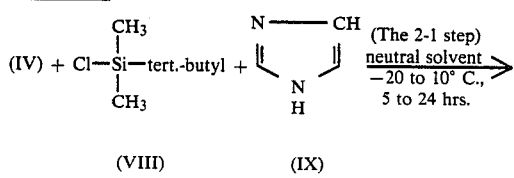

(VIII)    (IX)

[Fourth step]
(removal of the protecting group)

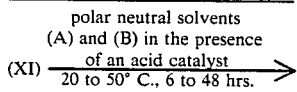

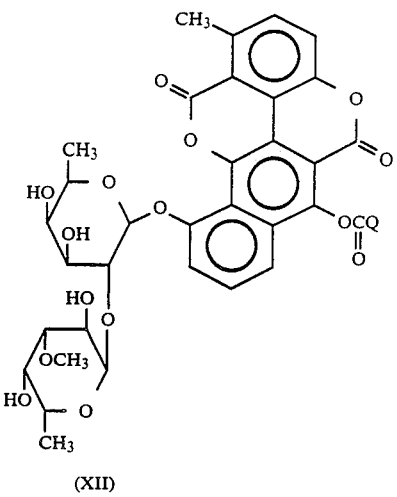

(XII)

[Fifth step]

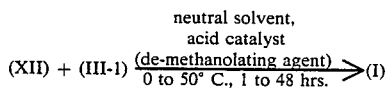

or

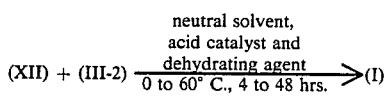

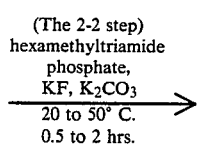

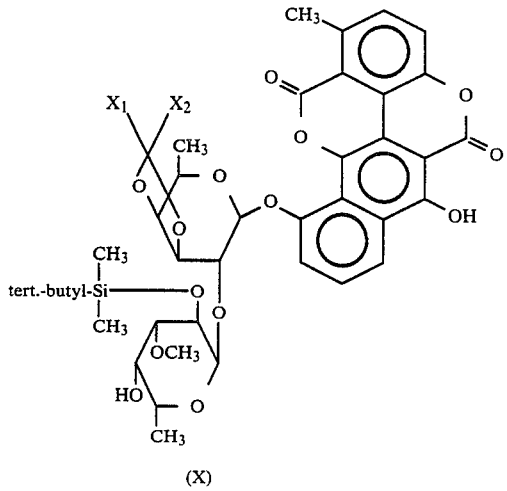

(X)

[Third step]

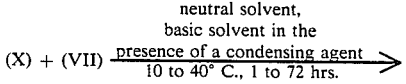

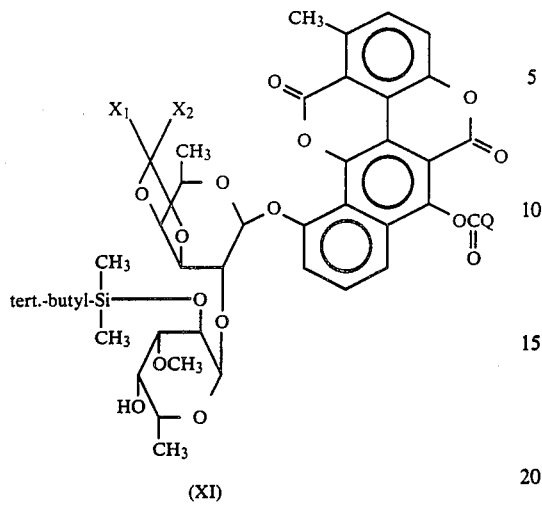

(XI)

When separation of the stereoisomers (diastereomers) is necessary in the compound (I), the separation step in the first step of the above-mentioned Process A is additionally carried out. If necessary, the reduction step in the second step of Process A is also additionally carried out.

Process C (Via Disilyl Form)

[First Step]

The same as the first step [(II)→(IV)] of the above Process A.

[Second step]

$$(IV) + (VIII) + (IX) \xrightarrow[30 \text{ to } 60° \text{ C., } 24 \text{ to } 72 \text{ hrs.}]{\text{(The 2-1 step)} \atop \text{neutral solvent}}$$

$$\xrightarrow[\substack{20 \text{ to } 50° \text{ C.,} \\ 0.5 \text{ to } 2 \text{ hrs.}}]{\substack{\text{(The 2-2 step)} \\ \text{hexamethyltriamide} \\ \text{phosphate,} \\ \text{KF, K}_2\text{CO}_3}}$$

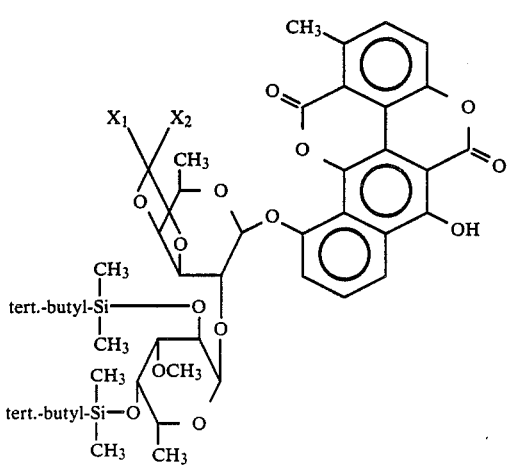

[Third Step]

((XIV) is synthesized by any of the following Methods a to d)

(Method a)

$$(XIII) + (VII) \xrightarrow[\substack{20 \text{ to } 40° \text{ C., } 1 \text{ to } 400 \text{ hrs.}}]{\text{neutral solvent, basic solvent in the} \atop \text{presence of a condensing agent}} $$

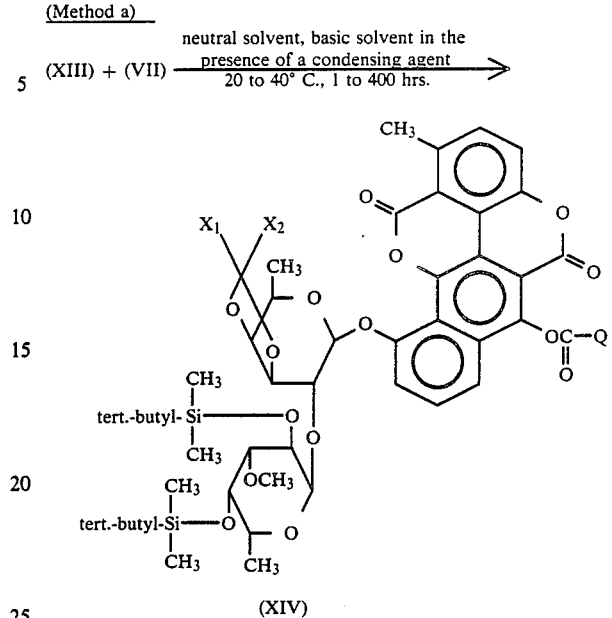

(XIV)

(Method b)

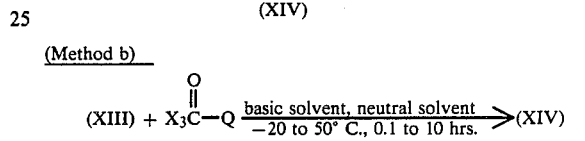

(Method c)

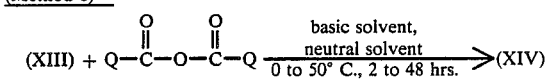

(Method d)

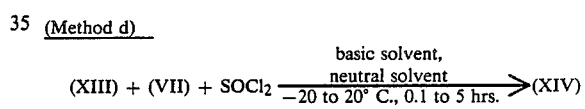

[Fourth step] (removal of the protecting group) polar neutral solvents (A) and (B) in

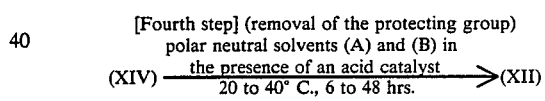

[Fifth Step]

The same as the fifth step [(XII)→(I)] of the above Process B.

When separation of the stereoisomers (diasteromers) is necessary in the compound (I), the separation step in the first step of the above Process A is additionally carried out. If necessary, the reduction step in the second step of said Process A is also applied.

$X_1$, $X_2$ and Q in the above formulas (I)–(XIV) are as defined above and $X_3$ is chlorine or bromine. The neutral solvent includes, for example, chloroform, ethyl acetate, dimethylformamide, etc. The polar neutral solvent (A) includes, for example, alcohols, water, etc. The polar neutral solvent (B) includes, for example, tetrahydrofuran, dioxane, etc. The basic solvent includes, for example, pyridine, etc. The acid catalyst includes, for example, sulfonic acids such as p-toluenesulfonic acid and the like; mineral acids such as hydrochloric acid and the like; Lewis acids such as zinc chloride and the like; etc. The de-methanolating agent includes, for example, molecular sieves, etc. The dehydrating agent includes, for example, anhydrous copper sulfate, sodium sulfate, molecular sieves, etc. The condensing agent includes carbodiimides such as dicyclohexylcarbodiimide and the like, etc. The reducing catalyst includes palladium-carbon, etc. The organic acid and the inorganic acid include, for example, formic acid, acetic acid, propionic acid, butyric acid, hydrochloric acid, sulfuric acid, phosphoric acid, etc.

Furthermore, specific synthesis examples of the intermediates (IV), (V) and (VI) are explained below, from which intermediates the compound of this invention is synthesized by Process A (direct process).

SYNTHESIS EXAMPLE 1

Synthesis of the Exo Form of 3',4'-O-Benzylidene-Chartreusin (Intermidiate No. 501)

In 500 ml of anhydrous chloroform was dissolved 20 g of chartreusin, followed by adding thereto 23.8 g of benzaldehyde dimethylacetal, 2 g of p-toluenesulfonic acid and 100 g of Molecular Sieves 5A 1/16, and the resulting mixture was subjected to reaction with stirring at room temperature for 1 hour.

After completion of the reaction, 6 ml of pyridine was added and the resulting mixture was filtered through Celite, after which the filtrate was concentrated to a volume of about 250 ml, and the resulting solution was purified by a silica gel column chromatography to obtain crystals of a mixture of the exo form and the endo form of 3',4'-O-benzylidene-chartreusin.

Subsequently, the aforesaid crystals were dissolved in 200 ml of chloroform, followed by adding thereto 25 ml of a 0.01N hydrochloric acid-methanol solution prepared from concentrated hydrochloric acid and methanol, and the resulting mixture was subjected to reaction with stirring at room temperature for 18 hours.

After completion of the reaction, several milliliters of pyridine was added, and the resulting mixture was filtered, after which the filtrate was concentrated under reduced pressure to obtain a mixture of chartreusin and the exo form of 3',4'-O-benzylidene-chartreusin. Subsequently, this mixture was subjected to a silica gel column chromatography to obtain crystals of the exo form of 3',4'-O-benzylidene-chartreusin. Said crystals wee recrystallized from a mixture of chloroform and ethanol to obtain 8.6 g of crystals of the exo form.

SYNTHESIS EXAMPLE 2

Synthesis of the Exo Form and the Endo Form of 3',4'-O-Benzylidene-Chartreusins (Intermediate Nos. 501 and 502)

In 300 ml of anhydrous chloroform was dissolved 10.0 g of chartreusin, followed by adding thereto 30 ml of benzaldehyde, 1 g of p-toluenesulfonic acid and 50 g of Molecular Sieves 4A 1/16, and the resulting mixture was subjected to reaction with stirring at room temperature for 20 hours. After completion of the reaction, the reaction mixture was filtered through Celite and the filtrate was concentrated to a volume of about 150 ml, after which the resulting solution was separated by several repetitions of a silica gel column chromatography to obtain crystals of the exo form and the endo form of 3',4'-O-benzylidene-chartreusin. The crystals of each isomer were recrystallized from a mixture of chloroform and ethanol, whereby 2.7 g of crystals of the exo form and 4.8 g of crystals of the endo form were obtained.

SYNTHESIS EXAMPLE 3

Synthesis of 3',4'-O-(o-Fluorobenzylidene)-Chartreusin (A Mixture of the Exo Form and the Endo Form at a Ratio of 1:6, Intermediate No. 503)

In 63 ml of anhydrous chloroform was dissolved 2.0 g of chartreusin, followed by adding thereto 3.3 ml of o-fluorobenzaldehyde, 200 mg of p-toluenesulfonic acid and 6 g of Molecular Sieves 4A 1/16, and the resulting mixture was subjected to reaction with stirring at 40° to 50° C. for 24 hours. After completion of the reaction, the reaction mixture was filtered through Celite, and the filtrate was concentrated, after which the concentrate was purified by several repetitions of a silica gel column chromatography to obtain crystals. The crystals were recrystallized from a mixture of chloroform and ethanol to obtain 630 mg of 3',4'-O-(o-fluorobenzylidene)-chartreusin (a mixture of the exo form and the endo form at a ratio of 1:6).

SYNTHESIS EXAMPLE 4

Synthesis of the Exo Form and the Endo Form of 3',4'-O-(m-Fluorobenzylidene)-Chartreusin (Intermediate Nos. 504 and 505)

In 250 ml of anhydrous chloroform was dissolved 5.0 g of chartreusin, followed by adding thereto 6.7 g of m-fluorobenzaldehyde dimethylacetal, 1.4 g of p-toluenesulfonic acid and 25 g of Molecular Sieves 5A 1/16, and the resulting mixture was subjected to reaction with stirring at 40° to 45° C. for 5 hours. After completion of the reaction, 3.0 ml of pyridine was added and the resulting mixture was filtered through Celite after which the filtrate was concentrated and the resulting crude crystals were separated by several repetitions of a silica gel column chromatography to obtain crystals of the exo form and the endo form of 3',4'-O-(m-fluorobenzylidene)-chartreusin. The crystals of each isomer was recrystallized from a mixture of chloroform and ethanol, whereby 503 mg of crystals of the exo form and 480 mg of crystals of the endo form were obtained.

SYNTHESIS EXAMPLE 5

Synthesis of the Endo Form of 3',4'-O-(m-Trifluoromethylbenzylidene)-Chartreusin (Intermediate No. 506)

In 30 ml of anhydrous chloroform was dissolved 1.0 g of chartreusin, followed by adding thereto 2.1 ml of m-trifluoromethylbenzaldehyde, 100 mg of p-toluenesulfonic acid and 3 g of Molecular Sieves 4A 1/16, and the resulting mixture was subjected to reaction with stirring at 20° to 25° C. for 20 hours. After completion of the reaction, the reaction mixture was filtered through Celite and the filtrate was concentrated, after which the concentrate was subjected to several repetitions of a silica gel column chromatography to obtain crystals. The crystals were recrystallized from a mixture of chloroform and ethanol to obtain 580 mg of the endo form of 3',4'-O-(m-trifluoromethylbenzylidene)-chartreusin.

SYNTHESIS EXAMPLE 6

Synthesis of 3',4'-O-(2-Furylmethylene)-Chartreusin (A Mixture of the Exo Form and the Endo Form at a Ratio of 1:1, Intermdiate No. 507)

In 50 ml of anhydrous chloroform was dissolved 1.8 g of chartreusin, followed by adding thereto 5.2 ml of furfural, 200 mg of p-toluenesulfonic acid and 5 g of Molecular Sieves 4A 1/16, and the reaction was carried out with stirring at 20° to 25° C. for 24 hours. After completion of the reaction, the reaction mixture was filtered through Celite and the filtrate was concentrated, after which the concentrate was purified by several repetitions of a silica gel column chromatography to obtain crystals. The crystals were recrystallized from a mixture of chloroform, ethanol and ether to obtain 489 mg of 3′,4′-O-(2-furylmethylene)-chartreusin (a mixture of the exo form and the endo form at a ratio of 1:1).

Intermediates Nos. 508 to 526 were synthesized according to Synthesis Examples 1 to 6 above. The structures and melting points of intermediates Nos. 501 to 526 are tabulated in Table 1, and NMR data of typical intermediates of them are shown in Table 2.

TABLE 1

| Intermediate No. | Structure [$X_1$ = hydrogen] (Note 1) | | Melting point (°C.) |
|---|---|---|---|
| | $X_2$ | Isomer (Note 2) | |
| 501 | Phenyl | Exo form | 165.0–200.0 |
| 502 | | Endo form | 262.0–266.5 |
| 503 | o-Fluorophenyl | Mixture (1:6) | 258.0–269.0 |
| 504 | m-Fluorophenyl | Exo form | 159.0–165.0 |
| 505 | | Endo form | 252.0–265.0 |
| 506 | m-Trifluoromethylphenyl | Endo form | 226.0–232.0 |
| 507 | 2-Furyl | Mixture (1:1) | 180.0–192.0 |
| 508 | p-Fluorophenyl | Exo form | 155.0–167.0 |
| 509 | | Endo form | 235.0–245.0 |
| 510 | o-Chlorophenyl | Endo form | 225.0–234.5 |
| 511 | m-Chlorophenyl | Exo form | 158.0–163.0 |
| 512 | | Endo form | 243.0–255.0 |
| 513 | p-Chlorophenyl | Exo form | 258.5–268.0 |
| 514 | | Endo form | 213.5–222.0 |
| 515 | m-Bromophenyl | Endo form | 255.0–263.0 |
| 516 | p-Bromophenyl | Exo form | 275.0–282.0 |
| 517 | | Endo form | 185.0–189.0 |
| 518 | 2,4-Dichlorophenyl | Endo form | 190.0–200.0 |
| 519 | o-Methylphenyl | Exo form | 192.0–198.0 |
| 520 | | Endo form | 238.0–243.0 |
| 521 | p-Methoxyphenyl | Exo form | 283.0–295.0 |
| 522 | m-Nitrophenyl | Endo form | 227.0–235.0 |
| 523 | 2-Phenylethyl | Exo form | 137.0–145.0 |
| 524 | 3-Thienyl | Exo form | 236.0–242.0 |
| 525 | | Endo form | 260.0–272.0 |
| 526 | pentafluorophenyl | | oily |

TABLE 1-continued

| Intermediate No. | Structure [$X_1$ = hydrogen] (Note 1) | | Melting point (°C.) |
|---|---|---|---|
| | $X_2$ | Isomer (Note 2) | |
| | substance | | |

(Note 1): $X_1$ and $X_2$ represent substituents in the intermediates (IV), (V) or (VI).
(Note 2): In the mixtures, the ratio is that of exo form to endo form.

TABLE 2

| Intermediate No. | The Assignment of NMR (60 MHz, δ value, in CDCl$_3$) | | | | | | | | | |
|---|---|---|---|---|---|---|---|---|---|---|
| | A | B | C | D | E | F | G | H* | I | Others (or remarks) |
| 501 | 1.30 | 1.48 | 2.83 | 3.40 | 5.27 | 5.89 | 6.32 | 7.17–8.23 (10H) | 11.70 | — |
| 502 | 1.10 | 1.48 | 2.81 | 3.40 | 5.30 | 5.77 | 5.98 | 7.22–8.23 (10H) | 11.67 | — |
| 504 | 1.33 | 1.49 | 2.84 | 3.43 | 5.31 | 5.91 | 6.33 | 7.00–8.30 (9H) | 11.65 | — |
| 505 | 1.12 | 1.48 | 2.79 | 3.41 | 5.37 | 5.76 | 5.96 | 7.00–8.29 (9H) | 11.62 | — |
| 506 | 1.11 | 1.46 | 2.74 | 3.36 | 5.28 | 5.67 | 5.93 | 7.08–8.18 (9H) | 11.68 | — |
| 508 | 1.27 | 1.45 | 2.77 | 3.40 | 5.28 | 5.86 | 6.29 | 7.00–8.17 (9H) | 11.57 | — |
| 509 | 1.09 | 1.46 | 2.79 | 3.41 | 5.31 | 5.74 | 5.94 | 7.00–8.21 (9H) | 11.60 | — |
| 510 | 1.10 | 1.51 | 2.85 | 3.45 | 5.39 | 5.84 | 6.40 | 7.26–8.46 (9H) | 11.63 | — |
| 512 | 1.15 | 1.47 | 2.79 | 3.40 | 5.31 | 5.70 | 5.90 | 7.14–8.27 (9H) | 11.67 | — |
| 514 | 1.16 | 1.48 | 2.84 | 3.43 | 5.38 | 5.79 | 5.99 | 7.22–8.35 (9H) | 11.57 | — |
| 515 | 1.17 | 1.49 | 2.80 | 3.47 | 5.41 | 5.82 | 5.98 | 7.20–8.38 (9H) | 11.63 | — |
| 519 | 1.27 | 1.45 | 2.80 | 3.37 | 5.27 | 5.87 | 6.47 | 7.04–8.27 (9H) | 11.67 | 2.48 (3H, s, Ar—CH$_3$) |
| 522 | 1.16 | 1.49 | 2.79 | 3.41 | 5.37 | 5.72 | 6.07 | 7.17–8.44 (9H) | 11.60 | — |
| 524 | 1.34 | 1.48 | 2.83 | 3.42 | 5.30 | 5.89 | 6.42 | 7.00–8.34 (8H) | 11.66 | H* includes the thienyl group |

A: (3H, d, J = 7Hz, —CH$_3$),
B: (3H, d, J = 7Hz, —CH$_3$),
C: (3H, s, Ar—CH$_3$),
D: (3H, s, —O—CH$_3$),
E: (1H, d, J = 8Hz, anomer proton),
F: (1H, d, J = 4Hz, anomer proton),
G: (1H, s, —O—CH—O—),
H*: (aromatic proton),
I: (1H, s, phenolic proton)

SYNTHESIS EXAMPLE 7

Synthesis of 3′,4′-O-Isopropylidene-Chartreusin (Intermediate No. 527)

In 330 ml of anhydrous chloroform was dissolved 14.0 g of chartreusin, followed by adding thereto 100 ml of 2,2-dimethoxypropane and 300 mg of p-toluenesulfonic acid, and the resulting mixture was subjected to reaction with stirring at 25° to 30° C. for 8 hours. After completion of the reaction, the reaction mixture was filtered and an aqueous sodium hydrogencarbonate solution was added, after which the resulting mixture was extracted with chloroform. The chloroform layer was washed with an aqueous sodium chloride solution and dried over anhydrous sodium solfate. Then the chloroform was removed by distillation under reduced pressure to obtain an oily substance. Subsequently, the oily substance was crystallized from a mixed solvent of chloroform, ethanol and hexane to obtain 12.5 g of 3′,4′-O-isopropylidene-chartreusin.

NMR (60 MHz, δ values in CDCl$_3$): 1.20–1.73 (12H, CH$_3$x4), 2.87 (3H, s, Ar—CH$_3$), 3.43 (3H, s, O—CH$_3$), 5.23 (1H, m, anomer proton), 5.90 (1H, m, anomer proton), 7.23–8.40 (5H, aromatic proton), 11.57 (1H, phenolic proton)

SYNTHESIS EXAMPLE 8

Synthesis of 3′,4′-O-Isobutylidene-Chartreusin (Intermediate No. 528)

In 20 ml of anhydrous chloroform was dissolved 500 mg of chartreusin, followed by adding thereto 30 ml of anhydrous methyl ethyl ketone, 800 mg of anhydrous copper sulfate and 50 mg of p-toluenesulfonic acid, and the resulting mixture was subjected to reaction with stirring at 25° to 30° C. for 48 hours. After completion of the reaction, the reaction mixture was filtered and an aqueous sodium hydrogencarbonate was added to the filtrate, after which the resulting mixture was extracted with chloroform. The chloroform layer was washed with an aqueous sodium chloride solution and dried. Then the chloroform was removed by distillation under reduced pressure to obtain an oily substance. Subsequently, the oily substance was purified by a silica gel column chromatography and then crystallized from a mixed solvent of chloroform, ethanol and hexane to obtain 125 mg of 3',4'-O-isobutylidene-chartreusin.

NMR (60 MHz, δ values in CDCl$_3$—CD$_3$SOCD$_3$): 1.00–1.73 (14H, 3Hx4, CH$_2$x1), 2.85 (3H, s, Ar—CH$_3$), 5.73 (1H, m, anomer proton), 7.27–8.27 (5H, aromatic proton), 11.67 (1H, phenodic proton)

Intermediate Nos. 529 to 531 were synthesized according to Synthesis Examples 7 and 8 above.

The structures and melting points of the intermediate Nos. 527 and 531 are tabulated in Table 3.

TABLE 3

| Intermediate No. | Structure (Note 1) X$_1$ | X$_2$ | Melting point (°C.) |
|---|---|---|---|
| 527 | Methyl | Methyl | 168.0–170.0 |
| 528 | Methyl | Ethyl | 203.0–208.0 |
| 529 | Hydrogen | Ethyl | 197.0–206.0 |
| 530 | Hydrogen | Acetylmethyl | 192.5–202.0 |
| 531 | Pentamethylene (cyclohexylidene) | | 243.5–253.5 |

(Note 1): X$_1$ and X$_2$ represent substituents in the intermediate (IV).

Next, specific synthesis examples of the intermediates (X) and (XIII) are described below, via which intermediate the compound of this invention is synthesized by Process B (via monosilyl form) and Process C (via disilyl form). Typical examples of the intermediate (XII) are listed in Table 4.

SYNTHESIS EXAMPLE 9

In 18.4 ml of anhydrous dimethylformamide was dissolved 500 mg of the 3',4'-O-isopropylidene-chartreusin (intermediate No. 527) obtained in Synthesis Example 7 above, after which 400 mg of imidazole and 444 mg of tert-butyldimethylchlorosilane were added, and the resulting mixture was subjected to reaction with stirring at 0° C. for 6 hours. After completion of the reaction, the reaction mixture was poured into an aqueous sodium hydrogencarbonate solution and the resulting mixture was extracted with chloroform. The chloroform layer was dried and the solvent was removed by distillation under reduced pressure to obtain an oily substance. The oily substance was dissoved in 10 ml of hexamethyltriamide phosphate, followed by adding thereto 85 mg of potassium fluoride and 147 mg of potassium hydrogencarbonate, and the resulting mixture was subjected to reaction with stirring at 25° C. for 30 minutes. After completion of the reaction, the reaction mixture was poured into an aqueous sodium hydrogencarbonate solution and the resulting mixture was extracted with chloroform. The chloroform layer was dried and the solvent was removed by distillation under reduced pressure to obtain an oily substance. Subsequently, the oily substance thus obtained was subjected to a silica gel column chromatography to obtain crystals, which were then recrystallized from a mixed solvent of ethanol, chloroform and hexane to obtain 520 mg of 3',4'-O-isopropylidene-2"-O-(tert-butyldimethylsilyl)-chartreusin having a melting point of 130°–135° C.

NMR (60 MHz, δ values in CDCl$_3$): −0.43 (3H, s, Si—CH$_3$), −0.22 (3H, s, Si—CH$_3$), 0.47 (9H, s, Si-tert-C$_4$H$_9$), 1.17–1.77 (12H, CH$_3$x4), 2.90 (3H, s, Ar—CH$_3$), 3.40 (3H, s, O—CH$_3$), 5.50 (2H, m, anomer proton x 2), 7.23–8.40 (5H, aromatic proton), 11.66 (1H, phenolic proton)

SYNTHESIS EXAMPLE 10

Synthesis of 3',4'-O-Isopropylidene-2",4"-Di(Tert-Butyldimethylsilyl)-Chartreusin (Intermediate No. 533)

In 18.4 ml of anhydrous dimethylformamide was dissolved 500 mg of the 3',4'-O-isopropylidene-chartreusin obtained in Synthesis Example 7 above, after which 800 mg of imidazole and 888 mg of tert-butyldimethylchlorosilane were added, and the resulting mixture was subjected to reaction with stirring at 55° to 60° C. for 48 hours. After completion of the reaction, the reaction mixture was poured into an aqueous sodium hydrogencarbonate solution and the resulting mixture was extracted with chloroform. The chloroform layer was dried and the solvent was removed by distillation under reduced pressure to obtain an oily substance. The oily substance was dissolved in 15 ml of hexamethyltriamide phosphate, followed by adding thereto 85 mg of potassium fluoride and 147 mg of potassium hydrogencarbonate, and the resulting mixture was subjected to reaction with stirring at 25° C. for 1 hour. After completion of the reaction, the reaction mixture was poured into an aqueous sodium hydrogencarbonate solution and the resulting mixture was extracted with chloroform. The chloroform layer was dried and the solvent was removed by distillation under reduced pressure to obtain an oily substance. Subsequently, the oily substance thus obtained was subjected to a silica gel column chromatography to obtain 608 mg of 3',4'-O-isopropylidene-2",4"-O-di(tert-butyldimethylsilyl)-chartreusin having a melting point of 119.5°–125.0° C.

NMR (60 MHz, δ values in CDCl$_3$): −0.38 (3H, s, 2-O-Si—CH$_3$), −0.18 (3H, s, 2"-O-Si—CH$_3$), 0.05 (6H, s, 4"-O-Si—CH$_3$x2), 0.48 (9H, s, 2"-O-Si-tert-C$_4$H$_9$), 0.88 (9H, s, 4"-O-Si-tert—C$_4$H$_9$) 1.10–1.80 (12H, CH$_3$x4), 2.28 (3H, s, Ar-CH$_3$), 3.33 (3H, s, O-CH$_3$), 5.43 (2H, m, anomer proton x 2), 7.30–8.30 (5H, aromatic proton), 11.63 (1H, phenolic proton)

TABLE 4

| Intermediate No. | (Note 1) Q | (Note 2) Rf value | Melting point (°C.) |
|---|---|---|---|
| 534 | —CH$_2$N(CH$_3$)(COCF$_3$) | 0.32 | — |
| 535 | —(CH$_2$)$_2$NHCHO | 0.16 | — |
| 536 | —(CH$_2$)$_2$NHCOCH$_3$ | 0.20 | 212.0–219.0 |
| 537 | —(CH$_2$)$_2$NHCOCCl$_3$ | 0.28 | 193.5–199.0 |

TABLE 4-continued

| Intermediate No. | (Note 1) Q | (Note 2) Rf value | Melting point (°C.) |
|---|---|---|---|
| 538 | —(CH$_2$)$_2$NHCOOCH$_2$—(phenyl) | 0.32 | — |
| 539 | —(CH$_2$)$_3$NHCOOCH$_2$—(phenyl) | 0.33 | 229.0–234.5 |
| 540 | —(CH$_2$)$_4$NHCOCF$_3$ | 0.25 | — |
| 541 | —(CH$_2$)$_5$NHCOOCH$_2$—(phenyl) | 0.33 | 243.5–249.0 |
| 542 | —(CH$_2$)$_{11}$NHCOCH$_3$ | 0.23 | 218.5–227.5 |
| 543 | —CH(CH$_3$)CH$_2$NHCOCF$_3$ | 0.26 | 222.0–230.5 |
| 544 | —CH(CH$_3$)CH$_2$NHCO—(phenyl) | 0.28 | 157.0–176.0 |
| 545 | —CH(CH$_3$)CH$_2$NHCOOCH$_2$—(phenyl) | 0.32 | — |
| 546 | —CH$_2$CH(CH$_3$)NHCOCF$_3$ | 0.26 | — |
| 547 | —(CH$_2$)$_2$NHCOCH$_2$NHCOOCH$_2$—(phenyl) | 0.25 | — |
| 548 | —CH$_3$ | 0.28 | 231.0–252.5 |
| 549 | —CH$_2$CH(CH$_3$)$_2$ | 0.33 | — |
| 550 | —(CH$_2$)$_4$CH$_3$ | 0.27 | 245.0–250.5 |
| 551 | —CH$_2$CH(CH$_3$)CH$_2$C(CH$_3$)$_3$ | 0.28 | 190.5–194.5 |
| 552 | —CH(CH$_2$CH$_3$)(CH$_2$)$_3$CH$_3$ | 0.35 | 216.5–225.0 |
| 553 | —CH(cyclopropyl with CH$_3$) | 0.31 | — |
| 554 | —(CH$_2$)$_2$—(cyclohexyl) | 0.32 | 224.0–227.5 |
| 555 | —CH=CHCH=CHCH$_3$ | 0.33 | 188.0–204.0 |
| 556 | —CH(cyclopentenyl) | 0.30 | — |
| 557 | —(CH$_2$)$_2$C≡CH | 0.28 | 245.5–256.0 |
| 558 | —CH(Br)CH(CH$_3$)$_2$ | 0.30 | — |
| 559 | —CH=C(CF$_3$)(CH$_3$) | 0.29 | — |
| 560 | —CH$_2$O—(phenyl) | 0.32 | 208.5–227.0 |
| 561 | —(CH$_2$)$_3$OCH$_2$—(phenyl) | 0.32 | — |
| 562 | —CH$_2$S—(phenyl) | 0.31 | — |
| 563 | —CH$_2$OCOCH$_3$ | 0.32 | — |
| 564 | —(CH$_2$)$_2$COCH$_3$ | 0.29 | 261.0–268.5 |
| 565 | —(CH$_2$)$_2$COOCH$_3$ | 0.29 | — |

TABLE 4-continued

| Intermediate No. | (Note 1) Q | (Note 2) Rf value | Melting point (°C.) |
|---|---|---|---|
| 566 | —(o-chlorophenyl) | 0.28 | 245.0–249.5 |
| 567 | —(p-cyanophenyl) | 0.32 | 231.5–235.0 |
| 568 | —(p-trifluoromethylphenyl) | 0.30 | 255.0–272.5 |

Note 1: Q is a substituent in the intermediate (XII).
Note 2: Rf values were measured by a silica gel thin-layer chromatography (Merk Silica Gel 60GF$_{254}$) using a mixed solvent of chloroform and methanol (8:1) as a developing solvent.

Next, specific synthesis examples of the compounds of this invention are described. The melting points of the compounds of this invention described in the synthesis examples and the NMR data of typical compounds of this invention are hereinafter collectively described.

SYNTHESIS EXAMPLE 11

Synthesis of the Exo Form of 6-O-(N,N-Diethyl-β-Alanyl)-3',4'-O-Benzylidene-Chartreusin Hydrochloride (Referred to Hereinafter as Compound No. 8)

In a mixture of 1.4 ml of anhydrous pyridine and 0.7 ml of anhydrous chloroform was dissolved 100 mg of the exo form of 3',4'-O-benzylidene-characteusin (intermediate No. 501) obtained in Synthesis Example 1 above, after which 60 mg of N',N-diethyl-β-alanine and 113 mg of dicyclohexylcarbodiimide were added, and the resulting mixture was subjected to reaction at room temperature for 4 hours.

After completion of the reaction, 10 ml of a mixed solvent of a small amount of methanol and 10 ml of a mixed solvent of chloroform and ethyl acetate (~1:10) was added. Then, the resulting mixture was filtered and the filterate was concentrated under reduced pressure, after which the oily substance thus obtained was separated by a short silica gel column chromatography, to obtain about 100 mg of a product.

The aforesaid product was dissolved in 20 ml of a mixed solvent of chloroform and ethyl acetate (~1:10) and the resulting solution was extracted with diluted hydrochloric acid. After the hydrochloric acid layer was washed with ethyl acetate, sodium chloride was added and the resulting mixture was extracted with chloroform. The chloroform layer was washed with an aqueous sodium chloride solution, thereafter dried over anhydrous sodium sulfate and then concentrated under reduced pressure to obtain 33 mg of the exo form of 6-O-(N,N-diethyl-β-alanyl)-3',4'-O-benzylidene-chartreusin.

In a mixture of 0.39 ml of a 0.1N aqueous hydrochloric acid solution and 10 ml of water was dissolved 33 mg of this chartreusin derivative, and the resulting solution was washed with ethyl acetate and then freeze-dried to obtain 33 mg of the desired compound.

SYNTHESIS EXAMPLE 12

Synthesis of the Exo Form of 6-O-(N,N-Dimethyl-β-Amino-Isobutyryl)-3',4'-O-Benzylidene-Chartreusin Hydrochloride (Hereinafter Referred to as Compound No. 1)

In a mixture of 1.7 ml of anhydrous pyridine and 0.8 ml of anhydrous chloroform was dissolved 120 mg of the exo form of 3',4'-O-benzylidene-chartreusin (intermediate No. 501) obtained in Synthesis Example 1 above, after which 43 mg of N,N-dimethyl-β-aminoisobutyric acid and 102 mg of dicyclohexylcarbodiimide were added, and the resulting mixture was subjected to reaction with stirring at room temperature for 24 hours.

After completion of the reaction, 79 mg of the desired compound was obtained in the same manner as in Synthesis Example 11 above.

SYNTHESIS EXAMPLE 13

Synthesis of the Exo Form of 6-O-(N-Trifluoroacetyl-β-Amino-Isobutyryl)-3',4'-O-Benzylidene-Chartreusin (Hereinafter Referred to as Compound No. 12)

In a mixture of 1.4 ml of anhydrous pyridine and 0.7 ml of anhydrous chloroform was dissolved 100 mg of the exo form of 3',4'-O-benzylidene-chartreusin (intermediate No. 501) obtained in Synthesis Example 1 above, after which 55 mg of N-trifluoroacetyl-β-aminoisobutyric acid and 85 mg of dicyclohexylcarbodiimide were added, and the resulting mixture was subjected to reaction with stirring at room temperature for 1 hour.

After completion of the reaction, a small amount of methanol was added. Then, the resulting mixture was filtered and the filtrate was concentrated under reduced pressure, after which the oily substance thus obtained was subjected to a silica gel thin-layer chromatography to obtain crystals. Subsequently, said crystals were recrystallized from a mixture of chloroform and ethanol to obtain 85 m of the desired compound.

SYNTHESIS EXAMPLE 14

Synthesis of the Exo Form of 6-O-(N-Trifluoroacetyl-2-Amino-Cyclohexanecarbonyl)-3',4'-O-Benzylidene-Chartreusin (Hereinafter Referred to as Compound Nos. 118 and 26)

In a mixture of 0.8 ml of anhydrous pyridine and 0.4 ml of anhydrous chloroform was dissolved 60 mg of the exo form of 3',4'-O-benzylidene-chartreusin (intermediate No. 501) obtained in Synthesis Example 1 above, after which 49 mg of N-trifluoroacetyl-2-aminocyclohexanecarboxylic acid and 59 mg of dicyclohexylcarbodiimide were added, and the resulting mixture was subjected to reaction with stirring at room temperature for 2 hours.

After completion of the reaction, a small amount of methanol was added. Then, the resulting mixture was filtered and the filtrate was concentrated under reduced pressure, after which the oily substance thus obtained was separated by a silica gel thin-layer chromatography to obtain crystals of the two isomers. The crystals of each isomer were recrystallized from a mixture of chloroform, ethanol and ether to obtain 21 mg of one of the isomers (referred to hereinafter as compound No. 118) and 21 mg of the other (referred to hereinafter as compound No. 26).

Compound No. 118 [Rf value: 0.650 (a silica gel thin-layer chromatography (Merk Silica Gel 60GF$_{254}$, developing solvent:chloroform:methanol = 15:1))]

Compound No. 26 [Rf value: 0.570 (a silica gel thin-layer chromatography (Merk Silica Gel 60GF$_{254}$, developing solvent:chloroform:methanol = 15:1))]

SYNTHESIS EXAMPLE 15

Synthesis of the Exo Form of 6-O-(N-Trifluoroacetyl-2-Amino-Cyclohexanecarbonyl)-3',4'-O-(m-Fluorobenzylidene)-Chartreusin (Referred to Hereinafter as Compound Nos. 117 and 27)

In a mixture of 0.7 ml of anhydrous pyridine and 0.3 ml of anhydrous chloroform was dissolved 50 mg of the exo form of 3',4'-O-(m-fluorobenzylidene)-cartreusin (intermediate No. 504) obtained in Synthesis Example 4 above, after which 40 mg of N-trifluoroacetyl-2-aminocyclohexanecarboxylic acid and 48 mg of dicyclohexylcarbodiimide were added, and the resulting mixture was subjected to reaction with stirring at room temperature for 2 hours. After completion of the reaction, 11 mg of one of the isomers (referred to hereinafter as compound No. 117) and 12 mg of the other (referred to hereinafter as compound No. 27), were obtained.

Compound No. 117 [Rf value: 0.645 (a silica gel thin-layer chromatography (Merk Silica Gel 60GF$_{254}$, developing solvent:chloroform methanol = 15:1))]

Compound No. 27 [Rf value: 0.560 (a silica gel thin-layer chromatography (Merk Silica Gel 60GF$_{254}$, developing solvent:chloroform:methanol = 15:1))]

SYNTHESIS EXAMPLE 16

Synthesis of the Endo Form of 6-O-(N-Trifluoroacetyl-$\beta$-Alanyl)-3',4'-O-Benzylidene-Chartreusin (Referred to Hereinafter as Compound No. 28)

In a mixture of 1.5 ml of anhydrous pyridine, 1.5 ml of anhydrous ethyl acetate and 1.5 ml of anhydrous chloroform was dissolved 110 mg of the endo form of 3',4'-O-benzylidene-chartreusin (intermediate No. 502) obtained in Synthesis Example 2 above, after which 70 mg of N-trifluoroacetyl-$\beta$-alanine and 109 mg of dicyclohexylcarbodiimide were added, and the resulting mixture was subjected to reaction with stirring at room temperature for 2 hours. After completion of the reaction, crystals were obtained in the same manner as in Synthesis Example 13 above. Subsequently, said crystals were recrystallized from a mixture of chloroform, ethanol and ether to obtain 100 mg of the desired compound.

SYNTHESIS EXAMPLE 17

Synthesis of 6-O-(N-Trifluoroacetyl-$\beta$-Alanyl)-3',4'-O-Isopropylidene-Chartreusin (Referred to Hereinafter as Compound No. 49)

In a mixture of 1.1 ml of anhydrous pyridine and 4.4 ml of anhydrous ethyl acetate was dissolved 150 mg of the 3',4'-O-isopropylidene-chartreusin (intermediate No. 527) obtained in Synthesis Example 7 above, after which 164 mg of N-trifluoroacetyl-$\beta$-alanine and 137 mg of dicyclohexylcarbodiimide were added, and the resulting mixture was subjected to reaction with stirring at 35° C. for 2 hours. After completion of the reaction, 0.5 ml of methanol was added, and the resulting mixture was filtered, after which the filtrate was concentrated under reduced pressure, and the oily substance thus obtained was separated by a silica gel thin-layer chromatography to obtain a viscous oily substance. Subsequently, said viscous oily substance was dissolved in a small amount of a mixed solvent of chloroform and ethanol, and ether was poured thereinto to form a precipitate, which was then filtered to obtain 40 mg of the desired compound.

SYNTHESIS EXAMPLE 18

Synthesis of the Exo Form of 6-O-(N-Carbobenzyloxy-S-Oxomethionyl)-3',4'-O-Benzylidene-Chartreusin (Hereinafter Referred to as Compound No. 79)

In a mixture of 0.7 ml of anhydrous pyridine and 0.3 ml of anhydrous chloroform was dissolved 50 mg of the exo form of 3',4'-O-benzylidene-chartreusin (intermediate No. 501) obtained in Synthesis Example 1 above, after which 56 mg of N-Carbobenzyloxymethionine and 57 mg of dicyclohexylcarbodiimide were added, and the resulting mixture was subjected to reaction with stirring at room temperature for 1 hour.

After completion of the reaction, a small amount of methanol was added. Then, the resulting mixture was filtered and the filtrate was concentrated under reduced pressure, after which the oily substance thus obtained was dissolved in about 20 ml of chloroform and oxidized with vigorous stirring in the atmosphere. After completion of the reaction, the reaction mixture was concentrated under reduced pressure, and the concentrate was subjected to a silica gel thin-layer chromatography to obtain crystals. Subsequently, said crystals were recrystallized from a mixture of chloroform, ethanol and ether to obtain 16 mg of the desired compound.

SYNTHESIS EXAMPLE 19

Synthesis of 6-O-(N-Carbobenzyloxy-6-Amino-n-Hexanoyl)-3',4'-O-Isopropylidene-Chartreusin (Referred to Hereinafter as Compound No. 111)

In a mixture of 1.5 ml of anhydrous pyridine and 5.9 ml of anhydrous ethyl acetate was dissolved 200 mg of the 3',4'-O-Isopropylidene-Chartreusin (intermediate No. 527) obtained in Synthesis Example 7 above, after which 462 mg of N-Carbobenzyloxy-6-Amino-n-hexanoic acid and 358 mg of dicyclohexylcarbodiimide were added, and the resulting mixture was subjected to reaction with stirring at 30° C. for 50 hours. After completion of the reaction, 145 mg of the desired compound was obtained in the same manner as in Synthesis Example 17 above.

SYNTHESIS EXAMPLE 20

Synthesis of the Exo Form of 6-O-(N-Carbobenzyloxy-Glycyl-Glycyl-Glycyl)-3',4'-O-Benzylidene-Chartreusin (Hereinafter Referred to as Compound No. 114)

In a mixture of 2.8 ml of anhydrous pyridine and 0.7 ml of anhydrous chloroform was added 100 mg of the exo form of 3',4'-O-Benzylidene-Chartreusin (intermediate No. 501) obtained in Synthesis Example 1 above, after which 104 mg of N-Carbobenzyloxy-Glycyl-Glycyl-glycine and 85 mg of dicyclohexylcarbodiimide were added, and the resulting mixture was subjected to reaction with stirring at room temperature for 72 hours.

After completion of the reaction, a small amount of methanol was added. Then the resulting mixture was concentrated under reduced pressure, and the solid thus obtained was washed with chloroform and then with ethyl acetate. The solid thus washed was dissolved in a mixed solvent of ethanol and chloroform, and the resulting solution was filtered, after which the filtrate was concentrated under reduced pressure, and the concentrate was subjected to a silica gel thin-layer chromatography to obtain crystals. Subsequently, said crystals were recrystallized from a mixed solvent of pyridine, chloroform and ether to obtain 24 mg of the desired compound.

SYNTHESIS EXAMPLE 21

Synthesis of the Endo Form of 6-O-(m-Dimethylaminobenzoyl)-3',4'-O-(m-Fluorobenzylidene)-Chartreusin (Referred to Hereinafter as Compound No. 158)

In a mixture of 0.9 ml of anhydrous pyridine and 0.5 ml of anhydrous chloroform was dissolved 70 mg of the endo form of 3',4'-O-(m-Fluorobenzylidene)-Chartreusin (intermediate No. 505) obtained in Synthesis Example 4 above, after which 31 mg of m-dimethylaminobenzoic acid and 58 mg of dicyclohexycarbodiimide were added, and the resulting mixture was subjected to reaction with stirring at room temperature for 20 hours.

After completion of the reaction, a small amount of methanol was added. Then, the resulting mixture was filtered and the filtrate was concentrated under reduced pressure, after which the oily substance thus obtained was subjected to a silica gel thin-layer chromatography to obtain crystals. Subsequently, said crystals were recrystallized from a mixture of chloroform, ethanol and ether to obtain 73 mg of the desired compound.

SYNTHESIS EXAMPLE 22

Synthesis of the Endo Form of 6-O-(Trans-2-Methyl-2-Butenoyl)-3',4'-O-(m-Trifluoromethylbenzylidene)Chartreusin (Referred to Hereinafter as Compound No. 161)

In a mixture of 4.0 ml of anhydrous pyridine, 3.0 ml of anhydrous ethyl acetate and 5.0 ml of anhydrous chloroform was dissolved 200 mg of the endo form of 3',4'-O-(m-Trifluoromethylbenzylidene)-Chartreusin (intermediate No. 506) obtained in Synthesis Example 5 above, after which 200 mg of tiglic acid and 400 mg of dicyclohexylcarbodiimide were added, and the reaction was carried out with stirring at room temperature for 80 hours.

After completion of the reaction, a small amount of methanol was added. Then, the resulting mixture was filtered and the filtrate was concentrated under reduced pressure, after which the oily substance thus obtained was subjected to a silica gel column chromatography to obtain crystals. Subsequently, said crystals were recrystallized from a mixture of chloroform, ethanol and ether to obtain 64 mg of the desired compound.

SYNTHESIS EXAMPLE 23

Synthesis of the Exo Form of 6-O-(3-Methyl-n-Butyryl)-3',4'-O-Benzylidene-Chartreusin (Referred to Hereinafter as Compound No. 169)

In a mixture of 1.0 ml of anhydrous pyridine, 2.0 ml of anhydrous ethyl acetate and 1.0 ml of anhydrous chloroform was dissolved 40 mg of the exo form of 3',4'-O-Benzylidene-Chartreusin (intermediate No. 501) obtained in Synthesis Example 1 above, after which 0.03 ml of 3-methyl-n-butyric acid and 60 mg of dicyclohexylcarbodiimide were added, and the reaction was carried out with stirring at room temperature for 21 hours.

After completion of the reaction, 28 mg of the desired compound was obtained in the same manner as in Synthesis Example 22 above.

SYNTHESIS EXAMPLE 24

Synthesis of the Exo Form of 6-O-(n-Butyryl)-3',4'-O-Benzylidene-Chartreusin (Referred to Hereinafter as Compound No. 191)

In a mixture of 0.7 ml of anhydrous pyridine, 0.7 ml of anhydrous ethyl acetate and 0.7 ml of anhydrous chloroform was dissolved 50 mg of the exo form of 3',4'-O-Benzylidene-Chartreusin (intermediate No. 501) obtained in Synthesis Example 1 above, after which 0.02 ml of n-butyric acid and 57 mg of dicyclohexylcarbodiimide were added, and the reaction was carried out with stirring at room temperature for 6 hours.

After completion of the reaction, 41 mg of the desired compound was obtained in the same manner as in Synthesis Example 22 above.

SYNTHESIS EXAMPLE 25

Synthesis of the Exo Form of 6-O-(N-Isopropyl-$\beta$-Amino-Isobutyryl)-3',4'-O-Benzylidene-Chartreusin Hydrochloride (Referred to Hereinafter as Compound No. 2)

In a mixture of 1.2 ml of tetrahydrofuran and 0.45 ml of a 0.1N aqueous hydrochloric acid solution was dissolved 40 mg of the exo form of 6-O-(N-Carbobenzyloxy-N-Isopropyl-$\beta$-Amino-isobutyryl)-3',4'-O-benzylidenechartreusin (Referred to Hereinafter as Compound No. 135) obtained by a process according to Synthesis Examples 13 to 24 above, after which 20 mg of 5% palladium-carbon was added, and the resulting mixture was stirred in a hydrogen stream at 0° C. for 1.5 hours. After the stirring, 10 ml of water was added and the resulting mixture was filtered through Celite. The filtrate was washed several times with ethyl acetate and then freeze-dried to obtain 34 mg of the desired compound.

SYNTHESIS EXAMPLE 26

Synthesis of the Exo Form of 6-O-($\beta$-Amino-Isobutyryl)-3',4'-O-Benzylidene-Chartreusin Phosphate (Referred to Hereinafter as Compound No. 6)

In a mixture of 1.9 ml of tetrahydrofuran and 1.9 ml of a 0.1N aqueous phosphoric acid solution was dissolved 60 mg of the exo form of 6-O-(N-Carbobenzyloxy-$\beta$-Amino-Isobutyryl)-3,4-O-Benzylidene-Chartreusin (Referred to Hereinafter as Compound No. 69) obtained by a process according to Synthesis Examples 13 to 24 above, after which 15 mg of 5% palladium-carbon was added, and the resulting mixture was stirred in a hydrogen stream at room temperature for 1 hour. After the stirring, 20 ml of water was added and the resulting mixture was filtered through Celite. The filtrate was washed several times with ethyl acetate and then freeze-dried to obtain 46 mg of the desired compound.

SYNTHESIS EXAMPLE 27

Synthesis of the Exo Form of 6-O-(4-Hydroxy-n-Butyryl)-3',4'-O-Benzylidene-Chartreusin (Referred to Hereinafter as Compound No. 147)

In a mixture of 5.0 ml of tetrahydrofuran and 3.0 ml of methanol was dissolved 35 mg of the exo form of 0 6-O-(4-benzyloxy-n-butyryl)-3',4'-O-Benzylidene-Chartreusin (Referred to Hereinafter as Compound No. 165) obtained by a process according to Synthesis Examples 13 to 24 above, after which 55 mg of 5% palladium-carbon was added, and the resulting mixture was stirred in a hydrogen stream at room temperature for 24 hours.

After the stirring, the mixture was filtered, after which the filtrate was concentrated under reduced pressure and purified by a silica gel thin-layer chromatography to obtain crystals. Subsequently, the crystals were recrystallized from a mixture of chloroform, ethanol and ether to obtain 4 mg of the desired compound.

SYNTHESIS EXAMPLE 28

Synthesis of 6-O-(N-Acetyl-$\beta$-Alanyl)-3',4'-O-Isopropylidene-Chartreusin (Referred to Hereinafter as Compound No. 87)

(1) In a mixture of 3 ml of anhydrous pyridine and 12 ml of anhydrous ethyl acetate was dissolved 474 mg of the 3',4'-O-Isopropylidene-2''-O-tert-butyldimethylsilylchartreusin (intermediate No. 532) obtained in Synthesis Example 9 above, after which 368 mg of N-acetyl-8-alanine and 620 mg of dicyclohexylcarbodiimide were added, and the reaction was carried out with stirring at 25° C. for 20 hours.

After completion of the reaction, the reaction mixture was filtered and the filtrate was concentrated under reduced pressure to obtain an oily substance.

The oily substance was purified by a silica gel column chromatography and then dissolved in a mixture of 12 ml of tetrahydrofuran and 6 ml of 3N hydrochloric acid, and the resulting solution was subjected to reaction at 25° C. for 15 hours.

After completion of the reaction, the reaction mixture was neutralized with an aqueous sodium hydrogencarbonate solution and extracted with chloroform, after which the chloroform layer was dried and the solvent was removed by distillation under reduced pressure to obtain yellow powder of 6-O-(N-acetyl-$\beta$-Alanyl)-Chartreusin (intermediate No. 536).

(2) The aforesaid powder was washed with ether and dissolved in 30 ml of anhydrous chloroform, followed by adding thereto 3.7 ml of 2,2'-dimethoxypropane and 10 mg of p-toluenesulfonic acid, and the resulting mixture was subjected to reaction with stirring at 25° C. for 15 hours.

After completion of the reaction, an aqueous sodium hydrogencarbonate solution was added, and the resulting mixture was extracted with chloroform, after which the chloroform layer was dried and the solvent was removed by distillation under reduced pressure to obtain a crude product.

The crude product was purified by a silica gel thin-layer chromatography to obtain crystals. Subsequently, the crystals were recrystallized from a mixture of chloroform, ethanol and hexane to obtain 355 mg of the desired compound.

SYNTHESIS EXAMPLE 29

Synthesis of 6-O-(3-Cryclohexyl-Propionyl)-3',4'-O-Isopropylidene-Chartreusin (Referred to Hereinafter as Compound No. 240)

(1) In a mixture of 5 ml of anhydrous pyridine, 5 ml of anhydrous chloroform and 5 ml of anhydrous ethyl acetate was dissolved 400 mg of the 3',4'-O-Isopropylidene-2'-O-tert-butyldimethylsilyl-Chartreusin (intermediate No. 532) obtained in Synthesis Example 9 above, after which 0.32 ml of 3-cyclohexylpropionic acid and 620 mg of dicyclohexylcarbodiimide were added, and the reaction was carried out with stirring at 25° C. for 20 hours.

After completion of the reaction, a small amount of methanol was added, after which the resulting mixture was filtered, and the filtrate was concentrated under reduced pressure to obtain an oily substance.

The oily substance was purified by a silica gel column chromatography and then dissolved in a mixture of 10 ml of tetrahydrofuran and 5 ml of 3N hydrochloric acid, and the resulting solution was subjected to reaction at 25° C. for 5 hours.

After completion of the reaction, the reaction mixture was neutralized with an aqueous sodium hydrogencarbonate solution and extracted with chloroform, after which the chloroform layer was dried and the solvent was removed by distillation under reduced pressure to obtain yellow powder of 6-O-(3-cyclohexyl-Propionyl)-Chartreusin (intermediate No. 554).

(2) The aforesaid powder was washed with ether and dissolved in 25 ml of anhydrous chloroform, followed by adding thereto 3.0 ml of 2,2-dimethoxypropane and 10 mg of p-toluenesulfonic acid, and the resulting mixture was subjected to reaction with stirring at 25° C. for 15 hours.

After completion of the reaction, an aqueous sodium hydrogencarbonate solution was added, and the resulting mixture was extracted with chloroform, after which the chloroform layer was dried and the solvent was removed by distillation under reduced pressure to obtain a crude product.

The crude product was purified by a silica gel thin-layer chromatography to obtain crystals. Subsequently, the crystals were recrystallized from a mixture of chloroform, ethanol and ether to obtain 265 mg of the desired compound.

SYNTHESIS EXAMPLE 30

Synthesis of 6-O-(N-Trichloroacetyl-$\beta$-Alanyl)-3',4'-O-Isopropylidene-Chartreusin (Referred to Hereinafter as Compound No. 112)

(1) In a mixture of 0.9 ml of anhydrous pyridine and 3.7 ml of anhydrous ethyl acetate was dissolved 170 mg of the 3',4'-O-Isopropylidene-2'',4''-O-di(tert-butyldimethylsilyl)-Chartreusin (intermediate No. 533) obtained in Synthesis Example 10 above, after which 220 mg of N-trichloroacetyl-$\beta$-alanine and 193 mg of dicyclohexylcarbodiimide were added, and the resulting mixture was subjected to reaction with stirring at 25° C. for 19 hours. After completion of the reaction, the reaction mixture was filtered and the filtrate was concentrated under reduced pressure to obtain an oily substance.

The oily substance was purified by a silica gel column chromatography and then dissolved in a mixture of 3.7 ml of tetrahydrofuran and 1.9 ml of 3N hydrochloric acid, and the resulting solution was subjected to reaction with stirring at 25° C. for 15 hours. After completion of the reaction, the reaction mixture was neutralized with an aqueous sodium hydrogencarbonate solution and extracted with chloroform, after which the chloroform layer was dried and the solvent was removed by distillation under reduced pressure to obtain 128 mg of yellow powder of 6-O-(N-trichloroacetyl-β-alanyl)-chartreusin (intermediate No. 537).

(2) According to Synthesis Example 28 (2) above, 128 mg of the powder was subjected to acetonation to obtain 100 mg of the desired compound.

SYNTHEIS EXAMPLE 31

Synthesis of
6-O-(3,5,5-Trimethyl-n-Hexanoyl)-3',4'-O-Benzylidene-Chartreusin (A Mixture of the Exo Form and the Endo Form at a Ratio of ∼1:1) (Referred to Hereinafter as Compound No. 236)

(1) In a mixture of 4.0 ml of anhydrous pyridine, 4.0 ml of anhydrous chloroform and 15 ml of anhydrous ethyl acetate was dissolved 700 mg of the 3',4'-O-isopropylidene-2'',4''-O-di(tert-butyldimethylsilyl)-obtained in Synthesis Example 10 above, after which 1,220 mg of 3,5,5-trimethyl-n-hexanoic acid and 1,590 mg of dicyclohexylcarbodiimide were added, and the resulting mixture was subjected to reaction with stirring at 25° C. for 100 hours.

After completion of the reaction, the reaction mixture was filtered and the filtrate was concentrated under reduced pressure to obtain an oily substance.

The oily substance was purified by a silica gel column chromatography and then dissolved in a mixture of 20 ml of tetrahydrofuran and 6 ml of 3N hydrochloric acid, and the resulting mixture was subjected to reaction with stirring at 25° C. for 28 hours.

After completion of the reaction, the reaction mixture was neutralized with an aqueous sodium hydrogencarbonate solution and extracted with chloroform, after which the chloroform layer was dried and the solvent was removed by distillation under reduced pressure to obtain 271 mg of yellow powder of 6-O-(3,5,5-trimethyl-m-hexanoyl)chartreusin (intermediate No. 551)

(2) The aforesaid powder (120 mg) was washed with ether and dissolved in 5.0 ml of anhydrous chloroform, followed by adding thereto 1.5 ml of benzaldehyde dimethylacetal and 1 mg of p-toluenesulfonic acid, and the resulting mixture was subjected to reaction with stirring at 25° C. for 8 hours.

After completion of the reaction, purification was conducted in the same manner as in Synthesis Example 29 (2) above to obtain 52 mg of the desired compound.

SYNTHESIS EXAMPLE 32

Synthesis of
6-O-(n-Hexanoyl)-3',4'-O-Benzylidene-Chartreusin (A Mixture of the Exo Form and the Endo Form at a Ratio of ∼1:1) (Referred to Hereinafter as Compound No. 196)

(1) In a mixture of 0.2 ml of anhydrous pyridine and 5.0 ml of anhydrous chloroform was dissolved 572 mg of the 3',4'-O-isopropylidene-2'',4''-O-di(tert-butyldimethylsilyl)-chartreusin (intermediate No. 533) obtained in Synthesis Example 10 above, after which 180 mg of n-hexanoyl chloride was added, and the resulting mixture was subjected to reaction with stirring at 15° C. for 2 hours.

After completion of the reaction, an aqueous sodium hydrogencarbonate solution was added and the resulting mixture was extracted with chloroform. The chloroform layer was washed with water and then with an aqueous sodium chloride solution and was dried, after which the solvent was removed by distillation under reduced pressure to obtain a oily substance.

The oily substance was purified by a silica gel column chromatography and then dissolved in a mixture of 17 ml of tetrahydrofuran and 6 ml of 3N hydrochloric acid, and the resulting solution was subjected to reaction with stirring at 30° C. for 48 hours.

After completion of the reaction, the reaction mixture was neutralized with an aqueous sodium hydrogencarbonate solution and extracted with chloroform, after which the chloroform layer was dried and the solvent was removed by distillation under reduced pressure to obtain 342 mg of yellow powder of 6-O-(n-hexanoyl)-chartreusin (intermediate No. 550).

(2) According to Synthesis Example 31 (2) above, 120 mg of the powder was subjected to benzylidenation to obtain 77 mg of the desired compound.

SYNTHESIS EXAMPLE 33

Synthesis of
6-O-Acetyl-3',4'-O-Isopropylidene-Chartreusin (Referred to Hereinafter as Compound No. 203)

(1) In 0.6 ml of anhydrous pyridine was dissolved 150 mg of the 3',4'-O-isopropylidene-2'',4''-O-di(tert-butyldimethylsilyl)-chartreusin (intermediate No. 533 obtained in Synthesis Example 10 above, after which 0.3 ml of acetic anhydride was added, and the resulting solution was subjected to reaction with stirring at 25° C. for 6 hours.

After completion of the reaction, the reaction mixture was subjected to purification and acid treatment according to Synthesis Example 32 (1) above to obtain 60 mg of yellow powder of 6-O-acetyl-chartreusin (intermediate No. 548).

(2) According to Synthesis Example 28 (2) above, 30 mg of the powder was subjected to acetonation to obtain 20 mg of the desired compound.

SYNTHESIS EXAMPLE 34

Synthesis of
6-O-(3-Cyclohexene-1-Carbonyl)-3',4'-O-Isopropylidene-Chartreusin (Referred to Hereinafter as Compound No. 223)

(1) In a mixture of 1.7 ml of anhydrous pyridine and 1.7 ml of anhydrous chloroform was dissolved 150 mg of the 3',4'-O-isopropylidene-2'',4''-O-di(tert-butyldimetylsilyl)-chartreusin (intermediate No. 533) obtained in Synthesis Example 10 above, after which 0.06 ml of 3-cyclohexene-1-carboxylic acid and 0.07 ml of thionyl chloride were added, and the resulting mixture was subjected to reaction with stirring at 0° C. for 0.2 hour.

After completion of the reaction, the reaction mixture was subjected to purification and acid treatment according to Synthesis Example 32 (1) above to obtain 123 mg of yellow powder of 6-O-(3-cyclohexene-1-carbonyl)-chartreusin (intermediate No. 556).

(2) According to Synthesis Example 28 (2) above, 123 mg of the powder was subjected to acetonation to obtain 66 mg of the desired compound.

The amino acid, the amino acid derivatives, the carboxylic acid and the carboxylic acid derivatives of the general formula (VII) are easily available or can be synthesized by a conventional process. Examples of processes for the synthesis of these compounds which are used as materials for preparing compound No. 1 to compound No. 250 which are hereinafter mentioned are described below.

SYNTHESIS EXAMPLE 35

Synthesis of β-(1-Pyrrolidinyl)-Propionic Acid (Used for Preparing Compound No. 9 and Compound No. 34)

In 5 ml of absolute methanol were dissolved 500 mg of acrylic acid and 800 mg of pyrrolidine, and the resulting solution was subjected to reaction with stirring at room temperature for 24 hours.

After completion of the reaction, the methanol and the unreacted pyrrolidine were removed under reduced pressure, after which water was added to the residue and the resulting aqueous solution was adjusted to pH 9 to 10 with an aqueous sodium hydroxide solution. The aqueous solution thus adjusted was washed with ethyl acetate and then adjusted to pH 1 to 2 with hydrochloric acid. The acidic aqueous solution thus obtained was washed with ethyl acetate and then adjusted to pH 6.0 again with an aqueous sodium hydroxide solution. Subsequently, the weakly acidic aqueous solution thus obtained was filtered, after which the filtrate was concentrated under reduced pressure to remove water, whereby white powder was obtained. The white powder was dissolved in a mixture of ethanol and a small amount of water, and the resulting solution was filtered, after which the filtrate was concentrated under reduced pressure to obtain 280 mg of the desired compound.

NMR (60 MHz, δ values in CD$_3$OD): 2.08 (4H, m, —CH$_2$—CH$_2$—), 2.54 (2H, t, J=6 Hz, —COCH$_2$—),

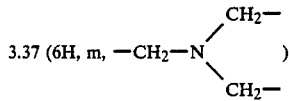

The following amino acid derivative was synthesized according to Synthesis Example 35 above:

β-Morpholino-propionic acid (used for preparing compound No. 32)

NMR (60 MHz, δ values in CD$_3$OD): 2.45 (2H, t, J=6 Hz, —COCH$_2$—)

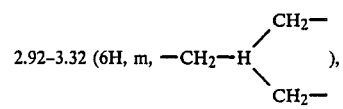

3.83 (4H, m, —CH$_2$OCH$_2$—)

SYNTHESIS EXAMPLE 36

Synthesis of N-Trifluoroacetyl-β-Amino-Isobutyric Acid (Used for Preparing Compound Nos. 12, 30, 37, 44 and 68)

To 2.0 ml of trifluoroacetic anhydride was added 300 mg of β-amino-isobutyric acid in small portions, and the resulting mixture was stirred at 0° C. for 30 minutes and then subjected to reaction with stirring at room temperature for 3 hours.

After completion of the reaction, the unreacted trifluoroacetic anhydride was removed under reduced pressure, after which water was added to the residue and the resulting mixture was extracted with ethyl acetate. The ethyl acetate layer obtained was washed with an aqueous sodium chloride solution, dried, and then concentrated under reduced pressure to obtain a white crude product. Subsequently, the crude product was washed with a mixed solvent of hexane and ether and then dried to obtain 480 mg of the desired compound having a melting point of 61.0°–65.0° C.

NMR (60 MHz, δ values in CDCl$_3$): 1.25 (3H, d, J=7 Hz, CH$_3$), 2.80 (1H, m, —CH—), 3.53 (2H, t, J=7 Hz, —CH$_2$—N—), 7.47 (1H, m, —NH—), 10 97 (1H, s, —COOH)

The following amino acid derivatives were synthesized according to Synthesis Example 36 above:

N-trifluoroacetyl-6-alanine (used for preparing compound Nos. 21, 28, 31, 41, 49, 100 and 132) m.p. 115.0°–120.0° C.

N-trifluoroacetyl-β-amino-n-butyric acid (used for preparing compound Nos. 39, 51 and 94) m.p. 126.0°–130.0° C.

N-trifluoroacetyl-β-amino-n-caproic acid (used for preparing compound Nos. 97, 98 and 130) m.p. 88.0°–90.0° C.

N-trifluoroacetyl-8-amino-n-caprylic acid (used for preparing compound Nos. 64, 77 and 99) m.p. 58.0°–61.0° C.

N-trifluoroacetyl-5-amino-n-valeric acid (used for preparing compound No. 43) m.p. 89.0°–92.0° C.

N-methyl-N-trifluoroacetyl-glycine (used for preparing compound Nos. 25, 67, 82 and 86)

NMR (60 MHz, δ values in CDCl$_3$): 3.22(3H, s, N—CH$_3$), 4.17(2H, s, —CO—CH$_2$—N—), 10.47(1H, s, —COOH)

N-trifluoroacetyl-4-amino-n-butyric acid (used for preparing compound Nos. 24, 57 and 91)

NMR (60 MHz, δ values in CDCl$_3$): 2.00(2H, m, —CH$_2$—), 2.32(2H, t, J=7 Hz, —CO—CH$_2$—), 3.22–3.62(2H, m, —CH$_2$—N—)

N-trifluoroacetyl-2-amino-cyclohexanecarboxylic acid (used for preparing compound Nos. 26, 27, 117 and 118)

NMR (60 MHz, δ values in CDCl$_3$) 1.14–2.17(8H, m, CH$_2$×4), 2.91(1H, m, —CH—CO—), 4.11(1H, m, —CH—N—)

SYNTHESIS EXAMPLE 37

Synthesis of N-trichloroacetyl-β-alanine (used for preparing compound Nos. 22, 56 and 112)

To 5.6 ml of anhydrous chloroform was added 500 mg of β-alanine, and 1.3 ml of trichloroacetyl chloride was dropped thereinto with stirring at 0° C. After completion of the dropping, the resulting mixture was subjected to reaction with stirring at room temperature for 5 hours.

After completion of the reaction, water was added and the mixture thus obtained was extracted with ethyl acetate. The ethyl acetate layer obtained was washed with an aqueous sodium chloride solution and then concentrated to obtain an oily substance. The oily substance was recrystallized from a mixed solvent of ethyl acetate and hexane to obtain 270 mg of the desired compound having a melting point of 102.0°–110.5° C.

The following amino acid derivative was synthesized according to Synthesis Example 37 above.

N-benzoyl-β-amino-isobutyric acid (used for preparing compound No. 13)

SYNTHESIS EXAMPLE 38

Synthesis of N-carbobenzyloxy-β-amino-isobutyric acid (used for preparing the compound No. 60)

In a mixture of 10 ml of pyridine and 10 ml of water was dissolved 500 mg of β-amino-isobutyric acid, and 1.5 ml of benzyloxycarbonyl chloride was dropped thereinto with stirring at 0° C. After completion of the dropping, the resulting mixture was stirred at room temperature for 3 hours, after which the pyridine was removed under reduced pressure. Then, hydrochloric acid was added to the residue, and the resulting mixture was extracted with ethyl acetate. The ethyl acetate layer obtained was washed successively with diluted hydrochloric acid, water and an aqueous sodium chloride solution, and then concentrated to obtain an oily substance. Subsequently, the oily substance was washed with a mixed solvent of ether and hexane to obtain 380 mg of the desired com- pound.

NMR (60 MHz, δ values in $CDCl_3$): 1.17(3H, d, J=7 Hz, $CH_3$), 2.69(1H, m, —CH—), 3.36(2H, t, J=7 Hz, —$CH_2$—N—), 5.11(2H, s, benzyl proton), 7.30(5H, s, aromatic proton), 9.97(1H, s, —COOH)

The following amino acid derivatives were synthesized according to Synthesis Example 38 above:

N-carbobenzyloxy-6-amino-n-caproic acid (used for preparing compound Nos. 110, 111 and 119) m.p. 54.0°–56.0° C.

N-carbobenzyloxy-N-isopropyl-β-amino-isobutyric acid (used for preparing compound No. 135)

NMR (60 MHz, δ values in $CDCl_3$): 1.10(3H×3, d, J=7 Hz, $CH_3$×3), 5.08(2H, s, benzyl proton), 7.25(5H, aromatic proton)

N-carbobenzyloxy-2-amino-cyclohexanecarboxylic acid (used for preparing compound No. 62)

NMR (60 MHz, δ values in $CDCl_3$): 1.11–2.17(8H, m, $CH_2$×4), 2.34–2.91(1H, m, —CH—CO—), 3.84–4.27(1H, m, —CH—N<), 4.97–5.21(2H, benzyl proton), 6.91(1H, s, —NH—CO—), 7.27(5H, s, aromatic proton), 10.57(1H, s, —COOH)

SYNTHESIS EXAMPLE 39

Synthesis of N-carbobenzyloxy-α-isopropyl-β-alanine (used for preparing compound Nos. 70, 105 and 125)

(1) In 20 ml of absolute methanol was dissolved 520 mg of metallic sodium, and 2.12 g of ethyl cyanoacetate was added thereto with stirring at room temperature, after which 4.0 g of isopropyl iodide was added dropwise over a period of 10 minutes. After completion of the dropwise addition, the resulting mixture was stirred at room temperature for 3 hours, refluxed for 1 hour, subjected to a conventional post-treatment, and then distilled under reduced pressure to obtain 2.1 g of methyl α-isopropylcyanoacetate.

NMR (60 MHz, δ value in $CDCl_3$): 1.10(3H, d, J=7 Hz, $CH_3$), 1.13(3H, d, J=7 Hz, $CH_3$), 2.37(1H, m, CH), 3.46(1H, d, J=6 Hz, CH), 3.81(3H, s, —$COOCH_3$)

(2) In 6.0 ml of acetic acid was dissolved 560 mg of the methyl α-isopropyl-cyanoacetate obtained in (1) above, after which 0.15 ml of concentrated sulfuric acid and 50 mg of platinum oxide (Adams catalyst) were added, and the resulting mixture was subjected to catalytic reduction in a hydrogen stream at 3 to 4 atmospheres for 4 hours.

After completion of the reaction, the reaction mixture was filtered. Then, water was added to the filtrate and the resulting mixture was concentrated under reduced pressure, after which the acetic acid was removed to obtain an oily substance. Subsequently, the oily substance was dissolved in water, and the resulting solution was neutralized with about 0.1N barium hydroxide and then filtered, after which the filtrate was concentrated under reduced pressure to obtain 570 mg of crude methyl ester of α-isopropyl-β-alanine.

(3) The crude methyl ester of α-isopropyl-β-alanine obtained in (2) above was treated according to Synthesis Example 38 above to obtain methyl ester of N-carbobenzyloxy-α-isopropyl-β-alanine.

NMR (60 MHz, δ values in $CDCl_3$): 0.94(3H×2, d, J=7 Hz, $CH_3$×2), 3.65(3H, s, —$COOCH_3$), 5.05(2H, s, benzyl proton), 7.28(5H s, aromatic proton)

(4) In a mixture of 18 ml of methanol and 2.7 ml of a 2N aqueous potassium hydroxide solution was dissolved 450 mg of the methyl ester of N-carbobenzyloxy-α-isopropyl-β-alanine obtained in (3) above, and the resulting solution was stirred at 40° to 50° C. for 5 hours.

After completion of the reaction, the reaction mixture was neutralized with hydrochloric acid, after which the methanol was removed under reduced pressure, and the residue was acidified with diluted hydrochloric acid and then extracted with ethyl acetate. The ethyl acetate layer was washed with water and then with an aqueous sodium chloride solution, thereafter dried, and then concentrated under reduced pressure to obtain crude crystals. The crude crystals were recrystallized from a mixture of ethyl acetate and hexane to obtain 310 mg of the desired compound having a melting point of 75.5°–78.5° C.

NMR (60 MHz, δ values in $CDCl_3$): 0.96(3H×2, d, J=7 Hz, $CH_3$×2), 5.05(2H, s, benzyl proton), 7.26(5H, s, aromatic proton), 10.69(1H, s, —COOH)

SYNTHESIS EXAMPLE 40

Synthesis of 3-Chloropropionyloxyacetic Acid (Used for Preparing Compound No. 149)

In a mixture of 5.0 ml of anhydrous pyridine and 3.0 ml of anhydrous chloroform was dissolved 2.0 g of glycolic acid, and 2.5 ml of 3-chloropropionyl chloride was added dropwise at 0° C. After completion of the dropwise addition, the resulting mixture was subjected to reaction with stirring at 30° to 35° C. for 2 hours.

After completion of the reaction, the reaction mixture was added to 300 ml of a saturated aqueous sodium chloride solution, and the resulting mixture was extracted with ethyl acetate. The ethyl acetate layer was dried, after which the solvent was removed by distillation under reduced pressure to obtain 2.8 g of the desired compound.

NMR (60 MHz, δ values in $CDCl_3$): 2.89(2H, t, J=6 Hz, —$CH_2$—CO—), 3.73(2H, t, J=6 Hz, —$CH_2$—Cl), 4.66(2H, s, —O—$CH_2$—CO—), 10.8(1H, s, —COOH

SYNTHESIS EXAMPLE 41

Synthesis of 3-Methylsulfinyl-Propionic Acid (Used for Preparing Compound Nos. 150 and 152)

In 50 ml of water was dissolved 5.4 g of sodium metaperiodate, and 3.0 g of 3-methylthiopropionic acid was added dropwise at 1° to 3° C. over a period of 20 minutes. After completion of the dropwise addition, the resulting mixture was subjected to reaction with stirring at 1° to 3° C. for 2 hours After completion of the reaction, the reaction mixture was filtered and the filtrate was concentrated under reduced pressure to obtain a solid. Subsequently, the solid was dissolved in 30 ml of ethanol, followed by adding thereto 3.0 g of anhydrous sodium sulfate, and the resulting mixture was stirred at room temperature for 2 hours, after which the mixture was filtered and the filtrate was concentrated under reduced pressure to obtain 3.2 g of the desired product.

NMR (60 MHz, δ values in CD$_3$OD): 2.63(3H, s, CH$_3$SO—), 2.81 (2H, t, J=4 Hz, —CH$_2$—CO—), 2.96(2H, t, J=4 Hz, —CH$_2$—SO—)

SYNTHESIS EXAMPLE 42

Synthesis of N,N-Dimethyl-β-Amino-Isobutyric Acid (Used for Preparing Compound No. 1)

In 1.0 ml of water was dissolved 1.5 g of methyl malonate, after which 1.26 g of a 50% aqueous dimethylamine solution and 0.96 ml of a 37% aqueous formaldehyde solution were added with stirring at 0° C., and the resulting mixture was stirred at 0° to 5° C. for 3 hours and then at 80° C. for 30 minutes.

After completion of the reaction, the solvent was removed under reduced pressure, after which anhydrous sodium sulfate was added to the residue, and the resulting mixture was extracted with methanol. The methanol solution thus obtained was filtered and then concentrated under reduced pressure to obtain a white solid. The solid was recrystallized from a mixture of methanol and acetone to obtain 610 mg of the desired compound having a melting point of 169.0°-174.0° C.

NMR (60 MHz, δ values in D$_2$O, internal standard; DSS):

1.14(3H, d, J=7Hz, CH$_3$), 2.86(3H×2, s, CH$_3$—N—CH$_3$), 2.98(1H, d, J=10Hz, —CH—N⟨ ), 3.21(1H, d, J=10Hz,

—CH—N⟨ )

The following amino acids were synthesized according to Synthesis Example 42 above:

N,N-dimethyl-2-ethyl-β-alanine (used for preparing compound No. 134)

NMR (60 MHz, δ values in CDCl$_3$):

0.96(3H, t, J=7Hz, CH$_3$), 1.45-1.88(2H, m, —CH$_2$—),

-continued 2.69(3H×2, s, CH$_3$—N—CH$_3$), 2.87(1H, d, J=11Hz,

—CH—N⟨ ), 3.26(1H, d, J=11Hz, —CH—N⟨ )

N-isopropyl-β-amino-isobutyric acid (used for preparing N-carbobenzyloxy-N-isopropyl-β-aminoisobutyric acid) m.p. 175.5°-176.0° C.

SYNTHESIS EXAMPLE 43

Synthesis of N-(N′,N′-Dimethyl-Glycyl)-β-Amino-Isobutyric Acid (Used for Preparing Compound No. 4)

(1) In a mixture of 3.0 ml of dioxane and 3.0 ml of pyridine was dissolved 103 mg of N,N-dimethylglycine and 117 mg of methyl β-amino-isobutyrate, followed by adding thereto 227 mg of dicyclohexylcarbodiimide, and the resulting mixture was subjected to reaction with stirring at room temperature for 24 hours.

After completion of the reaction, the reaction mixture was filtered and the filtrate was concentrated under reduced pressure, after which the concentrate was dissolved in a small amount of water, and only the soluble fraction was concentrated under reduced pressure and dissolved in a small amount of methanol. Only the soluble fraction thus obtained was concentrated under reduced pressure to obtain 186 mg of crude methyl N-(N′,N′-dimethyl-glycyl)-β-amino-isobutyrate.

(2) In a mixture of 1.0 ml of methanol and 1.0 ml of a 1.2N aqueous sodium hydroxide solution was dissolved 186 mg of the methyl ester, and the resulting solution was subjected to reaction with stirring at room temperature for 1 hour.

After completion of the reaction, the reaction mixture was neutralized with diluted hydrochloric acid and then subjected to post-treatment in the same manner as in (1) above to obtain 211 mg of crude N-(N′,N′-dimethylglycyl)-β-amino-isobutyric acid.

The following amino acid derivative was synthesized according to Synthesis Example 43 above:

N-(N′-carbobenzyloxy-glycyl)-β-amino-isobutyric acid (used for preparing compound No. 74)

NMR (60 MHz, δ values in CD$_3$Cl$_3$—CD$_3$OD): 1.13(3H, d, J=7 Hz, CH$_3$), 5.05(2H, s, benzyl proton), 7.27(5H, aromatic proton)

Specific examples of the compounds included in this invention are described in Table 5.

TABLE 5

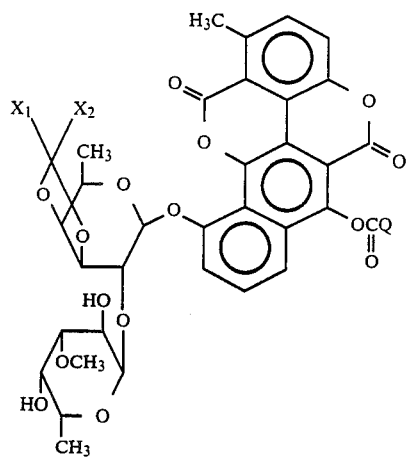
(I)

| Compound No. | $X_1$ | $X_2$ | Isomer[2] | $Q^{[1]}$ | Salt | Melting point (°C.) |
|---|---|---|---|---|---|---|
| 1 | H | Phenyl | Exo | $-CH(CH_3)CH_2N(CH_3)_2$ | HCl | 126.5–136.0 |
| 2 | H | Phenyl | Exo | $-CH(CH_3)CH_2NHCH(CH_3)_2$ | HCl | 160.0–165.0 |
| 3 | H | Phenyl | Exo | $-CH(CH_3)CH_2NHCOCH_2NH_2$ | $H_3PO_4$ | 152.0–156.0 |
| 4 | H | Phenyl | Exo | $-CH(CH_3)CH_2NNCOCH_2N(CH_3)_2$ | HCl | 160.5–163.0 |
| 5 | H | Phenyl | Exo | $-CH(CH_3)CH_2-(1\text{-aziridinyl})$ | HCl | — |
| 6 | H | Phenyl | Exo | $-CH(CH_3)CH_2NH_2$ | $H_3PO_4$ | 152.0–158.0 |
| 7 | H | Phenyl | Exo | $-CH(CH_2CH_3)CH_2-(1\text{-aziridinyl})$ | HCl | — |
| 8 | H | Phenyl | Exo | $-(CH_2)_2-N(C_2H_5)_2$ | HCl | 142.0–148.5 |
| 9 | H | Phenyl | Exo | $-(CH_2)_2-(1\text{-pyrrolidinyl})$ | HCl | 154.5–160.0 |
| 10 | H | Phenyl | Exo | $-(CH_2)_2NHCOCH_2NH_2$ | $H_3PO_4$ | 152.5–158.0 |
| 11 | H | Phenyl | Exo | $-CH_2NHCOCH_2NHCOCH_2NH_2$ | $H_3PO_4$ | 176.0–184.5 |
| 12 | H | Phenyl | Exo | $-CH(CH_3)CH_2NHCOCF_3$ | — | 163.0–173.0 |

TABLE 5-continued

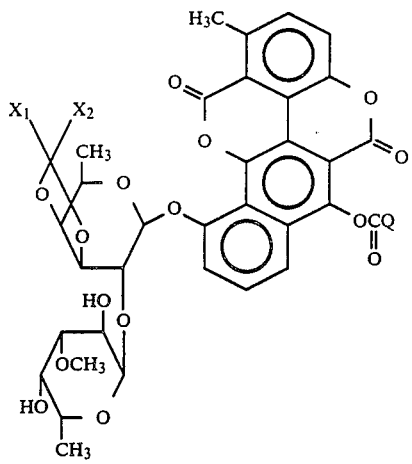

(I)

| Compound No. | $X_1$ | $X_2$ | Isomer[2] | $Q^{[1]}$ | Salt | Melting point (°C.) |
|---|---|---|---|---|---|---|
| 13 | H | Phenyl | Exo | −CH(CH₃)CH₂NHCO(phenyl) | — | 158.0–167.0 |
| 14 | H | m-Fluorophenyl | Exo | −CH(CH₃)CH₂NH₂ | H₃PO₄ | 160.0–164.0 |
| 15 | H | m-Fluorophenyl | Exo | −(CH₂)₂N(C₂H₅)₂ | HCl | 142.5–149.5 |
| 16 | H | m-Fluorophenyl | Exo | −(CH₂)₂NH₂ | H₃PO₄ | 145.0–152.5 |
| 17 | H | Phenyl | Exo | −(CH₂)₂NH₂ | HCl | 170.5–174.5 |
| 18 | H | Phenyl | Exo | −(CH₂)₂NH₂ | ½ H₃PO₄ | 163.5–167.0 |
| 19 | H | Phenyl | Exo | −(CH₂)₅NH₂ | HCl | 155.0–159.5 |
| 20 | H | Phenyl | Exo | −(CH₂)₂NHCHO | — | 160.0–172.0 |
| 21 | H | Phenyl | Exo | −(CH₂)₂NHCOCF₃ | — | 169.0–175.0 |
| 22 | H | Phenyl | Exo | −(CH₂)₂NHCOCCl₃ | — | 165.0–173.0 |
| 23 | H | Phenyl | Exo | −(CH₂)₂NHCO(phenyl) | — | 160.0–165.0 |
| 24 | H | Phenyl | Exo | −(CH₂)₃NHCOCF₃ | — | 172.0–185.0 |
| 25 | H | Phenyl | Exo | −CH₂N(CH₃)COCF₃ | — | 165.0–174.0 |
| 26 | H | Phenyl | Exo | −CH−(CH₂)₄−CH−NHCOCF₃ | — | 162.0–171.0 |
| 27 | H | m-Fluorophenyl | Exo | −CH−(CH₂)₄−CH−NHCOCF₃ | — | 179.0–186.0 |
| 28 | H | Phenyl | Endo | −(CH₂)₂NHCOCF₃ | — | 151.5–156.5 |
| 29 | H | Phenyl | Endo | −(CH₂)₂NHCOCH₃ | — | 150.5–157.5 |
| 30 | H | m-Trifluoromethylphenyl | Endo | −CH(CH₃)CH₂NHCOCF₃ | — | 144.0–150.0 |
| 31 | H | m-Bromophenyl | Endo | −(CH₂)₂NHCOCF₃ | — | 145.0–152.0 |
| 32 | H | Phenyl | Exo | −(CH₂)₂−N[(CH₂)₂O(CH₂)₂] | HCl | 152.0–159.5 |
| 33 | H | m-Fluorophenyl | Exo | −(CH₂)₂NHCOCH₂NH₂ | H₃PO₄ | 154.5–164.0 |

TABLE 5-continued

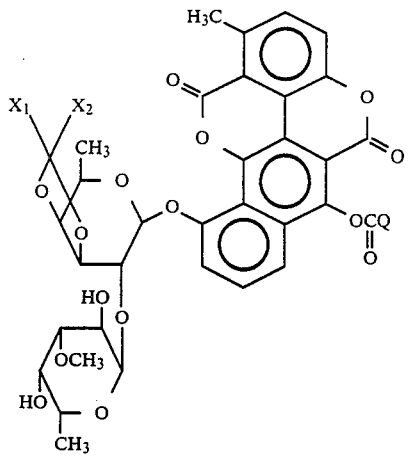

(I)

| Compound No. | $X_1$ | $X_2$ | Isomer[2] | $Q^{[1]}$ | Salt | Melting point (°C.) |
|---|---|---|---|---|---|---|
| 34 | H | m-Fluorophenyl | Exo | —(CH$_2$)$_2$—(1-pyrrolidinyl) | H$_3$PO$_4$ | 108.0–120.5 |
| 35 | H | Phenyl | Exo | —CH(CH(CH$_3$)$_2$)CH$_2$NH$_2$ | H$_3$PO$_4$ | 153.0–160.0 |
| 36 | H | Phenyl | Exo | —CH(CH(CH$_3$)$_2$)NHCOCH$_2$NHCOCH$_2$NH$_2$ | H$_3$PO$_4$ | 150.0–157.0 |
| 37 | H | m-Fluorophenyl | Exo | —CH(CH$_3$)CH$_2$NHCOCF$_3$ | — | 169.5–175.0 |
| 38 | H | Phenyl | Exo | —(CH$_2$)$_2$NHCOCH$_3$ | — | 162.0–176.0 |
| 39 | H | Phenyl | Exo | —CH$_2$CH(CH$_3$)NHCOCF$_3$ | — | 184.0–193.0 |
| 40 | H | Phenyl | Mixture (1:1) | —(CH$_2$)$_2$NHCHO | — | 162.0–169.5 |
| 41 | H | Phenyl | Mixture (1:1) | —(CH$_2$)$_2$NHCOCF$_3$ | — | 158.0–163.0 |
| 42 | CH$_3$ | CH$_3$ | — | —(CH$_2$)$_2$NH$_2$ | HCl | 162.0–167.0 |
| 43 | H | Phenyl | Exo | —(CH$_2$)$_4$NHCOCF$_3$ | — | 176.0–186.0 |
| 44 | H | Phenyl | Endo | —CH(CH$_3$)CH$_2$NHCOCF$_3$ | — | 152.0–156.5 |
| 45 | H | Phenyl | Endo | —(CH$_2$)$_2$NHCHO | — | 150.0–159.0 |
| 46 | H | m-Fluorophenyl | Endo | —(CH$_2$)$_2$NHCHO | — | 157.0–167.0 |
| 47 | H | m-Fluorophenyl | Endo | —(CH$_2$)$_2$NHCO(phenyl) | — | 156.0–165.0 |
| 48 | CH$_3$ | CH$_3$ | — | —(CH$_2$)$_2$NHCHO | — | 160.0–162.0 |
| 49 | CH$_3$ | CH$_3$ | — | —(CH$_2$)$_2$NHCOCF$_3$ | — | 155.0–159.0 |
| 50 | CH$_3$ | CH$_3$ | — | —(CH$_2$)$_2$NHCO(phenyl) | — | 146.0–149.0 |
| 51 | CH$_3$ | CH$_3$ | — | —CH$_2$CH(CH$_3$)NHCOCF$_3$ | — | 157.5–164.5 |
| 52 | H | m-Trifluoromethylphenyl | Endo | —(CH$_2$)$_2$NHCHO | — | 160.0–167.0 |
| 53 | H | m-Trifluoromethylphenyl | Endo | —(CH$_2$)$_2$NHCOCH$_3$ | — | 149.0–153.0 |
| 54 | H | m-Bromophenyl | Endo | —(CH$_2$)$_2$NHCHO | — | 160.0–166.0 |
| 55 | H | o-Methylphenyl | Exo | —(CH$_2$)$_2$NHCHO | — | 159.0–165.0 |
| 56 | H | m-Bromophenyl | Endo | —(CH$_2$)$_2$NHCOCCl$_3$ | — | 148.0–156.0 |
| 57 | H | p-Fluorophenyl | Endo | —(CH$_2$)$_3$NHCOCF$_3$ | — | 150.5–156.0 |

TABLE 5-continued

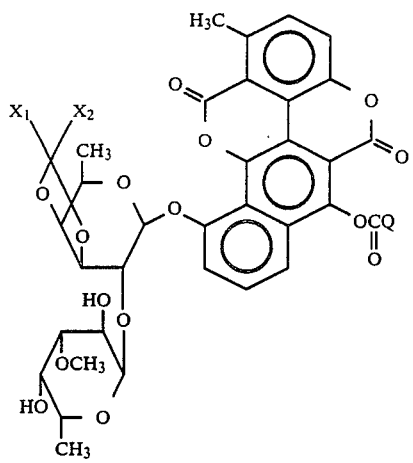

(I)

| Compound No. | $X_1$ | $X_2$ | Isomer[2] | $Q^{(1)}$ | Salt | Melting point (°C.) |
|---|---|---|---|---|---|---|
| 58 | H | o-Chlorophenyl | Endo | —(CH$_2$)$_2$NHCHO | — | 164.0–168.0 |
| 59 | CH$_3$ | CH$_3$ | — | —(CH$_2$)$_5$NH$_2$ | CH$_3$COOH | 152.5–159.0 |
| 60 | H | m-Fluorophenyl | Exo | —CH(CH$_3$)(CH$_2$NHCOOCH$_2$(phenyl)) | — | 175.0–184.0 |
| 61 | H | m-Fluorophenyl | Exo | —(CH$_2$)$_2$NHCOCH$_2$NHCOOCH$_2$(phenyl) | — | 143.0–148.0 |
| 62 | H | Phenyl | Exo | —CH—(CH$_2$)$_4$—CH—NHCOOCH$_2$(phenyl) | — | 156.0–165.0 |
| 63 | CH$_3$ | CH$_3$ | — | —CH(CH$_2$CH$_2$SCH$_3$)(NHCOOCH$_2$(phenyl)) | — | 140.0–144.0 |
| 64 | H | m-Fluorophenyl | Endo | —(CH$_2$)$_7$NHCOCF$_3$ | — | 113.0–120.0 |
| 65 | H | Phenyl | Endo | —(CH$_2$)$_2$NHCO(phenyl) | — | 148.5–157.0 |
| 66 | H | Phenyl | Endo | —CH$_2$CH(CH$_3$)(NHCOCF$_3$) | — | 156.0–164.5 |
| 67 | H | Phenyl | Endo | —CH$_2$N(CH$_3$)(COCF$_3$) | — | 156.5–164.0 |
| 68 | H | m-Fluorophenyl | Endo | —CH(CH$_3$)(CH$_2$NHCOCF$_3$) | — | 145.0–154.0 |
| 69 | H | Phenyl | Exo | —CH(CH$_3$)(CH$_2$NHCOOCH$_2$(phenyl)) | — | 160.0–167.0 |
| 70 | H | Phenyl | Exo | —CH(CH(CH$_3$)$_2$)(CH$_2$NHCOOCH$_2$(phenyl)) | — | 175.0–185.0 |
| 71 | H | Phenyl | Exo | —CH$_2$NHCOOCH$_2$(phenyl) | — | 176.0–183.0 |
| 72 | H | Phenyl | Exo | —(CH$_2$)$_2$NHCOOCH$_2$(phenyl) | — | 155.5–165.0 |
| 73 | H | m-Fluorophenyl | Exo | —(CH$_2$)$_2$NHCOOCH$_2$(phenyl) | — | 152.0–161.0 |

TABLE 5-continued

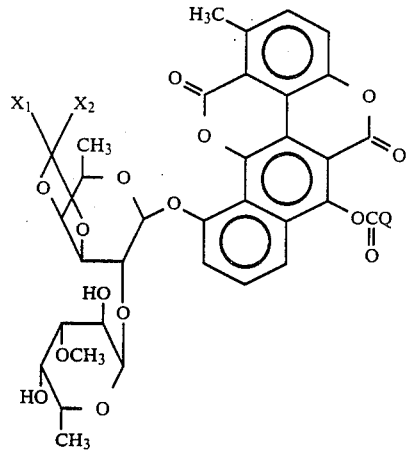

(I)

| Compound No. | $X_1$ | $X_2$ | Isomer[2] | $Q^{[1]}$ | Salt | Melting point (°C.) |
|---|---|---|---|---|---|---|
| 74 | H | Phenyl | Exo | $-CH\begin{matrix}CH_3\\CH_2NHCOCH_2NH\\ \|\\(phenyl)CH_2OOC\end{matrix}$ | — | 129.5–139.0 |
| 75 | H | Phenyl | Exo | $-(CH_2)_2NHCOCH_2NH$<br>$\|$<br>$(phenyl)CH_2OOC$ | — | 148.0–153.0 |
| 76 | H | Phenyl | Exo | $-(CH_2)_3NHCOOCH_2(phenyl)$ | — | 156.0–167.0 |
| 77 | H | Phenyl | Exo | $-(CH_2)_7NHCOCF_3$ | — | 173.0–181.0 |
| 78 | H | Phenyl | Mixture (1:1) | $-(CH_2)_5NHCOCF_3$ | — | 143.0–149.0 |
| 79 | H | Phenyl | Exo | $-CH\begin{matrix}CH_2CH_2SOCH_3\\NHCOOCH_2(phenyl)\end{matrix}$ | — | 165.0–176.0 |
| 80 | H | Phenyl | Endo | $-(CH_2)_2NH_2$ | HCl | 166.5–170.0 |
| 81 | H | 3-Thienyl | Exo | $-(CH_2)_2NHCHO$ | — | 171.0–180.0 |
| 82 | H | o-Fluorophenyl | Mixture (1:5) | $-CH_2N\begin{matrix}CH_3\\COCF_3\end{matrix}$ | — | 157.5–167.0 |
| 83 | H | 2-Phenylethyl | Exo | $-(CH_2)_2NHCHO$ | — | 160.0–172.0 |
| 84 | H | 2-Furyl | Mixture (1:1) | $-(CH_2)_2NHCHO$ | — | 160.0–169.0 |
| 85 | $CH_3$ | $CH_3$ | — | $-CH\begin{matrix}CH_3\\CH_2NHCOCF_3\end{matrix}$ | — | 147.5–153.0 |
| 86 | $CH_3$ | $CH_3$ | — | $-CH_2N\begin{matrix}CH_3\\COCF_3\end{matrix}$ | — | 174.0–180.0 |
| 87 | $CH_3$ | $CH_3$ | — | $-(CH_2)_2NHCOCH_3$ | — | 153.0–156.5 |
| 88 | $CH_3$ | $CH_3$ | — | $-CH_2NHCO(phenyl)$ | — | 160.5–164.0 |
| 89 | H | 3-Thienyl | Endo | $-(CH_2)_2NHCHO$ | — | 172.0–177.0 |
| 90 | H | m-Chlorophenyl | Exo | $-(CH_2)_2NHCHO$ | — | 170.0–179.0 |
| 91 | H | p-Fluorophenyl | Exo | $-(CH_2)_3NHCOCF_3$ | — | 188.5–196.0 |
| 92 | H | p-Fluorophenyl | Exo | $-(CH_2)_2NHCHO$ | — | 183.5–189.5 |
| 93 | H | 2,4-Dichlorophenyl | Endo | $-(CH_2)_2NHCHO$ | — | 175.0–182.0 |
| 94 | H | o-Chlorophenyl | Endo | $-CH_2CH\begin{matrix}CH_3\\NHCOCF_3\end{matrix}$ | — | 162.0–165.0 |

TABLE 5-continued

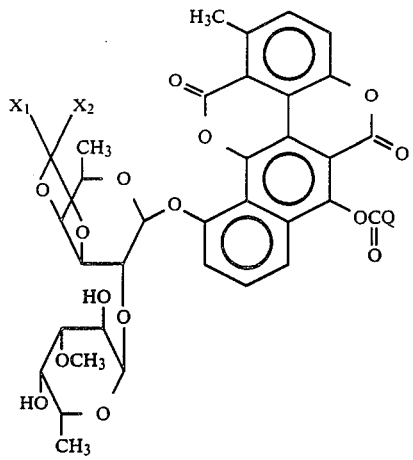
(I)

| Compound No. | $X_1$ | $X_2$ | Isomer[2] | $Q^{(1)}$ | Salt | Melting point (°C.) |
|---|---|---|---|---|---|---|
| 95 | H | p-Methoxyphenyl | Exo | $-(CH_2)_2NHCHO$ | — | 165.0–173.0 |
| 96 | H | p-Methoxyphenyl | Exo | $-(CH_2)_2NHCO(phenyl)$ | — | 174.0–182.0 |
| 97 | H | p-Fluorophenyl | Exo | $-(CH_2)_5NHCOCF_3$ | — | 188.0–193.0 |
| 98 | $CH_3$ | $CH_3$ | — | $-(CH_2)_5NHCOCF_3$ | — | 193.0–197.5 |
| 99 | $CH_3$ | $CH_3$ | — | $-(CH_2)_7NHCOCF_3$ | — | 167.0–173.5 |
| 100 | H | $CH_2CH_3$ | — | $-(CH_2)_2NHCOCF_3$ | — | 145.0–153.5 |
| 101 | H | m-Trifluoromethylphenyl | Endo | $-CH\diagup^{CH_2-(3-indolyl)}_{\diagdown NHCOOCH_2(phenyl)}$ | — | 155.0–164.0 |
| 102 | $CH_3$ | $CH_3$ | — | $-CH\diagup^{CH_2CH_2SOCH_3}_{\diagdown NHCOOCH_2(phenyl)}$ | — | 153.0–161.0 |
| 103 | H | Phenyl | Endo | $-(CH_2)_2NHCOOCH_2(phenyl)$ | — | 132.0–140.0 |
| 104 | H | Phenyl | Endo | $-CH_2NHCOOCH_2(phenyl)$ | — | 150.0–154.0 |
| 105 | H | o-Chlorophenyl | Endo | $-CH\diagup^{CH(CH_3)_2}_{\diagdown NHCOOCH_2(phenyl)}$ | — | 152.0–159.0 |
| 106 | H | Phenyl | Exo | $-CH\diagup^{CH(CH_3)_2}_{\diagdown NHCOOCH_2(phenyl)}$ | — | 182.0–189.0 |
| 107 | $CH_3$ | $CH_3$ | — | $-(CH_2)_2NHCOOCH_2(phenyl)$ | — | 133.0–137.5 |
| 108 | $CH_3$ | $CH_3$ | — | $-CH_2NHCOOCH_2(phenyl)$ | — | 149.5–152.0 |
| 109 | $CH_3$ | $CH_3$ | — | $-(CH_2)_3NHCOOCH_2(phenyl)$ | — | 146.0–151.0 |
| 110 | H | Phenyl | Endo | $-(CH_2)_5NHCOOCH_2(phenyl)$ | — | 114.5–122.5 |
| 111 | $CH_3$ | $CH_3$ | — | $-(CH_2)_5NHCOOCH_2(phenyl)$ | — | 149.5–152.5 |
| 112 | $CH_3$ | $CH_3$ | — | $-(CH_2)_2NHCOCCl_3$ | — | 159.0–163.5 |
| 113 | H | Pentafluorophenyl | Endo | $-(CH_2)_2NHCHO$ | — | 164.0–172.0 |
| 114 | H | Phenyl | Exo | $-CH_2NHCOCH_2NHCOCH_2NH$<br>$\qquad\qquad\qquad\qquad\qquad\quad\mid$<br>$\qquad\qquad\qquad(phenyl)CH_2OOC$ | — | 162.0–182.0 |
| 115 | H | Phenyl | Exo | $-CH\diagup^{CH(CH_3)_2}_{\diagdown NHCOCH_2NHCOCH_2NH}$<br>$\qquad\qquad\qquad\qquad\qquad\qquad\quad\mid$<br>$\qquad\qquad\qquad\qquad(phenyl)CH_2OOC$ | — | 140.0–147.0 |
| 116 | H | m-Fluorophenyl | Exo | $-CH_2NHCOCH_2NHCOCH_2NH$<br>$\qquad\qquad\qquad\qquad\qquad\quad\mid$<br>$\qquad\qquad\qquad(phenyl)CH_2OOC$ | — | 174.0–182.0 |

TABLE 5-continued

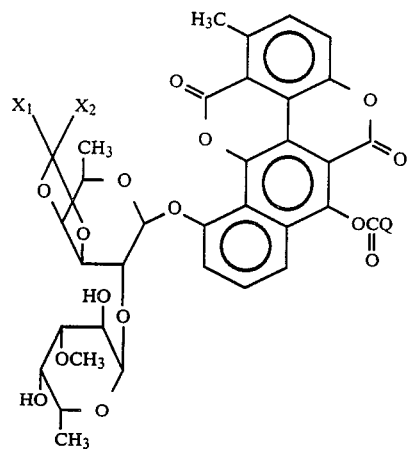

(I)

| Compound No. | $X_1$ | $X_2$ | Isomer[2] | $Q^{[1]}$ | Salt | Melting point (°C.) |
|---|---|---|---|---|---|---|
| 117 | H | m-Fluorophenyl | Exo | $-CH\overset{(CH_2)_4}{\diagdown}CH-NHCOCF_3$ | — | 185.0–194.0 |
| 118 | H | Phenyl | Exo | $-CH\overset{(CH_2)_4}{\diagdown}CH-NHCOCF_3$ | — | 176.0–185.0 |
| 119 | H | Phenyl | Exo | $-(CH_2)_5NHCOOCH_2(phenyl)$ | — | 178.0–186.0 |
| 120 | H | m-Nitrophenyl | Endo | $-(CH_2)_2NHCHO$ | — | 158.0–165.0 |
| 121 | H | Phenyl | Exo | $-CH\begin{smallmatrix}CH_2-(3-indolyl)\\ NHCOOCH_2(phenyl)\end{smallmatrix}$ | — | 165.0–173.0 |
| 122 | H | Phenyl | Exo | $-CH\begin{smallmatrix}CH_2(phenyl)\\ NHCOOCH_2(phenyl)\end{smallmatrix}$ | — | 195.0–202.0 |
| 123 | H | p-Bromophenyl | Exo | $-(CH_2)_2NHCO(phenyl)$ | — | 168.5–173.0 |
| 124 | H | p-Bromophenyl | Endo | $-(CH_2)_2NHCO(phenyl)$ | — | 164.5–170.0 |
| 125 | $CH_3$ | $CH_3$ | — | $-CH\begin{smallmatrix}CH(CH_3)_2\\ NHCOOCH_2(phenyl)\end{smallmatrix}$ | — | 148.0–152.0 |
| 126 | $CH_3$ | $CH_3$ | — | $-CH\begin{smallmatrix}CH_2-(3-indolyl)\\ NHCOOCH_2(phenyl)\end{smallmatrix}$ | — | 164.0–167.5 |
| 127 | H | p-Chlorophenyl | Endo | $-CH\begin{smallmatrix}CH_2(phenyl)\\ NHCOOCH_2(phenyl)\end{smallmatrix}$ | — | 155.0–164.0 |
| 128 | $CH_3$ | $CH_3$ | — | $-CH\begin{smallmatrix}CH_2(phenyl)\\ NHCOOCH_2(phenyl)\end{smallmatrix}$ | — | 164.0–166.0 |
| 129 | $CH_3$ | $CH_3$ | — | $-(CH_2)_{11}NHCOCH_3$ | — | 182.0–187.5 |
| 130 | H | $CH_2COCH_3$ | — | $-(CH_2)_5NHCOCF_3$ | — | 138.5–146.0 |
| 131 | $CH_3$ | $CH_2CH_3$ | — | $-CH_2CH\begin{smallmatrix}CH_3\\ NHCOCF_3\end{smallmatrix}$ | — | 148.0–155.0 |

TABLE 5-continued

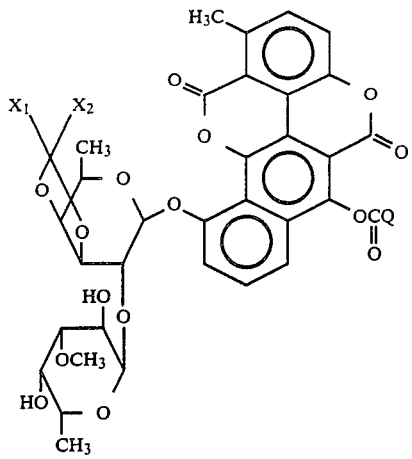
(I)

| Compound No. | $X_1$ | $X_2$ | Isomer[2] | $Q^{(1)}$ | Salt | Melting point (°C.) |
|---|---|---|---|---|---|---|
| 132 | | $-(CH_2)_5-$ | — | $-(CH_2)_2NHCOCF_3$ | — | 151.5–156.0 |
| 133 | | $-(CH_2)_5-$ | — | $-CH\begin{smallmatrix}CH_2-(3\text{-indolyl})\\NHCOOCH_2(\text{phenyl})\end{smallmatrix}$ | — | 158.0–165.0 |
| 134 | H | Phenyl | Exo | $-CH\begin{smallmatrix}CH_2CH_3\\CH_2N(CH_3)_2\end{smallmatrix}$ | HCl | 153.5–160.0 |
| 135 | H | Phenyl | Exo | $-CH\begin{smallmatrix}CH_3\\CH_2N\begin{smallmatrix}CH(CH_3)_2\\COOCH_2(\text{phenyl})\end{smallmatrix}\end{smallmatrix}$ | — | 202.0–209.5 |
| 136 | H | Phenyl | Exo | $-(CH_2)_2NHCOCH_2NH_2$ | HCl | 173.0–184.0 |
| 137 | H | Phenyl | Exo | $-CH\begin{smallmatrix}CH_3\\CH_2NHCOCH_2NH_2\end{smallmatrix}$ | HCl | 164.0–172.0 |
| 138 | H | Phenyl | Exo | $-CH\begin{smallmatrix}CH_3\\CH_2NH_2\end{smallmatrix}$ | HCl | 185.0–195.0 |
| 139 | H | Phenyl | Exo | $-(CH_2)_2N(CH_3)_2$ | HCl | 163.5–167.0 |
| 140 | H | Phenyl | Exo | $-CH\begin{smallmatrix}CH_3\\CH_2NHCH_3\end{smallmatrix}$ | HCl | — |
| 141 | H | Phenyl | Exo | $-CH\begin{smallmatrix}CH_3\\CH_2N\begin{smallmatrix}CH_3\\COOCH_2(\text{phenyl})\end{smallmatrix}\end{smallmatrix}$ | — | — |
| 142 | H | Phenyl | Exo | $-(CH_2)_2NHCH_3$ | HCl | 169.0–173.0 |

TABLE 5-continued

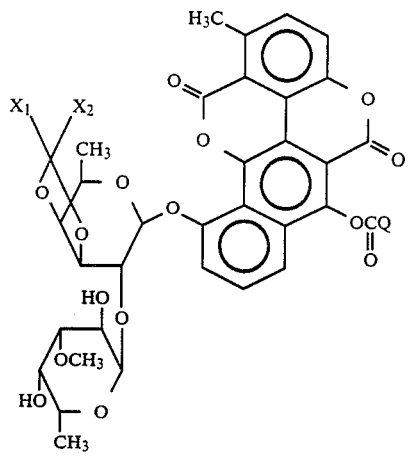

(I)

| Compound No. | $X_1$ | $X_2$ | Isomer[2] | $Q^{[1]}$ | Salt | Melting point (°C.) |
|---|---|---|---|---|---|---|
| 143 | H | Phenyl | Exo | −(CH$_2$)$_2$N(CH$_3$)(COOCH$_2$(phenyl)) | — | 175.0–178.0 |
| 144 | H | Phenyl | Exo | −CH(CH$_2$OCOCH$_3$)(NHCOOCH$_2$(phenyl)) | — | — |
| 145 | H | m-Fluorophenyl | Exo | −CH(NHCOOCH$_2$(phenyl))(CH$_2$CH$_2$SCH$_3$(=O)) | — | — |
| 146 | H | m-Fluorophenyl | Exo | −(CH$_2$)$_2$NHCO(phenyl)OCH$_3$(p) | — | — |
| 147 | H | Phenyl | Exo | −(CH$_2$)$_3$OH | — | 171.0–181.0 |
| 148 | H | Phenyl | Exo | −CH$_2$OCOCH$_3$ | — | 156.0–163.0 |
| 149 | H | Phenyl | Exo | −CH$_2$OCOCH$_2$CH$_2$Cl | — | 150.0–158.0 |
| 150 | H | Phenyl | Exo | −(CH$_2$)$_2$SOCH$_3$ | — | 170.0–180.0 |
| 151 | H | Phenyl | Exo | −CH(CH$_3$)(OCH$_2$(phenyl)) | — | 190.0–200.0 |
| 152 | H | Phenyl | Exo | −(CH$_2$)$_2$SCH$_3$ | — | 169.0–174.0 |
| 153 | H | Phenyl | Exo | −(CH$_2$)$_2$COCH$_3$ | — | 178.0–186.0 |
| 154 | H | Phenyl | Exo | −(CH$_2$)$_2$(phenyl) | — | 187.0–194.0 |
| 155 | H | 3-Thienyl | Exo | −(cyclopropyl) | — | 172.0–180.0 |
| 156 | CH$_3$ | CH$_3$ | — | −(CH$_2$)$_2$COCH$_3$ | — | 170.0–182.0 |
| 157 | CH$_3$ | CH$_3$ | — | −(CH$_2$)$_2$Cl | — | 164.0–170.0 |
| 158 | H | m-Fluorophenyl | Endo | −(phenyl)N(CH$_3$)$_2$(m) | — | 181.0–189.0 |
| 159 | H | p-Fluorophenyl | Exo | −CH$_2$CH(CH$_3$)$_2$ | — | 163.0–173.0 |
| 160 | H | m-Nitrophenyl | Endo | −(CH$_2$)$_2$CH=CH$_2$ | — | 146.0–154.0 |
| 161 | H | m-Trifluoromethylphenyl | Endo | −C(CH$_3$)=CHCH$_3$(E) | — | 148.0–158.0 |
| 162 | H | m-Trifluoromethylphenyl | Endo | −(CH$_2$)$_2$COCH$_3$ | — | 142.0–150.0 |
| 163 | H | m-Bromophenyl | Endo | −CH$_2$CH(CH$_3$)$_2$ | — | 148.0–158.0 |
| 164 | H | Phenyl | Exo | −(CH$_2$)$_2$Cl | — | 170.0–176.0 |
| 165 | H | Phenyl | Exo | −(CH$_2$)$_3$OCH$_2$(phenyl) | — | 184.0–188.0 |
| 166 | H | Phenyl | Exo | −(CH$_2$)$_2$NO$_2$ | — | 164.5–171.0 |
| 167 | H | Phenyl | Exo | −CH$_2$OCO(phenyl) | — | 186.0–196.0 |
| 168 | H | Phenyl | Exo | −(CH$_2$)$_2$SO$_2$CH$_3$ | — | 179.0–191.0 |
| 169 | H | Phenyl | Exo | −CH$_2$CH(CH$_3$)$_2$ | — | 194.0–204.0 |
| 170 | H | Phenyl | Exo | −(CH$_3$)$_3$ | — | 214.0–217.0 |
| 171 | CH$_3$ | CH$_3$ | — | −CH$_2$CH(CH$_3$)$_2$ | — | 213.0–225.0 |
| 172 | CH$_3$ | CH$_3$ | — | −CH(Br)(CH(CH$_3$)$_2$) | — | 163.0–169.0 |

TABLE 5-continued

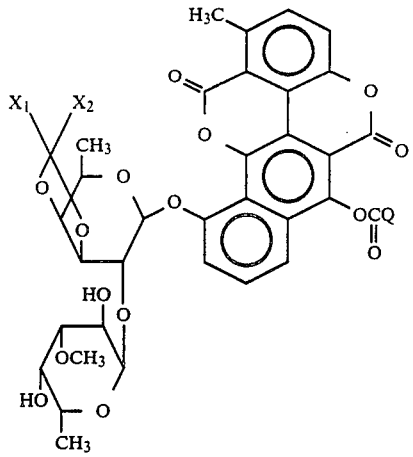
(I)

| Compound No. | $X_1$ | $X_2$ | Isomer[2] | $Q^{(1)}$ | Salt | Melting point (°C.) |
|---|---|---|---|---|---|---|
| 173 | $CH_3$ | $CH_3$ | — | $-C(CH_3)=CHCH_3(E)$ | — | 169.0–175.0 |
| 174 | $CH_3$ | $CH_3$ | — | $-CH_2S(phenyl)$ | — | 145.0–153.0 |
| 175 | $CH_3$ | $CH_3$ | — | $-(CH_2)_2CH=CH_2$ | — | 210.0–215.0 |
| 176 | $CH_3$ | $CH_3$ | — | $-(CH_2)_2OCH_2CH_3$ | — | 148.0–158.0 |
| 177 | $CH_3$ | $CH_3$ | — | $-(cyclopropyl)$ | — | 174.0–181.0 |
| 178 | $CH_3$ | $CH_3$ | — | $-(cyclopropyl)CH_3(2)$ | — | 166.0–176.0 |
| 179 | $CH_3$ | $CH_3$ | — | $-(phenyl)Br(p)$ | — | 208.0–218.0 |
| 180 | $CH_3$ | $CH_3$ | — | $-(phenyl)Cl_2(2,4)$ | — | 168.0–176.0 |
| 181 | $CH_3$ | $CH_3$ | — | $-(phenyl)Cl(o)$ | — | 173.0–181.0 |
| 182 | $CH_3$ | $CH_3$ | — | $-(phenyl)CF_3(p)$ | — | 180.0–188.0 |
| 183 | $CH_3$ | $CH_3$ | — | $-(phenyl)CN(p)$ | — | 189.0–198.0 |
| 184 | $CH_3$ | $CH_3$ | — | $-(phenyl)OCH_3(m)$ | — | 168.0–180.0 |
| 185 | $CH_3$ | $CH_3$ | — | $-(phenyl)Cl(p)$ | — | 183.0–190.0 |
| 186 | H | Phenyl | Endo | $-(phenyl)NO_2(p)$ | — | 191.0–197.0 |
| 187 | H | o-Chlorophenyl | Endo | $-(phenyl)CN(p)$ | — | 187.0–194.0 |
| 188 | H | m-Chlorophenyl | Endo | $-(CH_2)_2OCH_2CH_3$ | — | 133.0–142.0 |
| 189 | H | m-Nitrophenyl | Endo | $-(phenyl)Cl(o)$ | — | 167.0–180.0 |
| 190 | H | p-Chlorophenyl | Endo | $-(cyclopropyl)CH_3(2)$ | — | 174.0–180.0 |
| 191 | H | Phenyl | Exo | $-(CH_2)_2CH_3$ | — | 178.0–188.0 |
| 192 | H | Phenyl | Exo | $-(CH_2)_2CH=CH_2$ | — | 186.0–194.0 |
| 193 | H | Phenyl | Exo | $-(phenyl)OCH_3(m)$ | — | 178.0–183.0 |
| 194 | H | Phenyl | Exo | $-(phenyl)Cl(p)$ | — | 190.0–202.0 |
| 195 | H | Phenyl | Exo | $-(phenyl)CF_3(p)$ | — | 227.0–233.0 |
| 196 | H | Phenyl | Mixture (1:1) | $-(CH_2)_4CH_3$ | — | 145.0–154.0 |
| 197 | $CH_3$ | $CH_3$ | — | $-CH=CH_2$ | — | 166.0–174.0 |
| 198 | $CH_3$ | $CH_3$ | — | $-CH=C\begin{smallmatrix}CH_3\\CF_3\end{smallmatrix}$ | — | 170.0–190.0 |
| 199 | $CH_3$ | $CH_3$ | — | $-CH_2OCO(phenyl)$ | — | 158.0–168.0 |
| 200 | $CH_3$ | $CH_3$ | — | $-CH=CHCH_3(E)$ | — | 172.0–181.0 |
| 201 | $CH_3$ | $CH_3$ | — | $-(CH_2)_2C\equiv CH$ | — | 155.0–163.0 |
| 202 | $CH_3$ | $CH_3$ | — | $-CH_2CH_2CO_2CH_3$ | — | 148.0–155.0 |
| 203 | $CH_3$ | $CH_3$ | — | $-CH_3$ | — | 184.0–190.0 |
| 204 | $CH_3$ | $CH_3$ | — | $-(CH_2)_3Cl$ | — | 205.0–213.0 |
| 205 | $CH_3$ | $CH_3$ | — | $-CH_2O-(phenyl)$ | — | 193.0–203.0 |
| 206 | $CH_3$ | $CH_3$ | — | $-(CH_2)_2CO-(phenyl)F(p)$ | — | 153.0–161.0 |
| 207 | $CH_3$ | $CH_3$ | — | $-(phenyl)CO_2CH_3(p)$ | — | 180.0–188.0 |
| 208 | $CH_3$ | $CH_3$ | — | $-(phenyl)OCH_3(p)$ | — | 202.0–212.0 |
| 209 | $CH_3$ | $CH_3$ | — | $-(phenyl)N(CH_3)_2(m)$ | — | 176.0–186.0 |
| 210 | H | o-Fluorophenyl | Mixture (1:5) | $-(CH_2)_2Cl$ | — | 161.0–171.0 |
| 211 | H | 2-Furyl | Mixture (1:1) | $-(phenyl)CO_2CH_3(p)$ | — | 190.0–199.0 |
| 212 | H | Phenyl | Endo | $-(CH_2)_2CH_3$ | — | 158.0–168.0 |
| 213 | H | Phenyl | Endo | $-(CH_2)_2CH=CH_2$ | — | 152.0–160.0 |
| 214 | H | Phenyl | Endo | $-(CH_2)_3Cl$ | — | 153.0–162.0 |
| 215 | H | Phenyl | Endo | $-C(CH_3)=CHCH_3(E)$ | — | 172.0–179.0 |
| 216 | H | o-Methoxyphenyl | Exo | $-(CH_2)_2CH_3$ | — | 167.0–178.0 |
| 217 | H | 2,4-Dichlorophenyl | Endo | $-(CH_2)_2CH=CH_2$ | — | 140.0–150.0 |
| 218 | H | 2-Phenylethyl | Exo | $-(phenyl)OCH_3(m)$ | — | 148.0–158.0 |
| 219 | H | $CH_2CH_3$ | — | $-CH\begin{smallmatrix}CH_3\\CH_2CH_3\end{smallmatrix}$ | — | 168.0–176.0 |

TABLE 5-continued

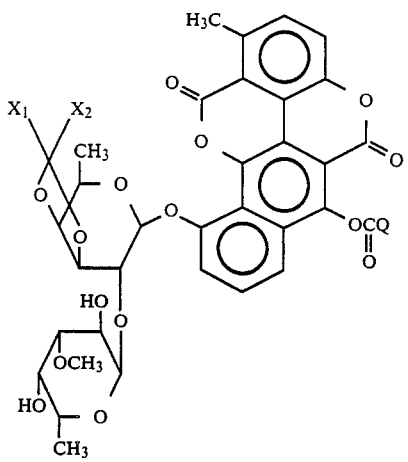
(I)

| Compound No. | $X_1$ | $X_2$ | Isomer[2] | $Q^{[1]}$ | Salt | Melting point (°C.) |
|---|---|---|---|---|---|---|
| 220 | $CH_3$ | $CH_3$ | — | $-(CH_3)_8CH_3$ | — | 209.0–212.0 |
| 221 | $-(CH_2)_5-$ | | — | $-CH=CHCH_3(E)$ | — | 167.0–174.0 |
| 222 | $CH_3$ | $CH_3$ | — | $-CH(CH_3)_2$ | — | 178.0–190.0 |
| 223 | $CH_3$ | $CH_3$ | — | $-CH\begin{matrix}CH_2\\ \phantom{-}\\ CH_2CH=CH\end{matrix}CH_2$ | — | 170.0–180.0 |
| 224 | $CH_3$ | $CH_3$ | — | $-(CH_2)_2CO(phenyl)$ | — | 158.0–165.0 |
| 225 | $CH_3$ | $CH_3$ | — | $-CH_2O-(phenyl)F(p)$ | — | 194.0–202.0 |
| 226 | $CH_3$ | $CH_3$ | — | $-(phenyl)Cl(m)$ | — | 173.0–181.0 |
| 227 | H | Phenyl | Endo | $-CH_2CH(CH_3)_2$ | — | 157.0–165.0 |
| 228 | H | 2-Furyl | Mixture (1:1) | $-(CH_2)_2CH_3$ | — | 175.0–181.0 |
| 229 | H | Phenyl | Endo | $-(phenyl)Br(p)$ | — | 195.0–205.0 |
| 230 | H | Phenyl | Endo | $-(cyclopropyl)$ | — | 176.0–182.0 |
| 231 | H | Phenyl | Exo | $-C(CH_3)=CHCH_3(E)$ | — | 182.0–188.0 |
| 232 | H | Phenyl | Exo | $-(cyclopropyl)$ | — | 180.0–185.0 |
| 233 | H | 2-Phenylethyl | Exo | $-(cyclopropyl)$ | — | 159.0–165.0 |
| 234 | H | p-Methoxyphenyl | Exo | $-C(CH_3)=CHCH_3(E)$ | — | 210.0–215.0 |
| 235 | $CH_3$ | $CH_3$ | — | $-(CH_2)_5Br$ | — | 219.0–225.0 |
| 236 | H | Phenyl | Mixture (1:1) | $-CH_2CH\begin{matrix}CH_3\\ \phantom{-}\\ CH_2C(CH_3)_3\end{matrix}$ | — | 175.0–195.0 |
| 237 | $CH_3$ | $CH_3$ | — | $-CH_2CH\begin{matrix}CH_3\\ \phantom{-}\\ CH_2C(CH_3)_3\end{matrix}$ | — | 210.0–220.0 |
| 238 | $CH_3$ | $CH_3$ | — | $-CH=CHCH=CHCH_3$ | — | 176.0–184.0 |
| 239 | $CH_3$ | $CH_3$ | — | $-CH\begin{matrix}CH_2CH_3\\ \phantom{-}\\ (CH_2)_3CH_3\end{matrix}$ | — | 172.0–177.0 |
| 240 | $CH_3$ | $CH_3$ | — | $-(CH_2)_2-(cyclohexyl)$ | — | 228.0–234.0 |
| 241 | $-(CH_2)_5-$ | | — | $-CH\begin{matrix}CH_3\\ \phantom{-}\\ CH_2CH_3\end{matrix}$ | — | 158.0–165.0 |
| 242 | $CH_3$ | $CH_3$ | — | $-(phenyl)$ | — | 221.0–226.0 |
| 243 | $CH_3$ | $CH_3$ | — | $-COCH_3$ | — | — |
| 244 | $CH_3$ | $CH_3$ | — | $-COOCH(CH_3)_2$ | — | — |
| 245 | $CH_3$ | $CH_3$ | — | $-(cyclopentyl)$ | — | — |
| 246 | H | Phenyl | Exo | $-(CH_2)_2COO(phenyl)$ | — | — |

TABLE 5-continued (I)

| Compound No. | $X_1$ | $X_2$ | Isomer[2] | $Q^{(1)}$ | Salt | Melting point (°C.) |
|---|---|---|---|---|---|---|
| 247 | H | Phenyl | Exo | —CH$_2$CH$_2$CN | — | — |
| 248 | H | 2-(3-Methylthienyl) | Exo | —(CH$_2$)$_2$COCH$_3$ | — | — |
| 249 | H | 2-(3-Bromothienyl) | Exo | —CH$_2$CHCH$_3$ with CH$_3$ branch | — | — |
| 250 | H | 2-(5-Methylfuryl) | Exo | —(CH$_2$)$_2$COCH$_3$ | — | — |

Note:
[1]The symbol (p) in —(CH$_2$)$_2$NHCO(phenyl)OCH$_3$(p) of compound No. 146 indicates that the phenyl nucleus is substituted by OCH$_3$ in the p-position. The symbol (2) in —(cyclopropyl)CH$_3$(2) of compound No. 178 indicates that the cyclopropyl is substituted by CH$_3$ in the 2-position. The other symbols are interpreted according to the above. The symbol (E) denotes Entgegen.
Note:
[2]In the mixture, the ratio is that of exo form to endo form.

Next, NMR data of typical compounds of the above-mentioned compounds of this invention are shown below.

Compound No. 12

NMR (60 MHz, δ values in CDCl$_3$): 1.30(3H, d, J=7 Hz, CH$_3$), 1.48(3Hx2, d, J=7 Hz, CH$_3$x2), 2.87(3H, s, Ar—CH$_3$), 3.37(3H, s, O—CH$_3$), 5.26(1H, d, J=8 Hz, anomer proton), 5.89(1H, d, J=4 Hz, anomer prokton), 6.33(1H, s, —O—CH—O—), 7.17-8.10(10H, aromatic proton)

Compound No. 13

NMR (60 MHz, δ values in CDCl$_3$): 1.33(3H, d, J=7 Hz, CH$_3$), 1.47(3Hx2, d, J=7 Hz CH$_3$x2), 2.81(3H, s, Ar—CH$_3$), 3.37(3H, s, O—CH$_3$), 5.30(1H, d, J=8 Hz, anomer proton), 5.92 (1H, d, J=4 Hz, anomer proton), 6.34(1H, s, —O—CH—O—), 7.07-8.20 (15H, aromatic proton)

Compound No. 20

NMR (60, MHz δ values in CDCl$_3$—CD$_3$OD): 1.30(3H, d, J=7 Hz, CH$_3$), 1.50(3H, d, J=7 Hz, CH$_3$), 2.86(3H, s, Ar—CH$_3$), 3.38(3H, s, O—CH$_3$), 5.39(1H, d, J=8 Hz, anomer proton), 5.95(1H, d, J=4 Hz, anomer proton), 6.40(1H, s, —O—CH—O—), 7.27-8.16 (10H, aromatic proton), 8.18(1H, s, formyl proton)

Compound No. 21

NMR (60 MHz, δ values in CDCl$_3$—CD$_3$OD): 1.28(3H, d, J=7 Hz, CH$_3$), 1.50(3H, d, J=7 Hz, CH$_3$), 2.89(3H, s, Ar—CH$_3$), 3.41(3H, s, O—CH$_3$), 5.40(1H, d, J=8 Hz, anomer proton), 5.90(1H, d, J=4 Hz, anomer proton), 6.38(1H, s, —O—CH—O—), 7.17-8.00 (10H, aromatic proton)

Compound No. 23

NMR (60 MHz, δ values in CDCl$_3$) 1.32(3H, d, J=7 Hz, CH$_3$), 1.48(3H, d, J=7 Hz, CH$_3$), 2.91(3H, s, Ar—CH$_3$), 3.43(3H, s, O—CH$_3$), 5.34(1H, d, J=8 Hz, anomer proton), 6.00(1H, d. J=4 Hz, anomer proton), 6.42(1H, s, —O—CH—O—), 7.17-8.27 (15H, aromatic proton)

Compound No. 24

NMR (60 MHz, δ values in CDCl$_3$—Cd$_3$OD): 1.30(3H, d, J=7 Hz, CH$_3$), 1.50(3H, d, J=7 Hz, CH$_3$), 2.87(3H, s, Ar—CH$_3$), 3.40(3H, s, O—CH$_3$), 5.37(1H, d, J=8 Hz, anomer proton), 5.91(1H, d, J=4 Hz, anomer proton), 6.36(1H, s, —O—CH—O—), 7.17–8.00 (10H aromatic proton)

Compound No. 25

NMR (60 MHz, δ values in CDCl$_3$): 1.3(3H, d, J=7 Hz, CH$_3$), 1.49(3H, d, J=7 Hz, CH$_3$), 2.87(3H, s, Ar—CH$_3$), 3.39(3H, s, O—CH$_3$), 3.42(3H, s, N—CH$_3$), 5.29(1H, d, J=8 Hz, anomer proton), 5.93(1H, d, J=4 Hz anomer proton), 6.37(1H, s, —O—CH—O—), 7.17–8.17(10H, aromatic proton)

Compound No. 26

NMR (60 MHz, δ values in CDCl$_3$) 1.30(3H, d, J=7 Hz, CH$_3$), 1.48(3H, d, J=7 Hz, CH$_3$), 1.60–2.10(8H, m, cyclohexyl portion), 2.91(3H, s, Ar—CH$_3$), 3.41(3H, s, O—CH$_3$), 5.30(1H, d, J=8 Hz, anomer proton), 5.94(1H, d, J=4 Hz, anomer proton), 6.38(1H, s, —O—CH—O—), 7.17–7.93(10H, aromatic proton)

Compound No. 27

NMR (60 MHz, δ values in CDCl$_3$): 1.31(3H, d, J=7 Hz, CH$_3$), 1.48(3H, d, J=7 Hz, CH$_3$), 1.58–1.98(8H, m, cyclohexyl portion), 2.90(3H, s, Ar—CH$_3$), 3.40(3H, s, O—CH$_3$), 5.28(1H, d, J=8 Hz, anomer proton), 5.91(1H, d, J=4 Hz, anomer proton), 6.34(1H, s, —O—CH—O—), 7.00–7.91(9H, aromatic proton)

Compound No. 28

NMR (60 MHz, δ values in CDCl$_3$—CD$_3$OD): 1.06(3H, d, J=7 Hz, CH$_3$), 1.48(3H, d, J=7 Hz, CH$_3$), 2.87(3H, s, Ar—CH$_3$), 3.40(3H, s, O—CH$_3$), 5.38(1H, d, J=8 Hz, anomer proton), 5.80(1H, d, J=4 Hz, anomer proton), 6.00(1H, s, —O—CH—O—), 7.17–8.23(10H, aromatic proton)

Compound No. 29

NMR (60 MHz, δ values in CDCl$_3$—CD$_3$O: 1.05(3H, d, J=7 Hz, CH$_3$), 1.47(3H, d, J=7 Hz, CH$_3$), 2.02(3H, s, N—Ac), 2.85(3H, s, Ar—CH$_3$), 3.37(3H, s, O—CH ), 5.34(1H, d, J=8 Hz, anomer proton), 5.77(1H, d, J=4 Hz, anomer proton), 5.96(1H, s, —O—CH—O—), 7.21–8.04(10 H, aromatic proton)

Compound No. 30

NMR (60 MHz, δ values in CDCl$_3$): 1.12(3H, d, J=7 Hz, CH$_3$), 1.47(3Hx2, d, J=7 Hz, CH$_3$x2), 2.81(3H, s, Ar—CH$_3$), 3.37(3H, s, O—CH$_3$), 5.33(1H, d, J=8 Hz, anomer proton), 5.77(1H, d, J=4 Hz, anomer proton), 6.04(1H, s, —O—CH—O—), 7.20–8.27(9H, aromatic proton)

Compound No. 31

NMR (60 MHz, δ values in CDCl$_3$): 1.19(3H, d, J=7 Hz, CH$_3$), 1.51(3H, d, J=7 Hz, CH$_3$), 2.90(3H, s, Ar—CH$_3$), 3.48(3H, s, O—CH$_3$), 5.46(1H, d, J=8 Hz, anomer proton), 5.86(1H, d, J=4 Hz, anomer proton)

6.06(1H, s, —O—CH—O—), 7.25–8.02 (9H, aromatic proton)

Compound No. 37

NMR (60 MHz, δ values in CDCl$_3$) 1.30(3H, d, J=7 Hz, CH$_3$), 1.47(3H, d, J=7 Hz, CH$_3$), 1.53(3H, d, J=7 Hz, CH$_3$), 2.88(3H, s, Ar—CH$_3$), 3.39(3H, s, O—CH$_3$), 5.28(1H, d, J=8 Hz, anomer proton), 5.91(1H, d, J=4 Hz, anomer proton), 6.35(1H, s, —O—CH—O—), 7.00–8.17(9H, aromatic proton)

Compound No. 38

NMR (60 MHz, δ values om CDCl$_3$—CD$_3$OD): 1.29(3H, d, J=7 Hz, CH$_3$), 1.48(3H, d, J=7 Hz, CH$_3$), 2.02(3H, s, N—Ac), 2.84(3H, s, Ar—CH$_3$), 3.34(3H, s, O—CH$_3$), 5.32(1H, d, J=8 Hz, anomer proton), 5.85(1H, J=8 Hz, anomer proton), 6.30(1H, s, —O—CH—O—), 7.14–8.10(10H, aromatic proton)

Compound No. 39

NMR (60 MHz, δ values in CDCl$_3$): 1.35(3H, d, J=7 Hz, CH$_3$), 1.52(3H, d, J=7 Hz, CH$_3$), 1.58(3H, d, J=7 Hz, CH$_3$), 2.96(3H, s, Ar—CH$_3$), 3.48(3H, s, O—CH$_3$), 5.35(1H, d, J=8 Hz, anomer proton), 6.00(1H, d, J=4 Hz, anomer proton), 6.45(1H, s, —O—CH—O—), 7.25-8.17(10H, aromatic proton)

Compound No. 40

NMR (60 MHz, δ values in CDCl₃—CD₃OD): 1.05(3H×½, d, J=7 Hz, CH₃), 1.30(3H×½, d, J=7 Hz, CH₃), 1.50(3H, d, J=7 Hz, CH₃), 2.92(3H, s, Ar—CH₃), 3.43(3H, s, O—CH₃), 5.42(1H, m, anomer proton), 5.97(1H, m, anomer proton), 6.02(1H × ½, s, —O—CH(—)—O—), 6.40(1H × ½, s, —O—CH(—)—O—), 7.27-7.93 (10H, aromatic proton), 8.20(1H, s, formyl proton), (a diastereomer mixture of benzylidene)

Compound No. 41

NMR (60 MHz, δ values in CDCl₃) 1.10(3H×½, d, J=7 Hz, CH₃), 1.32(3H×½, d, J=7 Hz, CH₃), 1.50(3H, d, J=7 Hz, CH₃), 2.88(3H, s, Ar—CH₃), 3.40(3H, s, O—CH₃), 5.28(1H, m, anomer proton), 5.87(1H, m, anomer proton), 5.98(1H × ½, s, —O—CH(—)—O—), 6.35(1H × ½, s, —O—CH(—)—O—), 7.23-7.93(10H, aromatic proton) (a diastereomer mixture of benzylidene)

Compound No. 43

NMR (60 MHz δ values in CDCl₃—CD₃OD): 1.29(3H, d, J=7 Hz, CH₃), 1.47(3H, d, J=7 Hz, CH₃), 1.61-2.01(4H, m, CH₂×2), 2.79(3H, s, Ar—CH₃), 3.36(3H, s, O—CH₃), 5.32(1H, d, J=8 Hz, anomer proton), 5.91(1H, d, J=4 Hz, anomer proton), 6.33(1H, s, —O—CH(—)—O—), 7.21-8.21(10H, aromatic proton)

Compound No. 44

NMR (60 MHz, δ values in CDCl₃): 1.09(3H, d, J=7 Hz, CH₃), 1.48(6H, d, J=7 Hz, CH₃×2), 2.83(3H, s, Ar—CH₃), 3.37(3H, s, O—CH₃), 5.29(1H, d, J=8 Hz, anomer proton), 5.77(1H, d, J=4 Hz, anomer proton), 5.99(1H, s, —O—CH(—)—O—), 7.17-7.92 (10H, aromatic proton)

Compound No. 45

NMR (60 MHz, δ values in CDCl₃-CD₃OD): 1.05(3H, d, J=7 Hz, CH₃), 1.48(3H, d, J=7 Hz, CH₃), 2.87(b 3H, s, Ar—CH₃), 3.40(3H, s, O—CH₃), 5.38(1H, d, J=8 Hz, anomer proton), 5.80(1H, d, J=4 Hz, anomer proton), 5.98(1H, s, —O—CH(—)—O—), 7.23-7.93 (10H, aromatic proton), 8.13(1H, s, formyl proton)

Compound No. 46

NMR (60 MHz, δ values in CDCl₃) 1.12(3H, d, J=7 Hz, CH₃), 1.45(3H, d, J=7 Hz, CH₃), 2.79(3H, s, Ar—CH₃), 3.38(3H, s, O—CH₃), 5.34(1H, d, J=8 Hz, anomer proton), 5.74(1H, d, J=4 Hz, anomer proton), 5.92(1H, s, —O—CH(—)—O—), 7.07-8.04 (9H, aromatic proton), 8.08(1H, s, formyl proton):

Compound No. 47

NMR (60 MHz, δ values in CDCl₃): 1.15(3H, d, J=7 Hz, CH₃), 1.45(3H, d, J=7 Hz, CH₃), 2.79(3H, s, Ar—CH₃), 3.37(3H, s, O—CH₃), 5.32(1H, d, J=8 Hz, anomer proton), 5.76(1H, d, J=4 Hz, anomer proton), 5.96(1H, s, —O—CH(—)—O—), 6.93-8.00 (14H, aromatic proton)

Compound No. 48

NMR (60 MHz, δ values in CDCl₃): 1.23-1.80(12H, CH₃×4), 2.80(3H, s, Ar—CH₃), 3.38(3H, s, O—CH₃), 5.20(1H, m, anomer proton), 5.83(1H, m, anomer proton), 7.23-8.20(5H, aromatic proton), 8.17(1H, formyl proton)

Compound No. 49

NMR (60 MHz, δ values in CDCl₃): 1.23-1.83(12H, CH₃ ×4), 2.83(3H, s, Ar—CH₃), 3.40(3H, s, O—CH₃), 5.20(1H, m, anomer proton), 5.83(1H, m, anomer proton), 7.27-8.03(5H, aromatic proton)

Compound No. 50

NMR (60 MHz, δ values in CDCl₃): 1.28-1.87(12H, CH₃×4), 2.83(3H, s, Ar—CH₃), 3.38(3H, s, O—CH₃), 5.17(1H, m, anomer proton), 5.83(1H, m, anomer proton), 7.23-8.20(10H, aromatic proton)

Compound No. 51

NMR (60 MHz, δ values in CDCl₃—CD₃OD): 1.27-1.83(15H, CH₃×5), 2.85(3H, s, Ar—CH₃), 3.37(3H, s, O—CH₃), 5.27(1H, m, anomer proton), 5.82(1H, m, anomer proton), 7.23-8.00(5H, aromatic proton)

Compound No. 52

NMR (60 MHz, δ values in CDCl₃): 1.10(3H, d, J=7 Hz, CH₃), 1.45(3H, d, J=7 Hz, CH₃), 2.75(3H, s, Ar—CH₃), 3.34(3H, s, O—CH₃), 5.27(1H, d, J=8 Hz, anomer proton), 5.67(1H, d, J=4 Hz, anomer proton), 5.93(1H, s, —O—CH(—)—O—), 7.06–8.16 (9H, aromatic proton), 8.02(1H, s, formyl proton)

Compound No. 53

NMR (60 MHz, δ values in CDCl$_3$): 1.13(3H, d, J=7 Hz, CH$_3$), 1.47(3H, d, J=7 Hz, CH$_3$), 1.99(3H, s, N—Ac), 2.79(3H, s, Ar—CH$_3$), 3.39(3H, s, O—CH$_3$), 5.34(1H, d, J=8 Hz, anomer proton), 5.73(1H, d, J=4 Hz, anomer proton),

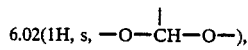
6.02(1H, s, —O—CH—O—), 7.09–8.22(9H, aromatic proton)

Compound No. 54

NMR (60 MHz, δ values in CDCl$_3$) 1.15(3H, d, J=7 Hz, CH$_3$), 1.44(3H, d, J=7 Hz, CH$_3$), 2.76(3H, s, Ar—CH$_3$), 3.35(3H, s, O—CH$_3$), 5.28(1H, d, J=8 Hz, anomer proton), 5.68(1H, d, J=4 Hz, anomer proton),

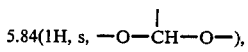
5.84(1H, s, —O—CH—O—), 6.95–8.00(9H, aromatic proton), 8.03(1H, s, formyl proton)

Compound No. 55

NMR (60 MHz, δ values in CDCl$_3$—CD$_3$OD): 1.24(3H, d, J=7 Hz, CH$_3$), 1.42(3H, d, J=7 Hz, CH$_3$), 2.45(3H, s, Ar—CH$_3$), 2.77(3H, s, Ar—CH$_3$), 3.33(3H, s, O—CH$_3$), 5.24(1H, d, J=8 Hz, anomer proton), 5.81(1H, d, J=4 Hz, anomer proton),

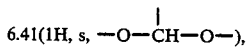
6.41(1H, s, —O—CH—O—), 6.90–8.17(9H, aromatic proton), 8.00(1H, s, formyl proton)

Compound No. 56

NMR (60 MHz, δ values in CDCl$_3$): 1.16(3H, d, J=7 Hz, CH$_3$), 1.48(3H, d, J=7 Hz, CH$_3$), 2.84(3H, s, Ar—CH$_3$), 3.40(3H, s, O—CH$_3$), 5.37(1H, d, J=8 Hz, anomer proton), 5.77(1H, d, J=4 Hz, anomer proton),

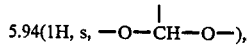
5.94(1H, s, —O—CH—O—), 7.11–8.11(9H, aromatic proton)

Compound No. 57

NMR (60 MHz, δ values in CDCl$_3$): 1.11(3H, d, J=7 Hz, CH$_3$), 1.47(3H, d, J=7 Hz, CH$_3$), 2.85(3H, s, Ar—CH$_3$), 3.39(3H, s, O—CH$_3$), 5.34(1H, d, J=8 Hz, anomer proton), 5.78(1H, d, J=4 Hz, anomer proton),

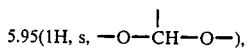
5.95(1H, s, —O—CH—O—), 6.95–8.21(9H, aromatic proton)

Compound No. 58

NMR (60 MHz, δ values in CDCl$_3$) 1.09(3H, d, J=7 Hz, CH$_3$), 1.52(3H, d, J=7 Hz, CH$_3$), 2.87(3H, s, Ar—CH$_3$), 3.46(3H, s, O—CH$_3$), 5.41 (1H, d, J=8 Hz, anomer proton), 5.86(1H, d, J=4 Hz, anomer proton),

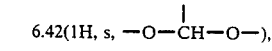
6.42(1H, s, —O—CH—O—), 7.2–8.4 (9H, aromatic proton), 8.42(1H, s, formyl proton)

Compound No. 60

NMR (60 MHz, δ values in CDCl$_3$): 1.31(3H, d, J=7 Hz, CH$_3$), 1.48(3H×2, d, J=7 Hz, CH$_3$×2), 2.86(3H, s, A—CH$_3$), 3.39(3H, s, O—CH$_3$), 5.13(2H, s, benzyl proton), 5.29(1H, d, J=8 Hz, anomer proton), 5.94(1H, d, J=4 Hz, anomer proton),

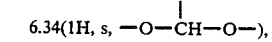
6.34(1H, s, —O—CH—O—), 7.24–7.97(14H, aromatic proton)

Compound No. 61

NMR (60MHz, δ values in CDCl$_3$): 1.32(3H, d, J=7 Hz, CH$_3$), 1.45(3H,) =7Hz, CH$_3$), 2.76(3H, s, Ar—CH$_3$), 3.37(3H, s, O—CH$_3$), 5.06(2H, s, benzyl proton), 5.32(1H, d, J=8 Hz, anomer proton), 5.89(1H, d, J=4 Hz, anoer proton),

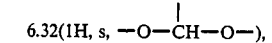
6.32(1H, s, —O—CH—O—), 6.93–7.90(1H, aromatic proton)

Compound No. 62

NMR (60 MHz, δ values in CDCl$_3$): 1.28(3H, d, J=7 Hz, CH$_3$ ), 1.45(3H, d, J=7 Hz, CH$_3$), 1.50–2.10 (8H, m, cyclohexyl portion), 2.86(3H, s, Ar—CH$_3$), 3.37(3H, s, O—CH$_3$), 5.08(2H, s, benzyl proton), 5.22(1H, d, J=8 Hz, anomer proton), 5.84(1H, d, J=4 Hz, anomer proton),

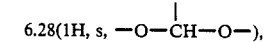
6.28(1H, s, —O—CH—O—), 7.17–8.10(15H, aromatic proton)

Compound No. 63

NMR (60 MHz, δ values in CDCl$_3$): 1.20–1.80(14H, CH$_3$×4, CH$_2$×1), 2.17(3H, s, S—CH$_3$), 2.87(3H, s, Ar—CH$_3$), 3.42(3H, s, O—CH$_3$), 5.20(3H, m, benzyl proton+anomer proton), 5.85(1H, m, anomer proton), 7.20–8.20(10H, aromatic proton)

Compound No. 64

NMR (60 MHz, δ values in CDC$_3$) 1.13(3H, d, J=7 Hz, CH$_3$), 1.27–1.93(13H, m, CH$_3$×1, CH$_2$×5), 2.81(3H, s, Ar—CH$_3$), 3.40(3H, s, O—CH$_3$), 5.33(1H, d, J=8 Hz, anomer proton), 5.76(1H, d, J=4 HZ, anomer proton),

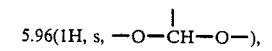
5.96(1H, s, —O—CH—O—), 7.00–8.93(9H, aromatic proton)

Compound No. 135

NMR (60 MHz, δ values in CDCl$_3$): 1.03-1.69(3Hx5, CH$_3$x ), 2.87(3H, s, Ar—CH$_3$), 3.41(3H, s, O—CH$_3$), 5.21(2H, s, benzyl proton), 5.32(1H, d, J=8Hz, anomer proton), 5.93(1H, d, J=4Hz, anomer proton), 6.36(1H, s, —O—CH(—)—O—), 7.13-8.00(15H, aromatic proton)

Compound No. 147

NMR (60 MHz, δ values in CDCl$_3$): 1.30(3H, d, J=7 Hz, CH$_3$), 1.46(3H, d, J=7 Hz, CH$_3$), 2.87(3H, s, Ar—CH$_3$), 3.40(3H, s, O—CH$_3$), 5.28(1H, d, J=8 Hz, anomer proton), 5.91(1H, d, J=4 Hz, anomer proton), 6.32(1H, s, —O—CH(—)—O—), 6.90-8.33(10H, aromatic proton)

Compound No. 148

NMR (60 MHz, δ values in CDCl$_3$—CD$_3$OD): 1.30(3H, d, J=7 Hz, CH$_3$), 1.48(3H, d, J=7 Hz, CH$_3$), 2.25(3H, s, -OAc), 2.91(3H, s, Ar—CH$_3$), 3.40(3H, s, O—CH$_3$), 5.17(2H, s, -CO—CH$_2$-O—), 5.36(1H, d, J=8 Hz, anomer proton), 5.92(1H, d, J=4 Hz, anomer [6 37(1H, s, -O—H-O—) 7.30-8.07(10H, proton), 6.37(1H, s, —O—CH(—)—O—), 7.30-8.07(10H, aromatic proton)

Compound No. 149

NMR (60 MHz, δ values in CDCl$_3$): 1.31(3H, d, J=7 Hz, CH$_3$), 1.48(3H, d, J=7 Hz, CH$_3$), 2.87(3H, s, Ar—CH$_3$), 3.39(3H, s, O—CH$_3$), 5.13-6.17(4H, anomer proton x2, -CO—CH$_2$-O—), 6.33(1H, s, —O—CH(—)—O—), 7.20-8.20(10H, aromatic proton)

Compound No. 150

NMR (60 MHz, δ values in CDCl$_3$): 1.31(3H, d, J=7 Hz, CH$_3$), 1.49(3H, d, J=7 Hz, CH$_3$), 2.67(3H, s, -SO—CH$_3$), 2.87(3H, s, Ar—CH$_3$), 3.40(3H, s, O—CH$_3$), 5.28(1H, d, J=8 Hz, anomer proton), 5.92(1H, d, J=4 Hz, anomer proton), 6.35(1H, s, —O—CH(—)—O—), 7.25-8.08(10H, aromatic proton)

Compound No. 151

NMR (60 MHz, δ values in CDCl$_3$): 1.30(3H, d, J=7 Hz, CH$_3$), 1.49(3H, d, J=7 Hz, CH$_3$), 1.81(3H, d, J=7 Hz, CH$_3$), 2.86(3H, s, Ar—CH$_3$), 3.40(3H, s, O—CH$_3$), 5.29(1H, d, J=8 Hz, anomer proton), 5.92(1H, d, J=4 Hz, anomer proton)

6.36(1H, s, —O—CH(—)—O—), 7.25-7.96(15H, aromatic proton)

Compound No. 152

NMR (60 MHz, δ values in CDCl$_3$): 1.31(3H, d, J=7 Hz, CH$_3$), 1.47(3H, d, J=7 Hz, CH$_3$), 2.24(3H, s, —S—CH$_3$), 2.87(3H, s, Ar—CH$_3$), 3.38(3H, s, O—CH$_3$), 5.27(1H, d, J=8 Hz, anomer proton), 5.91(1H, d, J=4 Hz, anomer proton), 6.34(1H, s, —O—CH(—)—O—), 7.10-8.26(10H, aromatic proton)

Compound No. 153

NMR (60 MHz, δ values in CDCl$_3$): 1.28(3H, d, J=7 Hz, CH$_3$), 1.46(3H, d, J=7 Hz, CH$_3$), 2.20(3H, s, —CO—CH$_3$), 2.81(3H, s, Ar—CH$_3$), 3.35(3H, s, O—CH$_3$), 5.25(1H, d, J=8 Hz, anomer proton), 5.87(1H, d, J=4 Hz, anomer proton), 6.29(1H, s, —O—CH(—)—O—), 7.17-8.13(10H, aromatic proton)

Compound No. 154

NMR (60 MHz, δ values in CDCl$_3$—CD$_3$OD): 1.28(3H, d, J=7 Hz, CH$_3$), 1.49(3H, d, J=7 Hz, CH$_3$), 2.86(3H, s, Ar—CH$_3$), 3.39(3H, s, O—CH$_3$), 5.40(1H, d, J=8 Hz, anomer proton), 5.9211H, d, J=4 Hz, anomer proton), 6.37(1H, s, —O—CH(—)—O—), 7.07-7.90(15H, aromatic proton)

Compound No. 155

NMR (60 MHz, δ values in CDCl$_3$): 0.75-1.63(10H, CH$_3$x2, CH$_2$x2), 2.84(3H, s, Ar—CH$_3$), 3.39(3H, s, O—CH$_3$), 5.28(1H, d, J=8 Hz, anomer proton), 5.88(1H, d, J=4 Hz, anomer proton), 6.42(1H, s, —O—CH(—)—O—), 6.94-8.07 (8H, thienyl group and aromatic proton)

Compound No. 156

NMR (60 MHz, δ values in CDCl$_3$): 1.16-1.85(3Hx4, CH$_3$x4), 2.26(3H, s, —COCH$_3$), 2.86(3H, s, Ar—CH$_3$), 3.41(3H, s, —OCH$_3$), 5.13-5.39 (1H, anomer proton), 5.86(1H, d, J=4 Hz, anomer proton), 7.23-8.23(5H, aromatic proton)

Compound No. 157

NMR (60 MHz, δ values in CDCl$_3$): 1.16–1.92(3H×4, CH$_3$ ×4), 2.89(3H, s, Ar—CH$_3$), 3.45(3H, s, O—CH$_3$), 5.27(1H, d, J=8 Hz, anomer proton), 5.89(1H, d, J=4 Hz, anomer proton), 7.32–8.26(5H, aromatic proton)

Compound No. 158

NMR (60 MHz, δ values in CDCl$_3$—CD$_3$OD): 1.11 (3H, d, J=7 Hz, CH$_3$), 1.46(3H, d, J=7 Hz, CH$_3$), 2.85(3H, s, Ar—CH$_3$), $$3.00(3H \times 2, s, CH_3-\overset{|}{N}-CH_3),$$

3.39(3H, s, O—CH$_3$), 5.40(1H, d, J=8 Hz, anomer proton), 5.77(1H, d, J=4 Hz, anomer proton), $$5.93(1H, s, -O-\overset{|}{C}H-O-),$$

6.87–8.13(13H, aromatic proton)

Compound No. 159

NMR (60 MHz, δ values in CDCl$_3$—CD$_3$OD): 1.14(3H×2, d, J=7 Hz, CH$_3$×2), 1.26(3H, d, J=7 Hz, CH$_3$), 1.45(3H, d, J=7 Hz, CH$_3$), 2.83(3H, s, Ar—CH$_3$), 3.37(3H, s, O—CH$_3$), 5.30(1H, d, J=8 Hz, anomer proton), 5.83(1H, d, J=4 Hz, anomer proton), $$6.28(1H, s, -O-\overset{|}{C}H-O-),$$

6.86–7.92(9H, aromatic proton)

Compound No. 160

NMR (60 MHz, δ values in CDCl$_3$): 1.14(3H, d, J=7 Hz, CH$_3$), 1.46(3H, d, J=7 Hz, CH$_3$), 2.77(3H, s, Ar—CH$_3$), 3.39(3H, s, O—CH$_3$), 4.96–5.83(5H, anomer proton ×2, —CH=CH$_2$), $$6.06(1H, s, -O-\overset{|}{C}H-O-),$$

7.23–8.66(9H, aromatic proton)

Compound No. 161

NMR (60 MHz, δ values in CDCl$_3$): 1.12(3H, d, J=7 Hz, CH$_3$), 1.46(3H, d, J=7 Hz, CH$_3$), 1.83–2.49(8H, CH$_3$×2, —OH×2), 2.82(3H, s, Ar—CH$_3$), 3.40(3H, s, O—CH$_3$), 5.40(1H, d, J=8 Hz, anomer proton), 5.77(1H, d, J=4 Hz, anomer proton), $$6.03(1H, s, -O-\overset{|}{C}H-O-),$$

6.85–8.30(10H, vinyl proton ×1, aromatic proton ×9)

Compound No. 162

NMR (60 MHz, δ values in CDCl$_3$): 1.10(3H, d, J=7 Hz, CH$_3$), 1.45(3H, d, J=7 Hz, CH$_3$), 2.21(3H, s, —CO—CH$_3$), 2.82(3H, s, Ar—CH$_3$), 3.37(3H, s, O—CH$_3$), 5.30(1H, d, J=8 Hz, anomer proton), 5.72(1H, d, J=4 Hz, anomer proton), $$5.99(1H, s, -O-\overset{|}{C}H-O-),$$

7.20–8.23(9H, aromatic proton)

Compound No. 163

NMR (60 MHz, δ values in CDCl$_3$): 0.89–1.76(3H×4, CH$_3$×4), 2.79(3H, s, Ar—CH$_3$), 3.43(3H, s, O—CH$_3$), 5.33(1H, d, J=8 Hz, anomer proton), 5.69(1H, d, J=4 Hz, anomer proton), $$5.89(1H, s, -O-\overset{|}{C}H-O-),$$

7.17–7.92(9H, aromatic proton)

Compound No. 164

NMR (60 MHz, δ values in CDCl$_3$): 1.31(3H, d, J=7 Hz, CH$_3$), 1.48(3H, d, J=7 Hz, CH$_3$), 2.88(3H, s, Ar—CH$_3$), 3.40(3H, s, O—CH$_3$), 5.31(1H, d, J=8 Hz, anomer proton), 5.92(1H, d, J=8 Hz, anomer proton), $$6.36(1H, s, -O-\overset{|}{C}H-O-),$$

7.15–8.15(10H, aromatic proton)

Compound No. 165

NMR (60 MHz, δ values in CDCl$_3$): 1.30(3H, d, J=7 Hz, CH$_3$), 1.46(3H, d, J=7 Hz, CH$_3$), 2.84(3H, s, Ar—CH$_3$), 3.37(3H, s, O—CH$_3$), 4.53(2H, s, benzyl proton), 5.25(1H, d, J=8 Hz, anomer proton), 5.88(1H, d, J=4 Hz, anomer proton), $$6.30(1H, s, -O-\overset{|}{C}H-O-),$$

7.17–8.00(15H, aromatic proton)

Compound No. 166

NMR (60 MHz, δ values in CDCl$_3$): 1.31(3H, d, J=7 Hz, CH$_3$), 1.47(3H, d, J=7 Hz, CH$_3$), 2.90(3H, s, Ar—CH$_3$), 3.41(3H, s, O—CH$_3$), 5.28(1H, d, J=8 Hz, anomer proton), 5.92(1H, d, J=4 Hz, anomer proton), $$6.35(1H, s, -O-\overset{|}{C}H-O-),$$

7.18–8.15(10H, aromatic proton)

Compound No. 167

NMR (60 MHz, δ values in CDCl$_3$): 1.30(3H, d, J=7 Hz, CH$_3$), 1.46(3H, d, J=7 Hz, CH$_3$), 2.84(3H, s, Ar—CH$_3$), 3.36(3H, s, O—CH$_3$), 5.29(1H, d, J=8 Hz, anomer proton), 5.91(1H, d, J=4 Hz, anomer proton), $$6.33(1H, s, -O-\overset{|}{C}H-O-),$$

7.15–8.45 (15H, aromatic proton)

Compound No. 168

NMR (60 MHz, δ values in CDCl$_3$-CD$_3$OD): 1.30(3H, d, J=7 Hz, CH$_3$), 1.48(3H, d, J=7 Hz, CH$_3$), 2.89(3H, s, Ar—13 CH$_3$), 3.04(3.04(3H, s, —SO$_2$—CH$_3$), 13.37(3H, s, O—CH$_3$), 5.10-6.10(2H, anomer proton x2),

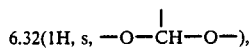
6.32(1H, s, —O—CH—O—), 7.30-8.27(10H, aromatic proton)

Compound No. 169

NMR (60 MHz, δ values in CDCl$_3$): 1.17(3Hx2, d, J=7 Hz, CH$_3$x2), 1.32(3H, d, J=7 Hz, CH$_3$), 1.50(3H, d, J=7 Hz, CH$_3$), 2.92(3H, s, Ar—CH$_3$), 3.46(3H, s, O—CH$_3$), 5.33(1H, d, J=8 Hz, anomer proton), 5.96(1H, d, J=4 Hz, anomer proton),

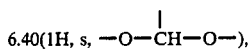
6.40(1H, s, —O—CH—O—), 7.29-8.06(10H, aromatic proton)

Compound No. 170

NMR (60 MHz, δ values in CDCl$_3$—CD$_3$OD): 1.29(3H, d, J=7 Hz, CH$_3$), 1.46(3H, d, J=7 Hz, CH$_3$), 1.56(3Hx3, s, CH$_3$x3), 2.86(3H, s, Ar—CH$_3$), 3.39 (3H, s, O—CH$_3$), 5.31(1H, d, J=8 Hz, anomer proton), 5.90(1H, d, J=4 Hz, anomer proton),

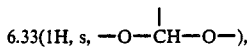
6.33(1H, s, —O—CH—O—), 7.17-8.10(10H, aromatic proton)

Compound No. 171

NMR (60 MHz, δ values in CDCl$_3$): 0.94-1.91(19H, CH$_3$x6, CHx1), 2.87(3H, s, Ar—CH$_3$), 3.40(3H, s, O—CH$_3$), 5.21(1H, d, J=8Hz, anomer proton), 5.85(1H, d, J=4 Hz, anomer proton), 7.15-7.97 (5H, aromatic proton)

Compound No. 172

NMR (60 MHz, δ values in CDCl$_3$): 1.10-1.86(3Hx6, CH$_3$x6), 2.80(3H, s, Ar—CH$_3$), 3.37(3H, s, O—CH$_3$), 5.10-5.93(2H, anomer proton x2), 7.17-8.26(5H, aromatic proton)

Compound No. 173

NMR (60 MHz, δ values in CDCl$_3$): 1.19-2.39(20H, CH$_3$x6, —OHx2), 2.84(3H, s, Ar—CH$_3$), 3.39(3H, s, O—CH$_3$), 5.22(1H, d, J=8 Hz, anomer proton), 5.84(1H, d, J=4 Hz, anomer proton), 7.00-8.00(6H, >C=CH—, aromatic proton x5)

Compound No. 174

NMR (60 MHz, δ values in CDCl$_3$): 1.13-1.79(3Hx4, CH$_3$x4), 2.79(3H, s, Ar—CH$_3$), 3.34(3H, s, O—CH$_3$), 4.10(2H, s, —CO—CH$_2$—S—), 5.13(1H, d, J=8 Hz, anomer proton), 5.73(1H, d, J=4 Hz, anomer proton), 6.96-7.63(10H, aromatic proton)

Compound No. 175

NMR (60 MHz, δ values in CDCl$_3$): 1.13-1.92(3Hx4, CH$_3$x4), 2.83(3H, s, Ar—CH$_3$), 3.40(3H, s, O—CH$_3$), 4.83-6.00(5H, m, anomer proton x2, —CH=CH$_2$), 7.20-8.00(5H, aromatic proton)

Compound No. 176

NMR (60 MHz, δ values in CDCl$_3$): 1.00-1.79(3Hx5, CH$_3$x5), 2.84(3H, s, Ar—CH$_3$), 3.40(3H, s, —OCH$_3$), 5.23(1H, d, J=8 Hz, anomer proton), 5.86(1H, d, J=4 Hz, anomer proton), 7.17-8.13(5H, aromatic proton)

Compound No. 177

NMR (60 MHz, δ values in CDCl$_3$): 0.70-1.87(3Hx4, 2Hx2, CH$_3$x4, —CH$_2$,—CH$_2$—), 2.84(3H, s, Ar—CH$_3$), 3.38(3H, s, O—CH$_3$), 5.20(1H, d, J=8 Hz, anomer proton), 5.83(1H, d, J=4 Hz, anomer proton), 7.10-8.07(5H, aromatic proton)

Compound No. 178

NMR (60 MHz, δ values in CDCl$_3$): 0.66-1.93(18H, CH$_3$x5, CH$_2$x1, CHx1), 2.83(3H, s, Ar—CH$_3$), 3.37(3H, s, O—CH$_3$), 5.15(1H, d, J=8 Hz, anomer proton), 5.78(1H, d, J=4 Hz, anomer proton), 7.16-8.00(5H, aromatic proton)

Compound No. 179

NMR (60 MHz, δ values in CDCl$_3$): 1.15-1.95(3Hx4, CH$_3$x4), 2.87(3H, s, Ar—CH$_3$), 3.41(3H, s, O—CH$_3$), 5.22(1H, d, J=8 Hz, anomer proton), 5.86(1H, d, J=4 Hz, anomer proton), 7.17-8.33(9H, aromatic proton)

Compound No. 180

NMR (60 MHz, δ values in CDCl$_3$): 1.11-1.87(3Hx4, CH$_3$x4), 2.86(3H, s, Ar—CH$_3$), 3.39(3H, s, O—CH$_3$), 5.21(1H, d, J=8 Hz, anomer proton), 5.85(1H, d, J=4 Hz, anomer proton), 7.27-8.57(8H, aromatic proton)

Compound No. 181

NMR (60 MHz, δ values in CDCl$_3$): 1.08-1.84(3Hx4, CH$_3$x4), 2.85(3H, s, Ar—CH$_3$), 3.40(3H, s, O—CH$_3$), 5.23(1H, d, J=8 Hz, anomer proton), 5.86(1H, d, J=4 Hz, anomer proton), 7.29-8.56(9H, aromatic proton)

Compound No. 182

NMR (60 MHz, δ values in CDCl$_3$): 1.08-1.87(3Hx4, CH$_3$x4), 2.89(3H, s, Ar—CH$_3$), 3.43(3H, s, O—CH$_3$), 5.28(1H, d, J=8 Hz, anomer proton), 5.94(1H, d, J=4 Hz, anomer proton), 7.30-8.70(9H, armatic proton)

Compound No. 183

NMR (60 MHz, δ values in CDCl$_3$): 1.24-1.86(3Hx4, CH$_3$x4), 2.86(3H, s, Ar—CH$_3$), 3.40(3H, s, O—CH$_3$), 5.24(1H, d, J=8 Hz, anomer proton), 5.88(1H, d, J=4 Hz, anomer proton), 7.32-8.56(9H, aromatic proton)

Compound No. 184

NMR (60 MHz, δ values in CDCl$_3$): 1.17-1.87(3Hx4, CH$_3$x4), 2.87(3H, s, Ar—CH$_3$), 3.39(3H, s, O—CH$_3$), 3.86(3H, s, Ar—OCH$_3$), 5.03-5.36(1H, anomer proton), 5.70-6.03(1H, anomer proton), 7.07-8.20(9H, aromatic proton)

Compound No. 185

NMR (60 MHz, δ values in CDCl$_3$): 1.10-1.87(3Hx4, CH$_3$x4), 2.88(3H, s, Ar—CH$_3$), 3.40(3H, s, O—CH$_3$), 5.24(1H, d, J=8 Hz, anomer proton), 5.87(1H, d, J=4 Hz, anomer proton), 7.20-8.47(9H, aromatic proton)

Compound No. 186

NMR (60 MHz, δ values in CDCl$_3$): 1.10(3H, d, J=7 Hz, CH$_3$), 1.50(3H, d, J=7 Hz, CH$_3$), 2.86(3H, s, Ar—CH$_3$), 3.40(3H, s, O—CH$_3$), 5.35(1H, d, =8 Hz, anomer proton), 5.82(1H, d, J=4 Hz, anomer proton),

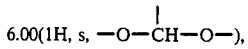
6.00(1H, s, —O—CH—O—), 7.23–8.73 (14H, aromatic proton)

Compound No. 187

NMR (60 MHz, δ values in CDCl$_3$): 1.09(3H, d, J=7 Hz, CH$_3$), 1.51(3H, d, J=7 Hz, CH$_3$), 2.87(3H, s, Ar—CH$_3$), 3.40(3H, s, O—CH$_3$), 5.33(1H, d, J=8 Hz, anomer proton), 5.77(1H, d, J=4 Hz, anomer proton),

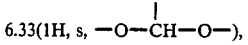
6.33(1H, s, —O—CH—O—), 7.17–8.57(13H, aromatic proton)

Compound No. 188

NMR (60 MHz, δ values in CDCl$_3$): 1.14(3H, d, J=7Hz, CH$_3$), 1.28(3H, t, J=7Hz, CH$_3$), 1.47(3H, d, J=7Hz, CH$_3$), 2.82(3H, s, Ar—CH$_3$), 3.39(3H, s, O—CH$_3$), 5.34(1H, d, J=8Hz, anomer proton), 5.74(1H, d, J=4Hz, anomer proton),

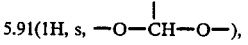
5.91(1H, s, —O—CH—O—), 7.2–8.18(9H, aromatic proton)

Compound No. 189

NMR (60MHz, δ values in CDCl$_3$): 1.16(3H, d, J=7Hz, CH$_3$), 1.49(3H, d, J=7Hz, CH$_3$), 2.83(3H, s, Ar—CH$_3$), 3.38(3H, s, O—CH$_3$), 5.37(1H, d, J=8Hz, anomer proton), 5.72(1H, d, J=4Hz, anomer proton),

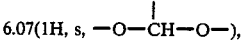
6.07(1H, s, —O—CH—O—), 7.24–8.57(13H, aromatic proton)

Compound No. 190

NMR (60MHz, δ values in CDCl$_3$): 1.13(3H, d, J=7Hz, CH$_3$), 1.37–1.23(3H, CH$_3$), 1.45(3H, d, J=7Hz, CH$_3$), 2.85(3H, s, Ar—CH$_3$), 3.38(3H, s, O—CH$_3$), 5.32(1H, d, J=8Hz, anomer proton), 5.72(1H, d, J=4Hz, anomer proton),

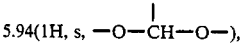
5.94(1H, s, —O—CH—O—), 7.17–8.13(9H, aromatic proton)

As shown in the experimental examples hereinafter described, the compounds of this invention have excellent effects on P-388 leukemia cells.

The antitumor activity, acute toxicity, dose and administration routes of the compounds of this invention are described below.

(1) Antitumor Activity

Into BDF$_1$ mice were inoculated intraperitoneally P-388 leukemia cells at a rate of 1×10$^6$ cells/mouse, and each drug to be tested was administered intravenously on the first, fifth and ninth days after the inoculation. Whether the mice were alive or dead was observed for 30 days, and the ratio of medium survival time of test and control animals (T/C) of each treatment group was calculated, taking the survival period of a control group to which physiological saline was administered as 100. The results obtained are shown in Table 6. The drugs were as follows solutions prepared by adding physiological saline to each of compound Nos. 8, 9, 10, 11, 17, 34, 42, 59, 80 and 134; suspensions prepared by dispersing each of compound Nos. 41, 78, 98, 100, 130, 191, 212, 213, 215, 227 and 230 to 232 and a small amount of sodium carboxymethyl cellulose (Na.CMC) in physiological saline, and suspensions or solutions of each of the other compounds plus a small amount of a surface active agent (e.g., Tween-80) in physiological saline.

TABLE 6

| Compound No. | Dose[1] (mg/kg) | T/C (%) of MST[2] |
|---|---|---|
| 1 | b | 138 |
|   | c | 214 |
| 2 | b | 184 |
|   | c | 216 |
| 3 | b | 150 |
|   | c | 192 |
| 4 | b | 184 |
|   | c | 216 |
| 6 | b | 182 |
|   | c | 242 |
| 8 | b | 186 |
|   | c | 220 |
| 9 | b | 165 |
|   | c | 292 |
| 10 | b | 161 |
|   | c | 197 |
| 11 | b | 186 |
| 12 | b | 203 |
|   | c | 241 |
| 13 | b | 186 |
|   | c | 262 |
| 14 | b | 195 |
| 15 | b | 189 |
| 16 | b | 164 |
|   | c | 242 |
| 17 | b | 206 |
|   | c | 241 |
| 18 | b | 196 |
|   | c | 238 |
| 19 | b | 184 |
|   | c | 233 |
| 20 | b | 203 |
|   | c | 248 |
| 21 | b | 210 |
|   | c | 229 |
| 22 | b | 181 |
| 23 | b | 205 |
|   | c | 233 |
| 24 | b | 161 |
|   | c | 223 |
| 25 | b | 212 |
| 26 | b | 195 |
|   | c | 220 |
| 27 | b | 179 |
| 28 | f | 193 |
|   | h | 227 |
| 29 | c | 173 |
|   | f | 221 |
| 30 | c | 171 |
|   | f | 257 |
| 31 | c | 171 |
|   | f | 238 |
| 32 | a | 146 |
|   | b | 186 |

TABLE 6-continued

| Compound No. | Dose[1] (mg/kg) | T/C (%) of MST[2] |
|---|---|---|
| 33 | a | 157 |
|  | b | 186 |
| 34 | c | 140 |
| 35 | c | 173 |
| 36 | a | 135 |
|  | b | 157 |
| 37 | a | 146 |
| 38 | b | 203 |
| 39 | b | 165 |
|  | c | 214 |
| 40 | f | 205 |
| 41 | c | 157 |
| 42 | f | 187 |
| 43 | b | 226 |
| 44 | c | 164 |
|  | f | 217 |
| 45 | b | 164 |
|  | c | 220 |
| 46 | c | 157 |
|  | f | 210 |
| 47 | c | 150 |
|  | f | 210 |
| 48 | f | 172 |
| 49 | f | 207 |
| 50 | e | 155 |
| 51 | c | 136 |
|  | f | 207 |
| 52 | c | 162 |
|  | f | 203 |
| 53 | c | 165 |
|  | f | 239 |
| 54 | c | 144 |
|  | f | 208 |
| 55 | c | 162 |
| 56 | c | 165 |
|  | f | 219 |
| 57 | c | 162 |
|  | f | 208 |
| 58 | c | 162 |
|  | f | 216 |
| 59 | c | 146 |
|  | f | 218 |
| 60 | b | 176 |
|  | c | 210 |
| 61 | b | 176 |
|  | c | 220 |
| 62 | b | 155 |
|  | c | 210 |
| 63 | d | 150 |
|  | g | 205 |
| 64 | c | 165 |
|  | f | 210 |
| 65 | f | 175 |
| 66 | f | 171 |
| 67 | f | 188 |
| 68 | c | 148 |
|  | f | 210 |
| 69 | b | 179 |
|  | c | 222 |
| 70 | b | 135 |
|  | c | 181 |
| 71 | b | 157 |
| 72 | b | 167 |
| 73 | b | 176 |
|  | c | 229 |
| 74 | b | 186 |
| 75 | b | 153 |
|  | c | 197 |
| 76 | b | 135 |
|  | c | 184 |
| 77 | b | 135 |
|  | c | 186 |
| 78 | c | 146 |
|  | f | 176 |
| 79 | c | 179 |
| 80 | c | 139 |
|  | f | 184 |
| 81 | b | 139 |
|  | c | 173 |
| 82 | c | 148 |
|  | f | 205 |

TABLE 6-continued

| Compound No. | Dose[1] (mg/kg) | T/C (%) of MST[2] |
|---|---|---|
| 83 | c | 144 |
|  | f | 208 |
| 84 | c | 145 |
|  | f | 208 |
| 85 | f | 157 |
| 86 | f | 136 |
| 87 | c | 134 |
|  | f | 183 |
| 88 | d | 157 |
| 89 | f | 173 |
| 90 | b | 162 |
| 91 | c | 173 |
| 92 | b | 146 |
|  | c | 192 |
| 93 | f | 165 |
| 94 | f | 183 |
| 95 | c | 173 |
| 96 | c | 162 |
| 97 | b | 156 |
| 98 | f | 187 |
| 99 | f | 136 |
| 100 | f | 157 |
| 101 | c | 171 |
|  | f | 225 |
| 102 | f | 187 |
| 103 | c | 146 |
|  | f | 203 |
| 104 | c | 137 |
| 105 | f | 216 |
| 106 | b | 173 |
| 107 | c | 139 |
|  | f | 185 |
| 108 | d | 163 |
| 109 | e | 145 |
| 110 | c | 154 |
| 111 | e | 175 |
| 112 | d | 148 |
| 113 | c | 138 |
| 114 | c | 130 |
| 115 | b | 135 |
| 116 | c | 130 |
| 117 | c | 135 |
| 118 | c | 135 |
| 119 | c | 153 |
| 120 | c | 148 |
| 121 | c | 146 |
| 122 | c | 135 |
| 123 | c | 135 |
| 124 | f | 151 |
| 125 | d | 140 |
| 126 | f | 150 |
| 127 | b | 130 |
| 128 | d | 146 |
| 129 | i | 167 |
| 130 | i | 141 |
| 131 | f | 148 |
| 132 | c | 136 |
|  | f | 146 |
| 133 | f | 139 |
| 134 | a | 192 |
|  | b | 175 |
| 135 | b | 167 |
| 147 | b | 214 |
| 148 | b | 185 |
|  | c | 250 |
| 149 | b | 203 |
| 150 | b | 200 |
|  | c | 205 |
| 151 | b | 155 |
|  | c | 224 |
| 152 | b | 157 |
|  | c | 210 |
| 153 | b | 203 |
|  | c | 243 |
| 154 | b | 205 |
|  | c | 214 |
| 155 | b | 171 |
|  | c | 183 |
| 156 | c | 160 |
|  | f | 218 |
| 157 | c | 153 |

TABLE 6-continued

| Compound No. | Dose[1] (mg/kg) | T/C (%) of MST[2] |
|---|---|---|
| | f | 201 |
| 158 | c | 174 |
| | f | 205 |
| 159 | c | 171 |
| | f | 216 |
| 160 | c | 160 |
| | f | 218 |
| 161 | c | 169 |
| | f | 234 |
| 162 | c | 157 |
| | f | 243 |
| 163 | c | 156 |
| | f | 227 |
| 164 | b | 198 |
| 165 | b | 189 |
| 166 | a | 138 |
| 167 | b | 198 |
| 168 | b | 167 |
| 169 | b | 202 |
| 170 | b | 198 |
| 171 | c | 186 |
| | f | 212 |
| 172 | c | 148 |
| | f | 195 |
| 173 | c | 152 |
| | f | 192 |
| 174 | c | 148 |
| | f | 198 |
| 175 | c | 145 |
| | f | 208 |
| 176 | c | 155 |
| | f | 208 |
| 177 | c | 153 |
| | f | 208 |
| 178 | c | 142 |
| | f | 181 |
| 179 | c | 136 |
| | f | 208 |
| 180 | c | 145 |
| | f | 208 |
| 181 | c | 145 |
| | f | 208 |
| 182 | c | 153 |
| | f | 192 |
| 183 | c | 153 |
| | f | 192 |
| 184 | c | 162 |
| | f | 199 |
| 185 | c | 142 |
| | f | 192 |
| 186 | c | 176 |
| 187 | c | 130 |
| | f | 216 |
| 188 | c | 193 |
| 189 | c | 146 |
| | f | 214 |
| 190 | c | 145 |
| | f | 208 |
| 191 | b | 155 |
| 192 | a | 153 |
| | b | 199 |
| 193 | a | 162 |
| 194 | b | 130 |
| | c | 192 |
| 195 | c | 165 |
| 196 | c | 208 |
| 197 | c | 144 |
| | f | 171 |
| 198 | c | 176 |
| 199 | d | 159 |
| 200 | c | 168 |
| 201 | c | 162 |
| 202 | c | 174 |
| 203 | e | 180 |
| 204 | c | 174 |
| 205 | c | 153 |
| | f | 173 |
| 206 | c | 139 |
| | f | 180 |
| 207 | c | 130 |
| | f | 192 |

TABLE 6-continued

| Compound No. | Dose[1] (mg/kg) | T/C (%) of MST[2] |
|---|---|---|
| 208 | c | 136 |
| | f | 192 |
| 209 | c | 134 |
| | f | 192 |
| 210 | c | 186 |
| 211 | f | 176 |
| 212 | f | 153 |
| 213 | f | 160 |
| 214 | c | 130 |
| | f | 198 |
| 215 | c | 131 |
| | f | 158 |
| 216 | c | 171 |
| 217 | f | 181 |
| 218 | f | 176 |
| 219 | c | 130 |
| | f | 182 |
| 220 | d | 157 |
| 221 | f | 168 |
| 222 | c | 144 |
| | f | 162 |
| 223 | e | 172 |
| 224 | d | 148 |
| 225 | e | 148 |
| 226 | c | 145 |
| 227 | f | 143 |
| 228 | e | 140 |
| 229 | e | 167 |
| 230 | f | 144 |
| 231 | b | 150 |
| 232 | a | 146 |
| 233 | e | 165 |
| 234 | c | 135 |
| 235 | c | 145 |
| 236 | c | 145 |
| 237 | e | 242 |
| 238 | c | 130 |
| | f | 192 |
| 239 | e | 153 |
| 240 | e | 158 |
| 241 | f | 135 |
| 242 | b | 137 |

Note:
[1]Symbols a to i denote the following doses:
a: 10 mg/kg × 3
b: 20 mg/kg × 3
c: 40 mg/kg × 3
d: 50 mg/kg × 3
e: 60 mg/kg × 3
f: 80 mg/kg × 3
g: 100 mg/kg × 3
h: 120 mg/kg × 3
i: 160 mg/kg × 3
[2]Ratio of medium survival time of test and control animals.

For comparison, the same treatment as described above was carried out using, at a dose of 50 mg/kg/day × 3, a chartreusin suspension prepared by the preparation method described in "Cancer Research, Vol. 37, p. 1666–1672 (1977)" [a method comprising dissolving chartruesin in a mixed solution of 0.2M $Na_2HPO_4$ and N,N-dimethylacetamide (4:1 by volume) at a concentration of 5 mg/ml]. In this case, T/C (%) was calculated as 105%.

(2) Acute Toxicity

In Table 7 are shown acute toxicity values ($LD_{50}$, mg/kg) in ddY mice in the case of intravenously administering (once) each of the compounds of this invention in the form of preparations shown in the Preparation Examples shown in Table 7.

TABLE 7

| Compound No. | Preparation Example No. | $LD_{50}$ (mg/kg) |
|---|---|---|
| 166 | 1 | 30 or more |

TABLE 7-continued

| Compound No. | Preparation Example No. | LD$_{50}$ (mg/kg) |
|---|---|---|
| 27, 37, 90, 97, 116, 117, | 3 | |
| 14 | 7 | |
| 15 | 11 | |
| 34, 134 | 18 | |
| 147 | 1 | 40 or more |
| 19, 26, 72, 74, 113, 115, 123, 135 | 2 | |
| 12, 13, 20–25, 38, 39, 43, 55, 60–62, 69–71, 73, 75–77, 79, 81, 91, 92, 95, 96, 106, 114, 118, 119, 121, 122, 127, 148–155, 159, 164, 167–170, 192–195, 216, 234, 242. | 3 | |
| 120 | 5 | |
| 35 | 7 | |
| 32, 36 | 10 | |
| 2–4, 16 | 12 | |
| 33 | 13 | |
| 6, 18 | 14 | |
| 191, 231, 232 | 15 | |
| 1, 8–11, 17 | 19 | |
| 199, 220, 224 | 4 | 60 or more |
| 67, 110, 202, 210 | 5 | |
| 65, 66, 188, 201, 203, 204, 223, 225, 228, 233, 235, 237, 239, 240 | 6 | |
| 29, 30, 31, 44–46, 52–54, 56, 58, 68, 83, 84, 89, 93, 94, 101, 156, 157, 160–163, 174, 176, 180, 184, 197, 221 | 5 | 80 or more |
| 47, 57, 64, 82, 103–105, 124, 158, 171–173, 175, 177–179, 181–183, 185–187, 189, 190, 196, 198, 200, 205, 206, 207–209, 211, 214, 217–219, 222, 229, 236, 238, 241 | 6 | |
| 212, 213, 215, 227, 230 | 16 | |
| 80 | 19 | |
| 112 | 2 | 100 or more |
| 88, 109, 111, 125, 126, 128 | 4 | |
| 40, 50, 51, 85, 87, 107, 132, 133 | 5 | |
| 86, 102, 131 | 6 | |
| 108 | 8 | |
| 41, 78, 98, 99 | 17 | |
| 59 | 19 | |
| 42 | 20 | |
| 28 | 5 | 120 or more |
| 63 | 8 | |
| 48 | 9 | |
| 49 | 5 | 150 or more |
| 129 | 6 | 180 or more |
| 100, 130 | 17 | |

(3) Doses and Administration Routes

As to administration routes in the case of animals, the compounds of this invention are administered as injections such as intraperitoneal injection, intravenous injection, local injection and the like, or as oral drugs. In the case of human beings, said compounds are administered as injections such as intravascular (intravenous or intraarterial) injection, local injection and the like, or as oral drugs, suppositories or the like. As to the dose, said compounds are administered continuously or intermittently in a range in which the total dose does not exceed a certain level, in consideration of the results of animal experiments and various conditions. However, the dose may, of course, be properly varied depending on the administration route, and on the conditions of a patient or an animal to be treated (for example, age, body weight, sex, sensitivity, food and the like), interval of administration, drugs used in combination with said compounds and the degree of disease. An optimum dose and the number of administrations under certain conditions should be determined by medical specialists. The autitumorous composition of this invention are prepared in the same manner as for conventional drugs. For example, they are prepared from an active ingredient and various pharmacologically acceptable adjuvants such as inactive diluent and the like. Intravenous administration.of these antitumorous composition is most suitable. The content of active ingredient in the antitumorous compositions of this invention may vary depending on various conditions and cannot be determined uniquely. It is sufficient that the active ingredient is contained similarly to the case of conventional antitumorous compositions. For example, the active ingredient may be contained in an amount of at least 0.001%.

Next, preparation Examples of the antitumorous compositions of this invention are described below.

PREPARATION EXAMPLE 1

With 2.0 mg of yellow powder of the exo form of 6-O-(N-trifluoroacetyl-β-amino-isobutyryl)-3',4'-O-(m-fluorobenzylidene)-chartreusin (compound No. 37) was sufficiently mixed 0.16 ml of Tween-80, after which 2.0 ml of physiological saline was added in small portions to prepare a solution.

PREPARATION EXAMPLE 2

With 5.2 mg of yellow powder of the exo form of 6-O-(N-trifluoroacetyl-2-amino-cyclohexanecarbonyl)-3',4'-O-benzylidene-chartreusin (compound No. 26) was sufficiently mixed 0.20 ml of Tween-80, after which 2.5 ml of physiological saline was added in small portions to prepare a solution.

PREPARATION EXAMPLE 3

With 5.2 mg of yellow powder of the exo-form of 6-O-(N-trifluoroacetyl-β-amino-isobutyryl)-3',4'-O-benzylidene-chartreusin (compound No. 12) was sufficiently mixed 0.20 ml of Tween-80, after which 2.5 ml of physiological saline was added in small portions to prepare a suspension.

PREPARATION EXAMPLE 4

With 6.5 mg of yellow powder of 6-O-(3-benzoylpropionyl)-3',4'-O-isopropylidene-chartreusin (compound No. 224) was sufficiently mixed 0.20 ml of Tween-80, after which 2.5 ml of physiological saline was added in small portions to prepare a suspension.

PREPARATION EXAMPLE 5

With 10.4 mg of yellow powder of the endo-form of 6-O-(N-trifluoroacetyl-β-alanyl)-3',4'-O-benzylidene-chartreusin (compound No. 131) was sufficiently mixed 0.20 ml of Tween-80, after which 2.5 ml of physiological saline was added in small portions to prepare a solution.

PREPARATION EXAMPLE 6

In the same manner as in Preparation Example 5, the endo form of 6-O-(N-benzoyl-β-alanyl)-3',4'-O-(m-fluorobenzylidene)-chartreusin (compound No. 47) was formed into a suspension.

PREPARATION EXAMPLE 7

With 7.6 mg of yellow powder of the exo form of 6-O-(α-isopropyl-β-alanyl)-3',4'-O-benzylidene-chartreusin phosphate (compound No. 35) was sufficiently mixed 0.19 ml of Tween-80, after which 3.8 ml of physiological saline was added in small portions to prepare a solution.

PREPARATION EXAMPLE 8

With 10 mg of yellow powder of 6-O-(N-carbobenzyloxyglycyl)-3',4'-O-isopropylidene-chartreusin (compound No. 108) was sufficiently mixed 0.1 ml of Tween-80, after which 1.9 ml of physiological saline was added in small portions to prepare a suspension.

PREPARATION EXAMPLE 9

With 20 mg of yellow powder of 6-O-(N-formyl-β-alanyl)-3',4'-O-isopropylidene-chartreusin (compound No. 48) was sufficiently mixed 0.2 ml of Tween-80, after which 1.8 ml of physiological saline was added in small portions to prepare a solution.

PREPARATION EXAMPLE 10

With 3.2 mg of yellow powder of the exo form of 6-O-(glycyl-glycyl-valyl)-3',4'-O-benzylidene-chartreusin phosphate (compound No. 36) was sufficiently mixed 0.04 ml of Tween-80, after which 1.6 ml of physiological saline was added in small portions to prepare a solution.

PREPARATION EXAMPLE 11

With 3.2 mg of yellow powder of the exo form of 6-O-(N,N-diethyl-β-alanyl)-3',4'-O-(m-fluorobenzylidene)-chartreusin hydrochloride (compound No. 15) was sufficiently mixed 0.03 ml of Tween-80, after which 1.6 ml of physiological saline was added in small portions to prepare a solution.

PREPARATION EXAMPLE 12

To 7.6 mg of yellow powder of the exo form of 6-O-(β-alanyl)-3',4'-O-(m-fluorobenzylidene)-chartreusin phosphate (compound No. 16) were added 0.06 ml of Tween-80 and 3.8 ml of physiological saline to form a solution.

PREPARATION EXAMPLE 13

With 7.6 mg of yellow powder of the exo form of 6-O-(glycyl-β-alanyl)-3',4'-O-(m-fluorobenzylidene)-chartreusin phosphate (compound No. 33) was sufficiently mixed 0.11 ml of Tween-80, after which 1.9 ml of physiological saline was added in small portions to prepare a solution.

PREPARATION EXAMPLE 14

With 13.8 mg of yellow powder of the exo form of 6-O-(β-amino-isobutyryl)-3',4'-O-benzylidene-chartreusin phosphate (compound No. 6) was sufficiently mixed 0.07 ml of Tween-80, after which 2.3 ml of physiological saline was added in small portions to prepare a solution.

PREPARATION EXAMPLE 15

With 6.4 mg of yellow powder of the exo form of 6-O-(n-butyryl)-3',4'-O-benzylidene-chartreusin (compound No. 191) was sufficiently mixed 16 mg of sodium carboxymethyl cellulose, after which 3.2 ml of physiological saline was added in small portions to obtain a suspension.

PREPARATION EXAMPLE 16

With 12.8 mg of yellow powder of the endo form of 6-O-(n-butyryl)-3',4'-O-benzylidene-chartreusin (compound No. 212) was sufficiently mixed 16 mg of sodium carboxymethyl cellulose, after which 3.2 ml of physiological saline was added in small portions to prepare a suspension.

PREPARATION EXAMPLE 17

With 16 mg of yellow powder of 6-O-(N-trifluoroacetyl-6-amino-n-hexanoyl)-3',4'-O-benzylidene-chartreusin (compound No. 78) was sufficiently mixed 10 mg of sodium carboxymethyl cellulose, after which 2 ml of physiological saline wa added in small portions to prepare a suspension.

PREPARATION EXAMPLE 18

To 3.2 mg of yellow powder of the exo form of 6-O-(β-1-pyrrolidinyl-propionyl)-3',4'-O-(m-fluorobenzylidene)-chartreusin phosphate (compound No. 34) was added 1.6 ml of physiological saline to form a solution.

PREPARATION EXAMPLE 19

To 10.4 mg of yellow powder of the endo form of 6-O-(β-alanyl)-3',4'-O-benzylidene-chartreusin hydrochloride (compound No. 80) was added 2.6 ml of physiological saline to form a solution.

PREPARATION EXAMPLE 20

To 16 mg of 6-O-(β-alanyl)-3',4'-O-isopropylidene-chartreusin hydrochloride (compound No. 42) was added 2 ml of physiological saline to form a solution.

PREPARATION EXAMPLE 21

In 0.07 ml of dimethylformamide was dissolved 18 mg of yellow powder of the exo form of 6-O-(N-trifluoroacetyl-β-amino-isobutyryl-3',4'-O-benzylidene-chartreusin (compound No. 12), followed by adding thereto 0.11 ml of Tween-80 and 0.33 ml of a mixture of HCO-60 and propylene glycol (2:1). After they were sufficiently mixed, 2.50 ml of physiological saline was added thereto to prepare a solution.

PREPARATION EXAMPLE 22

With 9.6 mg of yellow powder of 6-O-(N-trifluoroacetyl-β-alanyl)-3',4'-O-isopropylidene-chartreusin (compound No. 49) was sufficiently mixed 12 mg of mannitol, after which 1.2 ml of physiological saline was added in small portions to prepare a suspension.

What is claimed is:

1. A chartreusin derivative fo the formula (I) or a salt thereof:

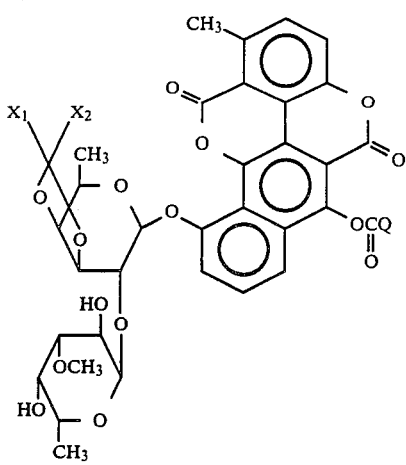

(I)

wherein
$X_1$ is a hydrogen atom or a $C_{1-3}$ alkyl group which may be substituted by a halogen atom, a $C_{1-2}$ alkoxy group, or a $C_{1-2}$ alkylthio group;

$X_2$ is a $C_{1-3}$ alkyl group which may be substituted by a halogen atom or a $C_{1-2}$ alkoxy group or a $C_{1-2}$ alkylthio group, a $C_{1-2}$ alkylcarbonyl-$C_{1-2}$ alkyl group which may be substituted by a halogen atom, a pheynyl group, a phenyl-$C_{1-2}$ alkyl group, a furyl group, or a thienyl group wherein each of the phenyl group, the phenyl-$C_{1-2}$ alkyl group, the furyl group and the thienyl group may be subsituted by a halogen atom, a cyano group, a nitro group, a $C_{1-3}$ alkyl group, a $C_{1-3}$ alkoxy group, a $C_{1-3}$ alkylthio group, a $C_{1-3}$ alkycarbonyl group, a $C_{1-3}$ alkoxycarbonyl group or a di-$C_{1-3}$ alkylamino group wherein each of the $C_{1-3}$ alkyl group, the $C_{1-3}$ alkoxy group, the $C_{1-3}$ alkylthio group, the $C_{1-3}$ alkylcarbonyl group, the $C_{1-3}$ alkoxycarbonyl group and the di-$C_{1-3}$ alkylamino group may be substituted by a halogen atom;

in the case where both $X_1$ and $X_2$ are said alkyl groups, the total number of carbon atoms of these alkyl groups is 4 or less;

$X_1$ is a hdyrogen atom in the case where $X_2$ is said phenyl group, said phenyl-$C_{1-2}$ alkyl group, said furyl group, or said thienyl group;

$X_1$ and $X_2$, when taken together with the adjacent carbon atom, may form a $C_{3-7}$ cycloalkylidene which may be substituted by a halogen atom, a $C_{1-2}$ alkoxy group or a $C_{1-2}$ alkylthio group; and Q is

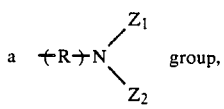 group,

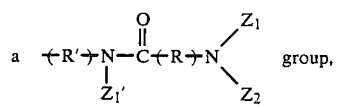 group,

-continued

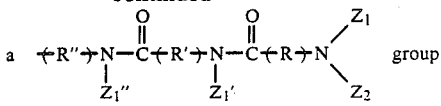 group wherein each of R, R' and R'' is a $C_{1-11}$ alkanediyl group, a $C_{2-11}$ alkenediyl group, a $C_{2-11}$ alkynediyl group, a $C_{3-10}$ cycloalkanediyl group, a $C_{5-10}$ cycloalkenediyl group wherein each of the $C_{1-11}$ alkanediyl group, the $C_{2-11}$ alkenediyl group, the $C_{2-11}$ alkynediyl group, the $C_{3-10}$ cycloalkanediyl group and the $C_{5-10}$ cycloalkenediyl group may be substituted by a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be sbustituted by a halogen atom or a hydroxyl group or a mercapto group or a $C_{1-3}$ alkoxy group or a $C_{1-3}$ alkylthio group, or a 3-indolyl group which may be substittued by a halogen atom, or each of R, R' and R'' is a phenylene group which may be substituted by a halogen atom, a hydroxyl group, a mercapto group, a $C_{1-6}$ alkoxy group, a $C_{1-6}$ alkylthio group, a $C_{1-6}$ alkylsulfinyl group, a $C_{1-6}$ alkylsulfonyl group, an aminocarbonyl group, a hydroxycarbonyl group, or a $C_{1-5}$ alkoxycarbonyl group;, atom, or each of $Z_1$, $Z'_1$ and $Z''_1$ is a hydrogen atom, on a $C_{1-6}$ alkyl group which may be substituted by a halogen atom, a hydroxyl group, a mercapto group, a $C_{1-3}$ alkoxy group, or a $C_{1-3}$ alkylthio group;

$Z_2$ is a hydrogen atom, a formyl group, a $C_{1-6}$ alkyl group, a $C_{1-6}$ alkylcarbonyl group, a benzoyl group wherein each of the $C_{1-6}$ alkyl group, the $C_{1-6}$ alkylcarbonyl group and the benzoyl group may be substituted by the same substituent as substituent for said $C_{1-6}$ alkyl group as each of $Z_1$, $Z'_1$ and $Z''_1$, or $Z_2$ is a benzyloxycarbonyl group which may be substituted by a halogen atom;

$Z_1$ and $Z_2$, when taken together with the nitrogen atom, may form a nitrogen-containing $C_{2-10}$ heterocyclic group which may be substituted by the same substituent as substituent for said $C_{1-6}$ alkyl group as each of $Z_1$, $Z'_1$ and $Z''_1$, or Q is a $C_{1-11}$ alkyl group, a $C_{2-11}$ alkenyl group, a $C_{3-11}$ alkynyl group, a $C_{3-10}$ cycloalkyl group, a $C_{5-10}$ cycloalkenyl group, a $C_{1-10}$ alkylcarbonyl group, a $C_{1-10}$ alkoxycarbonyl group wherein each of the $C_{1-11}$ alkyl group, the $C_{2-11}$ alkenyl group, the $C_{3-11}$ alkynyl group, the $C_{3-10}$ cycloalkyl group, the $C_{5-10}$ cycloalkenyl group, the $C_{1-10}$ alkylcarbonyl group and the $C_{1-10}$ alkoxycarbonyl group may be substituted by a halogen atom a hydroxyl group, a mercapto group, a cyano group, a nitro group, a $C_{1-6}$ alkoxy group, a $C_{1-6}$ alkylthio group, a $C_{1-6}$ alkylsulfinyl group, a $C_{1-6}$ alkylsulfonyl group, a $C_{1-6}$ alkylcarbonyl group, a $C_{1-6}$ alkoxycarbonyl group, a phenoxycarbonyl group, a $C_{1-6}$ alkylcarbonyloxy group, a $C_{3-7}$ cycloakyl group, a phenyl group, a phenoxy group, a phenylthio group, a phenylsulfinyl group, a phenylsulfonyl group, a benzoyl group, a benzolyoxy group or a benzyloxy group wherein each of the $C_{1-6}$ alkoxy group, the $C_{1-6}$ alkylthio group, the $C_{1-6}$ alkylsulfinyl group, the $C_{1-6}$ alkylsulfonyl group, the $C_{1-6}$ alkylcarbonyl group, the $C_{1-6}$ alkoxycarbonyl group, the phenoxycarbonyl group, the $C_{1-6}$ alkylcarbonyloxy group, the $C_{3-7}$ cycloalkyl group, the phenyl group, the phenyoxy group, the phenylthio group, the phenylsulfinyl group, the phenylsulfonyl group, the benzoyl group, the benzoyloxy group, and benzyloxy group may be substituted by the same substituent as substituted for said $C_{1-6}$ alkyl group as each of $Z_1$, $Z'_1$, and $Z_1''$, or Q is a phenyl group which may be substituted by a halogen atom, a hydroxyl group, a mercapto group, a cyano group, a nitro group, a $C_{1-6}$ alkylsulfinyl group, a $C_{1-6}$ alkylsulfonyl group, a $C_{1-6}$ alkyl group, a $C_{1-6}$ alkoxy group, a $C_{1-6}$ alkylthio group, a $C_{1-6}$ alkylcarbonyl group, a $C_{1-6}$ alkoxycarbonyl group, or a $C_{1-6}$ alkylcarbonyloxy group wherein each of the $C_{1-6}$ alkyl group, the $C_{1-6}$ alkoxy group, the $C_{1-6}$ alkylthio group, the $C_{1-6}$ alkylcarbonyl group, the $C_{1-6}$ alkoxycaronyl group, and the $C_{1-6}$ alkylcarbonyloxy group may be substituted by the same substituent as substituent for said $C_{1-6}$ alkyl group as each of $Z_1$, $Z'_1$ and $Z_1''$, the total number of atoms of Q other than hydrogen atom being 30 or less.

2. A chartreusin derivative or a salt thereof according to claim 1 wherein Q is

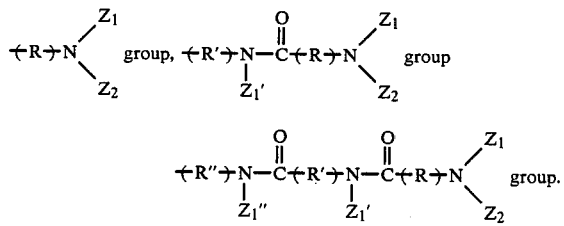

3. A chartreusin derivative or a salt thereof according to claim 1 wherein $X_1$ is a hydrogen atom; $X_2$ is said phenyl group, said furyl group, or said thienyl group; each of R, R' and R" is said $C_{1-11}$ alkanediyl group or said $C_{3-10}$ cycloalkanediyl group; and the total number of atoms of Q other than hydrogen atom is 20 or less.

4. A chartreusin derivative or a salt thereof according to claim 3, wherein $X_2$ is said phenyl group.

5. A chartreusin derivative or a salt thereof according to calim 4 wherein $X_2$ is said phenyl group which may be substituted in the o-position, the m-position or the o-, m-positions of the benzene nucleus; and the total number of atoms of Q other than hydrogen atom is 15 or less.

6. A chartreusin derivative or a salt thereof acording to claim 5, which is in exo form.

7. A chartreusin derivative or salt thereof according to claim 6, wherein $X_2$ is a phenyl group which may be substituted by a fluorine atom in the m-position of the benzene nucleus.

8. A chartreusin derivative or salt thereof according to claim 78 wherein $X_2$ is a phenyl group.

9. A chartreusin derivative according to claim 1, wherein Q is said $C_{1-11}$ alkyl group, said $C_{2-11}$ alkenyl group, said $C_{3-11}$ alknyl group, said $C_{3-10}$ cycloalkyl group, said $C_{5-10}$ cycloalkenyl group, said $C_{1-10}$ alkylcarbonyl group, said $C_{1-10}$ alkoxycarbonylgroup or said phenyl group.

10. A chartreusin derivative according to claim 1, wherein $X_1$ is a hydrogne atom; $X_2$ is said phenyl group, said furyl group, or said thienyl group; and Q is said $C_{1-11}$ alkyl group, said $C_{2-11}$ alkenyl group, said $C_{3-10}$ cycloalkyl group or said phenyl group, the total number of atoms of Q other than hydrogen atom being 20 or less.

11. A chartreusin derivative according to claim 10, wherein $X_2$ is said phenyl group; Q is said $C_{1-11}$ alkyl group or said $C_{3-10}$ cycloalkyl group.

12. A chartreusin derivative according to claim 11, wherein $X_2$ is said phenyl group which may be substituted in the o-position, m-position, or o-, m-positions of the benzene nucleus; and the total number of atoms of Q other than hydrogen atom is 15 or less.

13. A chartreusin derivative according to claim 12, which is in the exo form.

14. A chartreusin derivative according to claim 13 wherein $X_2$ is a phenyl group which may be substituted by a flourine atom in the m-position for the benzene nucleus.

15. A chartreusin derivative according to claim 14, wherein $X_2$ is phenyl group.

16. A chartreusin derivative or a salt thereof ccording to claim 2, wherein the derivative is the exo form of 6-O-(N,N-dimethyl-$\beta$-amino-isobutyryl)-3', 4'-O-benzylidene-chartreusin.

17. A chartreusin derivative or a salt thereof according to claim 2, wherein the derivative is the exo form of 6-O-(N-isopropyl-$\beta$-amino-isobutyryl)-3', 4'-O-benzylindene-chartreusin.

18. A chartreusin derivative or a salt thereof according to claim 2, wherein the derivative is the exo form of 6-O-(N-glycyl-$\beta$-amino-isobutyryl)-3',4'-O-benzylidene-chartreusin.

19. A chartreusin derivative or a salt thereof according,to claim 2, wherein the derivative is the exo form of 6-O-[N-(N',N'-dimethyl-glycyl)-]-amino-isobutyryl]-3',4'-O-benzylidene-chartreusin.

20. A chartreusin derivative or a salt thereof 6-O-($\beta$-amino-isobutyryl)-3',"-O- enzylidene-chartreusin. according to claim 2, wherein the derivative is the exo form of 6-O-($\beta$-amino-isobutryl)3',4'-O-benzylidene-chartreusin.

21. Achartreusin derivative or a salt thereof according to claim 2, wherein the derivative is the exo form of 6-O-(N,N-diethyl-$\beta$-alanyl)-3', 4'-O-benzylidene-chartreusin.

22. A chartreusin derivative or a salt thereof according to claim 2, wherein the derivative is the exo form of 6-O-($\beta$-1-pyrrolidinyl-propionyl)-3',4'-O-benzylidene-chartreusin.

23. A chartreusin derivative or a salt thereof according to claim 2, wherein the derivative is the exo form of 6-O-(N-glycyl-β-alanyl)-3',4'-O-benzylidene-chartreusin.

24. A chartreusin derivative according to claim 2, wherein the derivative is the exo form of 6-O-(N-trifluoroacetyl-β-amino-isobutyrl)-3',4'-O-benzylidene-chartreusin.

25. A chartreusin derivative according to claim 2, wherein the derivative is the exo form of 6-O-(N-benzoyl-β-aminoisobutyryl)-3',4'-O-benzylidene-chartreusin.

26. A chartreusin derivative or a salt thereof according to claim 2, wherein the derivative is the exo form of 6-O-(β-amino-isobutyryl)-3',4',-O-(m-fluorobenzylidene)-chartreusin.

27. A chartreusin derivative or a salt thereof according to claim 2, wherein the derivative is the exo form of 6-O-(β-alanyl)-3',4'-O-benzylidene-chartreusin.

28. A chartreusin derivative or a salt thereof according to claim 2, wherein the derivative is the exo form of 6-O-(β-morpholino-propionyl)-3',4'-O-benzylidene-chartreusin.

29. A chartreusin derivative or a salt thereof according to claim 2, wherein the derivative is the exo form of 6-O-(N,N-dimethyl-α-ethyl-propionyl)-3',4'-O-benzylindene-chartreusin.

30. A chartreusin derivative or a salt thereof according to claim 2, wherein the derivative is the exo form of 6-O-(N,N-dimetyl-β-alanyl)-3',4'-O-benzylidene-chartreusin.

31. A chartreusin derivative or a salt thereof according to claim 2, wherein the derivative is the exo form of 6-O-(N-methyl-β-amino-isobutyryl)-3',4'-O-benzylidene-chartreusin.

32. A chartreusin derivative or a salt thereof according to claim 2, wherein the derivative is the exo form of 6-O-(N-methyl-β-alanyl)-3',4'-O-benzylidene-chartreusin.

33. A chartreusin derivative according to claim 9, wherein the, derivative is the exo form of 6-O-(4-hydroxy-n-butyryl)-3',4'-O-benzylidene-chartreusin.

34. A chartreusin derivative according to claim 9, wherein the derivative is the exo form of 6-O-(2-acetoxyacetyl)-3', 4'-O-benzylidene-chartreusin.

35. A chartreusin derivative according to claim 9, wherein the derivative is the exo form of 6-O-[2-(3-chloropropionyloxy)-acetyl]-3',4'-O-benzylidene-chartreusin.

36. A chartreusin derivative according to claim 9, wherein the derivative is the exo form of 6-O-(3-methanesulfinyl-propionyl)-3',4'-O-benzylidene-chartreusin.

37. A chartreusin derivative according to claim 9, wherein the derivative is the exo form of 6-O-(3-methylcarbonylpropionyl)-3', 4'-O-benzylidene-chartreusin.

38. A chartreusin derivative according to claim 9, wherein the derivative is the exo form of 6-O-(3-phenylpropionyl)-3', 4'-O-benzylidene-chartreusin.

39. A chartreusin derivative according to claim 9, wherein the derivative is the exo form of 6-O-(3-methyl-n-butyryl)-3',4'-O-benzylidene-chartreusin.

40. A chartreusin derivative, as an intermediate, of the formula:

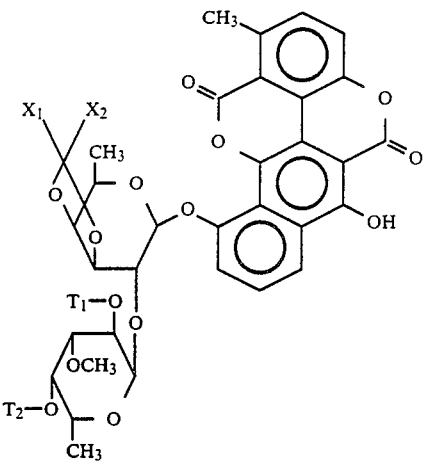

wherein
$X_1$ is a hydrogen atom or a $C_{1-3}$ alkyl group which may be substituted by a halogen atom, a $C_{1-2}$ alkoxy group, or a $C_{1-2}$ alkylthio group;

$X_2$ is
 a $C_{1-3}$ alkyl group which may be substituted by a halogen atom or a $C_{1-2}$ alkoxy group or a $C_{1-2}$ alkylthio group,
 a $C_{1-2}$ alkylcarbonyl-$C_{1-2}$ alkyl group which may be substituted by a halogen atom,
 a phenyl group,
 a phenyl-$C_{1-2}$ alkyl group,
 a furyl group or
 a thienyl group
  wherein each of the phenyl group, the phenyl-$C_{1-2}$ alkyl group, the fury group and the thienyl group may be substituted by a halogen atom, a cyano group, a nitro group, a $C_{1-3}$ alkyl group, a $C_{1-3}$ alkoxy group, a $C_{1-3}$ alkylthio group, a $C_{1-3}$ alkycarbonyl group, a $C_{1-3}$ alkoxycarbonyl group or a di-$C_{1-3}$ alkylamino group
  wherein each of the $C_{1-3}$ alkyl group, the $C_{1-3}$ alkoxy group, the $C_{1-3}$ akylthio group, the $C_{1-3}$ alkylcarbonyl group, the $C_{1-3}$ alkoxycarbonyl group and the di-$C_{1-3}$ akylamino group may be substituted by a halogen atom;

in the case where, both $X_1$ and $X_2$ are said alkyl groups, the total number of carbon atoms of these alkyl groups is 4 or less;

$X_1$ is a hydrogen atom in the case where $X_2$ is said phenyl group, said phenyl-$C_{1-2}$ alkyl group, said furyl group, or said thienyl group;

$X_1$ and $X_2$, when taken together with the adjacent carbon atom, may form a $C_{3-7}$ cycloalkylidene which may be substituted by a halogen atom, a $C_{1-2}$ alkoxy group or a $C_{1-2}$ alkylthio group;

each of $T_1$ and $T_2$ is a hydrogen atom or a silyl group substituted by a text-butyl dimetyl group, $T_1$ being said silyl group in the case where $T_2$ is said silyl group.

41. A chartreusin derivative as an intermediate according to claim 40, wherein both $T_1$ and $T_2$ are hydrogen atoms.

42. A chartreusin derivative as an intermediate according to claim 40 wherein $X_1$ is a hydrogen atom; $X_2$ is said phenyl group, said furyl group, or said thienyl group.

43. A chartreusin derivative as an intermediate according to claim 42, wherein $X_2$ is said phenyl group.

44. A chartreusin derivative as an intermediate according to claim 43, which is in the exo form and wherein $X_2$ is said phenyl group which may be substituted in the o-position, m-position or o-,m-positions of the benzene nucleus.

45. A chartreusin derivative as an intermediate according to claim 44 wherein $X_2$ is said phenyl group which may be substituted in the m-position of the benzene nucleus.

46. A chartreusin derivatie as an intermediate according to claim 45 wherein $X_2$ is a phenyl group.

47. A chartreusin derivative as an intermediate according to claim 40, wherein $T_1$ is tert-bytyldimethysilyl group, and $T_2$ is a hydrogen atom.

48. A chartreusin derivative as an intermediate according to claim 40, wherein both $T_1$ and $T_2$ are tert-butyldimethyl groups.

49. A 6-O-substituted chartreusin derivative of the formula (XII):

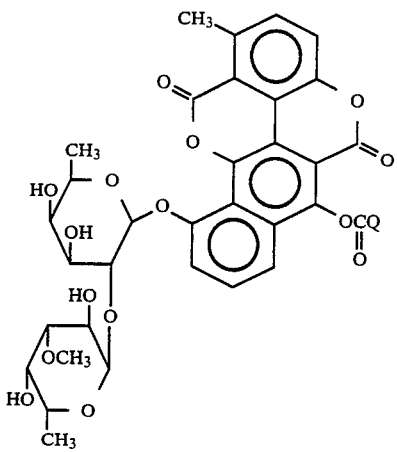

wherein Q is

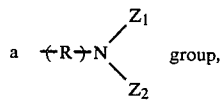 group,

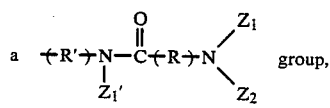 group,

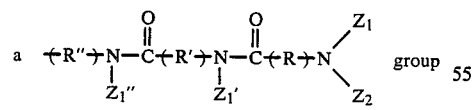 group wherein each of R and R' and R" is
a $C_{1-11}$ alkanediyl group,
a $C_{2-11}$ alkenediyl group,
a $C_{2-11}$ alkynediyl group,
a $C_{3-10}$ cycloalkanediyl group,
a $C_{5-10}$ cycloalkenediyl group
    wherein each of the $C_{1-11}$ alkanediyl group, the $C_{2-11}$ akenediyl group, the $C_{2-11}$ alkynediyl group, the $C_{3-10}$ cycloalkanediyl group and the $C_{5-10}$ cycloalkenediyl group may be substituted by a halogen atom, a hydroxy group, a mercapto group, a $C_{1-6}$ alkoxy group, a $C_{1-6}$ alkythio group, a $C_{1-6}$ alkylsulfinyl group, a $C_{1-6}$ alkylsulfonyl group, an aminocarbonyl group, a hydroxycarbonyl group, a $C_{1-5}$ alkoxycarbonyl group, a phenyl group which may be substituted by a halogen atom or a hydroxy group or a mercapto group or a $C_{1-3}$ alkoxy group or a $C_{1-3}$ alkylthio group, or a 3-indolyl group which may be substituted by a halogen atom, or each or R, R' and R" is a phenyllene group which may be substituted by a halogen atom, a hydroxyl group, a mercapto group, a $C_{1-6}$ akoxy group, a $C_{1-6}$ alkylthio group, a $C_{1-6}$ alkylsufinyl group, or a $C_{1-5}$ akoxycarbonyl group;

each of $Z_1$, $Z'_1$ and $Z''_1$ is a hydrogen atom, or a $C_{1-6}$ alkyl group which may be substituted by a halogen atom, a hydroxyl group, a mercapto group, a $C_{1-3}$ alkoxy group, or a $C_{1-3}$ alkylthio group;

$Z_2$ is
a hydrogen atom,
a formyl group,
a $C_{1-6}$ alkyl group,
a $C_{1-6}$ alkylcarbonyl group,
a benzoyl group
    wherein each of the $C_{1-6}$ alkyl group, the $C_{1-6}$ alkylcarbonyl group and the benzoyl group may be substituted by the same substitutent as substitutent for said $C_{1-6}$ alkyl group as each of $Z_1$, $Z'_1$ and $Z''_1$,
or $Z_2$ is a benzyloxycarbonyl group which may be substituted by a halogen atom;

$Z_1$ and $Z_2$, when taken togehter with the nitrogen atom, may form a nitrogen-containing $C_{2-10}$ heterocyclic group which may be substituted by the same substituent as substitutent for said $C_{1-6}$ alkyl group as each of $Z_1$, $Z'_1$ and $Z''_1$, or Q is
a $C_{1-11}$ alkyl group,
a $C_{2-11}$ alkenyl group,
a $C_{3-11}$ alkynyl group,
a $C_{3-10}$ cycloalkyl group,
a $C_{5-10}$ cycloalkenyl group,
a $C_{1-10}$ alkylcarbonyl group,
a $C_{1-10}$ akoxycarbonyl group,
    wherein each of the $C_{1-11}$ alkyl group, the $C_2$-alkenyl group, the $C_{3-11}$ alkynyl group, the $C_{3-10}$ cycloalkyl group, the $C_{5-10}$ cycloalkenyl group, the $C_{1-10}$ alkylcarbonyl group and the $C_{1-10}$ alkxoycarbonyl group may be substituted by a halogen atom, a hydroxyl group, a mercapto group, a cyano group, a notro group, a $C_{1-6}$ alkoxy group, a $C_{1-6}$ akylthio group, a $C_{1-6}$ alkylsulfinyl group, a $C_{1-6}$ alkylsulfonyl group, a $C_{1-6}$ alkylcarbonyl group, a $C_{1-6}$ alkoxycarbonyl group, a $C_{1-6}$ phenoxycarbonyl group, a $C_{1-6}$ alkylcarbonyloxy group, a $C_{3-7}$ cycloalkyl group, a phenyl group, a phenoxy group, a phenylthio group, a phenylsulfinyl group, a phenylsulfonyl group, a benzoyl group, a benzoyloxy group or a benzyloxy group
    wherein each of the $C_{1-6}$ alkoxy group, the $C_{1-6}$ alkylthio group, the $C_{1-6}$ akylsulfinyl group, the $C_{1-6}$ alkylsulfonyl group, the $C_{1-6}$ alkylcarbonyl group, the $C_{1-6}$ alkoxycarbonyl group, the phenoxycarbonyl group, the $C_{1-6}$ alkylcarbonyloxy group, the $C_{3-7}$ cycloalkyl group, the phenyl group, the phenoxy group, the phenylthio group, the phenylsulfinyl group, the phenylsulfonyl group, the benzoyl group, the benzoyloxy group, and benzyloxy group may be substituted by the same substituent as substituent for sadi $C_{1-6}$ alkyl group as each of $Z_1$, $Z_1'$, and $Z_1''$, or Q is a phenyl group which may be substituted by a halogen atom, a hydroxyl group, a mercapto group, a cyano group, a nitro group, a $C_{1-6}$ akylsulfinyl group, a $C_{1-6}$ alkylsulfonyl group, a $C_{1-6}$ alky group, a $C_{1-6}$ alkoxy group, a $C_{1-6}$ alkylthio group, a $C_{1-6}$ alkylcarbonyl group, a $C_{1-6}$ akoxycarbonyl group, or a $C_{1-6}$ alkylcarbonyloxy group wherein each of the $C_{1-6}$ alkyl group, the $C_{1-6}$ alkoxy group, the $C_{1-6}$ akylthio group, the $C_{1-6}$ alkylcarbonyl group, the $C_{1-6}$ alkoxycarbonyl group, and the $C_{1-6}$ alkylcarbonyloxy group may be substituted by teh same substituent as substituent for said $C_{1-6}$ alkyl group as each of $Z_1$, $Z_1'$, and $Z_1''$, the total number of atoms of Q other than hydrogen atoms being 30 or less.

50. A 6-O-substituted chartreusin derivative according to claim 49, wherein each of R, R' and R" in Q is said $C_{1-11}$ alkanediyl group and the total number of atoms of Q other than hydrogen atom is 15 or less.

51. A 6-0-substituted chartreusin derivative according to claim 49, wherein Q is said $C_{1-11}$ alkyl group or said $C_{3-10}$ cycloalkyl group; and the total number of atoms of Q other than hydrogen atom being 15 or less.

* * * * *